(12) United States Patent
Robichaud et al.

(10) Patent No.: US 12,396,796 B2
(45) Date of Patent: *Aug. 26, 2025

(54) SURGICAL KIT FOR KNEE OSTEOTOMIES AND CORRESPONDING PREOPERATIVE PLANNING METHOD

(71) Applicant: LABORATOIRES BODYCAD INC., Québec (CA)

(72) Inventors: Jean Robichaud, Quebec (CA); Hugo Robichaud, Quebec (CA); Geoffroy Rivet-Sabourin, Stoneham (CA)

(73) Assignee: LABORATOIRES BODYCAD INC., Québec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,095

(22) Filed: Oct. 17, 2023

(65) Prior Publication Data

US 2024/0058069 A1 Feb. 22, 2024

Related U.S. Application Data

(63) Continuation of application No. 16/610,039, filed as application No. PCT/CA2019/051149 on Aug. 22, 2019, now Pat. No. 11,819,278.

(Continued)

(51) Int. Cl.
*A61B 17/17* (2006.01)
*A61B 17/16* (2006.01)
(Continued)

(52) U.S. Cl.
CPC .......... *A61B 34/10* (2016.02); *A61B 17/1728* (2013.01); *A61B 17/1764* (2013.01);
(Continued)

(58) Field of Classification Search
CPC ............ A61B 17/1728; A61B 17/1764; A61B 17/1604; A61B 17/1615; A61B 17/1675; A61B 17/1735; A61B 2090/062
See application file for complete search history.

(56) References Cited

U.S. PATENT DOCUMENTS

| 2,002,021 A | 5/1935 | Rouse |
| 5,620,448 A | 4/1997 | Puddu |

(Continued)

FOREIGN PATENT DOCUMENTS

| CN | 103393459 A | 11/2013 |
| CN | 207721848 U | 8/2018 |
| WO | WO-2015/003284 A2 | 1/2015 |

OTHER PUBLICATIONS

Azernikov et al., "Inhomogeneous Axial Deformation for Orthopedic Surgery Planning," Communications in Computer and Information Science, 274:69-85 (2013).

(Continued)

*Primary Examiner* — Tracy L Kamikawa
(74) *Attorney, Agent, or Firm* — MARSHALL, GERSTEIN & BORUN LLP

(57) ABSTRACT

According to an aspect, a preoperative planning method for a high-tibial knee osteotomy procedure is provided. The method includes: a) constructing a 3D model of a patient's bones; b) analyzing the 3D model to select a desired correction angle to apply to the patient's tibia bone to adjust a mechanical axis thereof; c) determining surgical steps required to apply the desired correction angle to the patient's tibia bone; d) designing a patient-specific guide to guide generic surgical tools in performing the surgical steps, the patient-specific guide being designed to conform to the anatomy of the patient's bones based on the 3D model; and e) manufacturing the patient-specific guide designed in step (Continued)

d). A corresponding kit, system and computer readable medium for performing the method are also provided.

19 Claims, 32 Drawing Sheets

Related U.S. Application Data

(60) Provisional application No. 62/722,403, filed on Aug. 24, 2018.

(51) Int. Cl.
| | |
|---|---|
| *A61B 34/10* | (2016.01) |
| *B33Y 50/02* | (2015.01) |
| *B33Y 80/00* | (2015.01) |
| *G16H 20/40* | (2018.01) |
| *G16H 50/50* | (2018.01) |
| *A61B 90/00* | (2016.01) |
| *B29L 31/00* | (2006.01) |

(52) U.S. Cl.
CPC ............... *B33Y 50/02* (2014.12); *B33Y 80/00* (2014.12); *G16H 20/40* (2018.01); *G16H 50/50* (2018.01); *A61B 17/1604* (2013.01); *A61B 17/1615* (2013.01); *A61B 17/1675* (2013.01); *A61B 17/1735* (2013.01); *A61B 2034/104* (2016.02); *A61B 2034/105* (2016.02); *A61B 2034/108* (2016.02); *A61B 2090/062* (2016.02); *B29L 2031/753* (2013.01); *G05B 2219/45171* (2013.01)

(56) References Cited

U.S. PATENT DOCUMENTS

| | | | |
|---|---|---|---|
| 5,749,875 A | 5/1998 | Puddu | |
| 6,017,342 A | 1/2000 | Rinner | |
| 6,066,142 A | 5/2000 | Serbousek et al. | |
| 6,461,359 B1 | 10/2002 | Tribus et al. | |
| 7,794,467 B2 | 9/2010 | McGinley et al. | |
| 7,935,119 B2 | 5/2011 | Ammann et al. | |
| 7,959,637 B2 | 6/2011 | Fox et al. | |
| 8,083,746 B2 | 12/2011 | Novak | |
| 8,092,465 B2 | 1/2012 | Mtezger et al. | |
| 8,137,406 B2 | 3/2012 | Novak et al. | |
| 8,211,112 B2 | 7/2012 | Novak et al. | |
| 8,241,292 B2 | 8/2012 | Collazo | |
| 8,241,293 B2 | 8/2012 | Stone et al. | |
| 8,337,507 B2 | 12/2012 | Lang et al. | |
| 8,388,690 B2 | 3/2013 | Singhatat et al. | |
| 8,409,209 B2 | 4/2013 | Ammann et al. | |
| 8,484,001 B2 | 7/2013 | Glozman et al. | |
| 8,594,395 B2 | 11/2013 | Roose et al. | |
| 8,632,547 B2 | 1/2014 | Maxson et al. | |
| 8,709,052 B2 | 4/2014 | Ammann et al. | |
| 8,753,348 B2 | 6/2014 | DiDomenico et al. | |
| 8,828,087 B2 | 9/2014 | Stone et al. | |
| 8,979,866 B2 | 3/2015 | Patel et al. | |
| 8,998,903 B2 | 4/2015 | Price et al. | |
| 9,014,835 B2 | 4/2015 | Azernikov et al. | |
| 9,044,250 B2 * | 6/2015 | Olsen | A61B 17/151 |
| 9,072,555 B2 | 7/2015 | Michel | |
| 9,317,634 B2 | 4/2016 | Davison et al. | |
| 9,456,833 B2 | 10/2016 | Maxson et al. | |
| 9,480,490 B2 | 11/2016 | Metzger et al. | |
| 9,486,228 B2 | 11/2016 | Saw et al. | |
| 9,492,183 B2 * | 11/2016 | Wilkinson | A61B 17/157 |
| 9,603,605 B2 | 3/2017 | Collazo | |
| 9,687,261 B2 | 6/2017 | Serbousek et al. | |
| 9,707,023 B2 | 7/2017 | Ammann et al. | |
| 9,770,302 B2 | 9/2017 | Kang et al. | |
| 9,814,533 B2 | 11/2017 | Park et al. | |
| 9,833,245 B2 | 12/2017 | Maxson | |
| 9,877,758 B2 | 1/2018 | Michel | |
| 9,877,790 B2 | 1/2018 | Bojarski et al. | |
| 9,943,348 B2 | 4/2018 | Schelling | |
| 10,245,089 B2 | 4/2019 | Paik | |
| 11,819,278 B2 * | 11/2023 | Robichaud | G16H 50/50 |
| 2005/0209599 A1 | 9/2005 | Brunsvold | |
| 2006/0052795 A1 | 3/2006 | White | |
| 2007/0191848 A1 | 8/2007 | Wack et al. | |
| 2009/0082816 A1 | 3/2009 | Graham et al. | |
| 2011/0213376 A1 | 9/2011 | Maxson et al. | |
| 2013/0338673 A1 | 12/2013 | Keppler | |
| 2015/0051650 A1 | 2/2015 | Verstreken et al. | |
| 2015/0305752 A1 | 10/2015 | Eash | |
| 2016/0038159 A1 | 2/2016 | Park et al. | |
| 2016/0095634 A1 | 4/2016 | Meyer | |
| 2016/0113784 A1 | 4/2016 | Robichaud | |
| 2016/0192949 A1 * | 7/2016 | Robichaud | A61B 17/1764 606/87 |
| 2016/0213384 A1 | 7/2016 | Fallin et al. | |
| 2016/0235454 A1 | 8/2016 | Treace et al. | |
| 2017/0100132 A1 | 4/2017 | Collazo et al. | |
| 2017/0325823 A1 | 11/2017 | Phillips-Hungerford et al. | |
| 2017/0325826 A1 | 11/2017 | Bake et al. | |
| 2018/0368860 A1 | 12/2018 | Wodajo et al. | |

OTHER PUBLICATIONS

International Search Report and Written Opinion for Application No. PCT/CA2019/051147, dated Oct. 15, 2019.
International Search Report and Written Opinion for Application No. PCT/CA2019/051148, dated Oct. 24, 2019.
International Search Report and Written Opinion for Application No. PCT/CA2019/051149, dated Oct. 7, 2019.
International Search Report and Written Opinion for Application No. PCT/CA2019/051151, dated Oct. 22, 2019.
International Search Report and Written Opinion for Application No. PCT/CA2019/051153, dated Sep. 25, 2019.
International Search Report and Written Opinion for Application No. PCT/CA2019/051156, dated Sep. 30, 2019.
International Search Report and Written Opinion for Application No. PCT/CA2019/051157, dated Oct. 25, 2019.

* cited by examiner

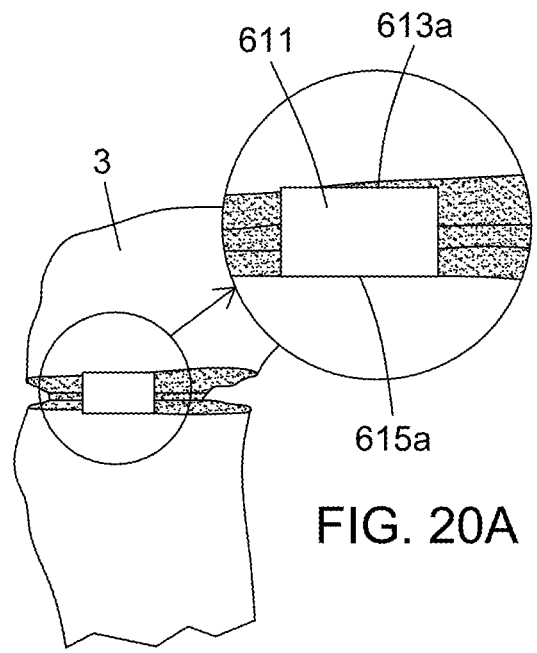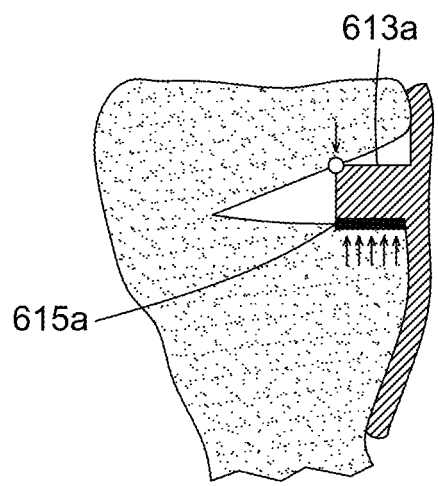
FIG. 20   FIG. 20A   FIG. 20B
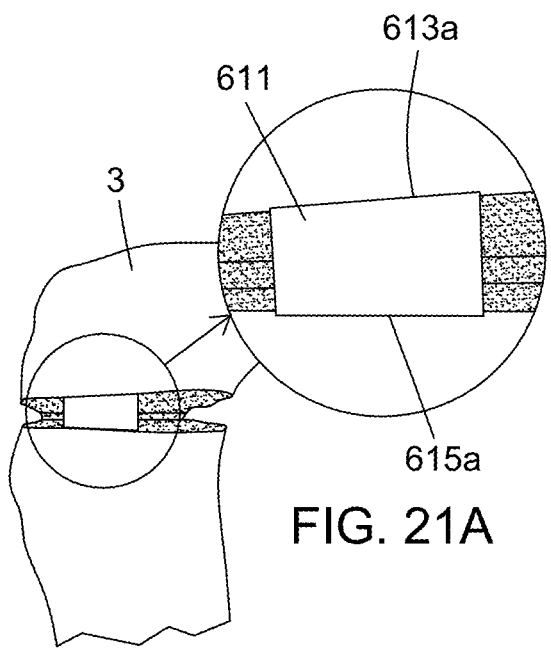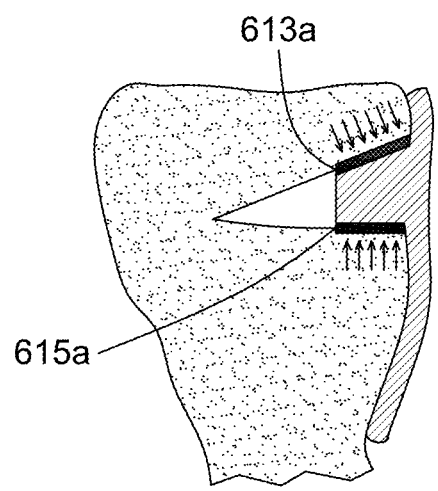
FIG. 21   FIG. 21A   FIG. 21B

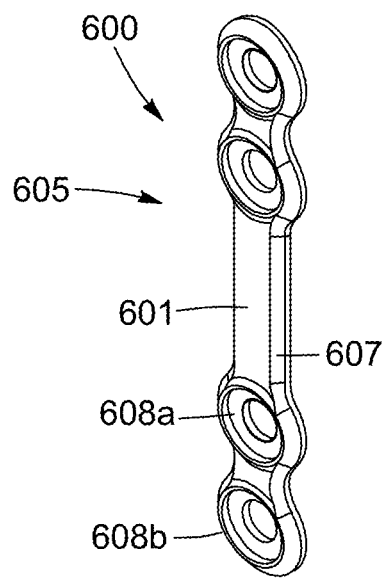
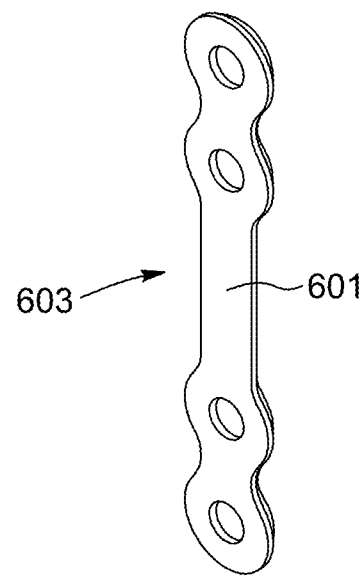
FIG. 25A    FIG. 25B
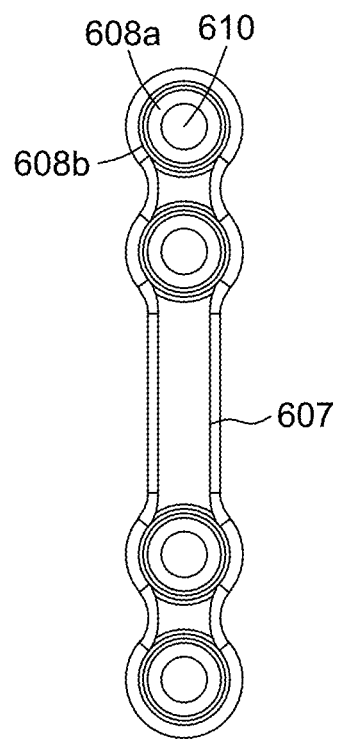
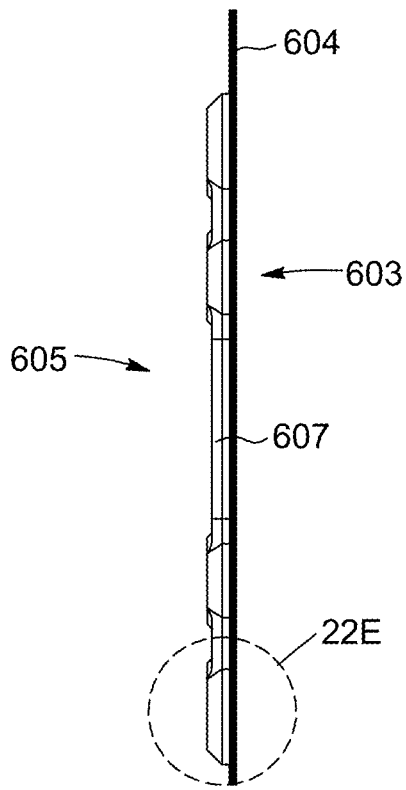
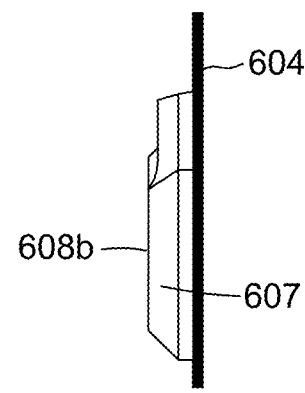
FIG. 25C    FIG. 25D    FIG. 25E

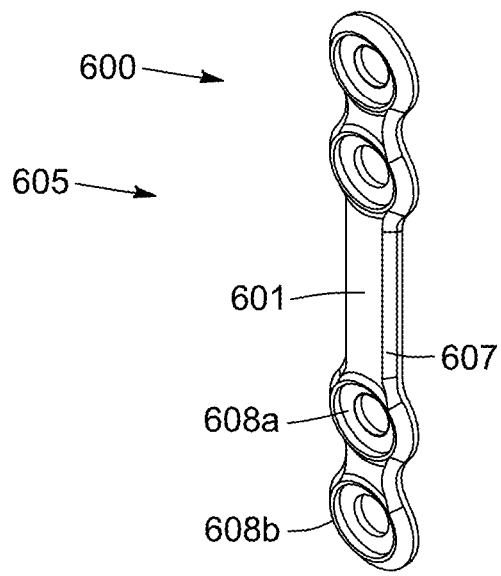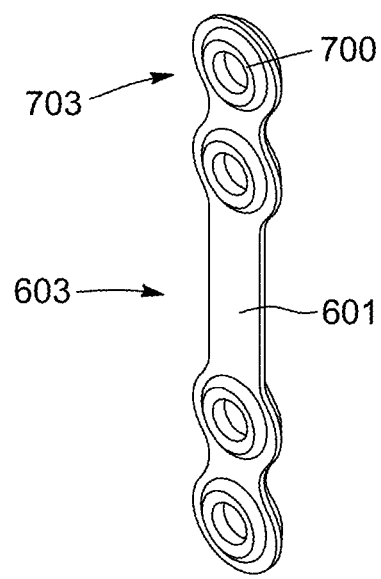
FIG. 26A  FIG. 26B
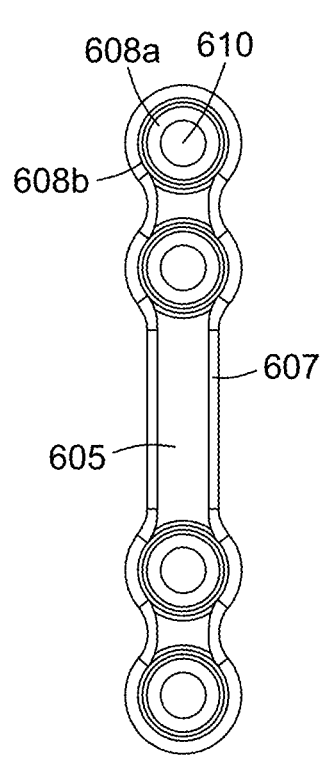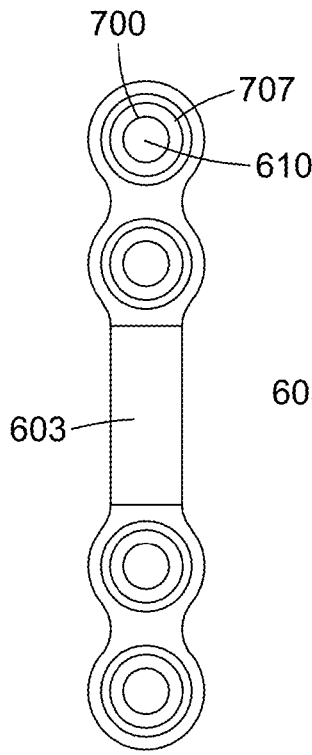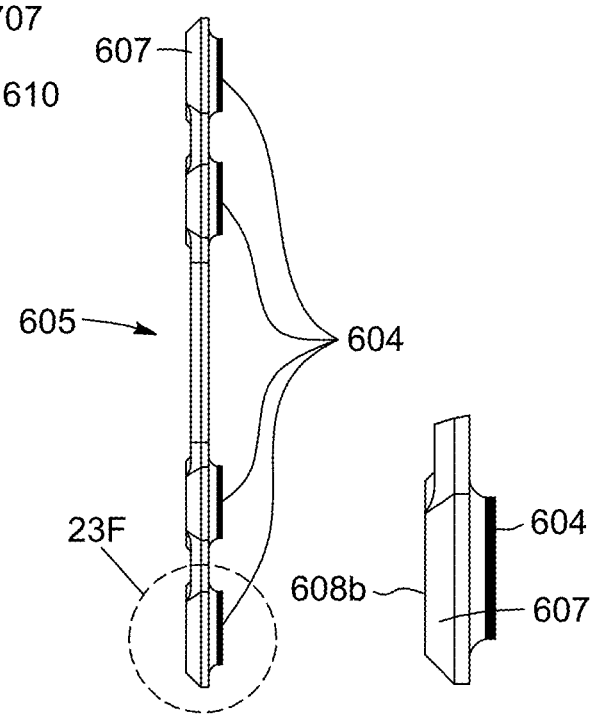
FIG. 26C  FIG. 26D  FIG. 26E  FIG. 26F

SURGICAL KIT FOR KNEE OSTEOTOMIES AND CORRESPONDING PREOPERATIVE PLANNING METHOD

RELATED APPLICATIONS

This application is a continuation of U.S. patent application Ser. No. 16/610,039, filed Oct. 31, 2019, entitled "Surgical Kit for Knee Osteotomies and Corresponding Preoperative Planning Method," which claims the benefit of U.S. Provisional Application No. 62/722,403, filed Aug. 24, 2018, entitled "Surgical Kit for Knee Osteotomies and Corresponding Preoperative Planning Method", the entire disclosures of which are incorporated herein by reference.

TECHNICAL FIELD

The technical field generally relates to tools used in knee osteotomy procedures, and more particularly in high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, a preoperative planning method for a high-tibial knee osteotomy procedure is provided. The method includes the steps of: a) constructing a 3D model of a patient's bones; b) analyzing the 3D model to select a desired correction angle to apply to the patient's tibia bone to adjust a mechanical axis thereof; c) determining surgical steps required to apply the desired correction angle to the patient's tibia bone; d) designing a patient-specific guide to guide generic surgical tools in performing the surgical steps, the patient-specific guide being designed to conform to the anatomy of the patient's bones using the 3D model; and e) manufacturing the patient-specific guide designed in step d).

According to an aspect, a computer system is provided. The computer system is configured to: a) receive a 3D model of a patient's bones; b) analyze the 3D model to select a desired correction angle to apply to the patient's tibia bone to adjust a mechanical axis thereof; c) determine surgical steps required to apply the desired correction angle to the patient's tibia bone; d) design a patient-specific guide to guide generic surgical tools in performing the surgical steps, the patient-specific guide being designed to conform to the anatomy of the patient's bones using the 3D model; and e) transmit instructions to a manufacturing device to manufacture the patient-specific guide designed in step d).

According to an aspect, a non-transitory computer-readable medium is provided. The non-transitory computer-readable medium has instructions stored thereon which, when executed by the computer, cause the computer to perform the steps of: a) receiving a 3D model of a patient's bones; b) analyzing the 3D model to select a desired correction angle to apply to the patient's tibia bone to adjust a mechanical axis thereof; c) determining surgical steps required to apply the desired correction angle to the patient's tibia bone; d) designing a patient-specific guide to guide generic surgical tools in performing the surgical steps, the patient-specific guide being designed to conform to the anatomy of the patient's bones using the 3D model; and e) transmitting instructions to a manufacturing device to manufacture the patient-specific guide designed in step d).

According to an aspect, a surgical kit for performing a high-tibial knee osteotomy is provided. The surgical kit includes a plurality of generic tools, and at least one patient-specific guide configured to cooperate with the generic tools to guide the same in performing steps of the high-tibial knee osteotomy procedure as determined according to a preoperative plan.

According to an aspect, a fixation plate for securing an opening formed in a bone is provided. The fixation plate includes: a body securable to the bone, the body having a bone interface side and an outward facing side; and a wedge element extending from the bone interface side of the body for inserting into the opening formed in the bone; wherein the wedge element is shaped to conform to contours of the opening formed in the bone.

In an embodiment, the wedge element includes a proximal abutment for abutting against a proximal internal surface of the bone in the opening, and a distal abutment for abutting against a distal internal surface of the bone in the opening.

In an embodiment, the proximal and distal abutments have respective bearing surfaces sized to abut against cortical sections of the proximal and distal internal surfaces of the bone.

In an embodiment the wedge element extends along a width between an anterior side and a posterior side of body, further wherein at least one of the bearing surfaces is tapered along the width.

In an embodiment, the wedge element extends from the body along a depth, further wherein at least one of the bearing surfaces is tapered along the depth.

In an embodiment, the bearing surfaces extend between anterior and posterior side edges, further wherein at least one of the anterior and posterior side edges are tapered.

In an embodiment, the bearing surfaces of the proximal and distal abutments have respective surface areas which are different from one another.

In an embodiment, the bearing surfaces of the proximal and distal abutments are offset from one another.

In an embodiment, the proximal and distal abutments are spaced apart from one another via a canal.

In an embodiment, the canal is an evolutive canal having a shape which progressively changes along a width of the wedge element.

In an embodiment the canal is shaped with a curved depth profile.

In an embodiment, the wedge element comprises an anterior wedge member positioned proximate to an anterior side of plate body, and a posterior wedge member positioned proximate to a posterior side of plate body.

In an embodiment, the anterior and posterior wedge members are space apart from one another via an opening in the plate body.

In an embodiment, the wedge element comprises an anterior section extending from a posterior side of the plate body along a width, and a posterior section extending from the anterior section along a width.

In an embodiment, the anterior and posterior sections of wedge element together define an extended wedge element having a curved profile following a contour of the bone.

In an embodiment, the extended wedge element is shaped to extend along at least a first face of the bone, and a second face of the bone posterior to the first face.

According to an aspect, a fixation plate for securing an opening formed in a bone is provided. The fixation plate includes: a body securable to the bone, the body having a bone interface side and an outward facing side; and a wedge element extending from the bone interface side of the body for inserting into the opening formed in the bone; wherein the wedge element comprises a proximal abutment for abutting against a proximal internal surface of the bone in the opening, and a distal abutment for abutting against a distal internal surface of the bone in the opening, said proximal and distal abutments being spaced apart from one another via a canal.

In an embodiment, the canal is an evolutive canal, having a shape which progressively changes along a width of the wedge element.

According to an aspect, a method for designing a patient-specific fixation plate is provided. The method includes the steps of: a) obtaining 3D model of the patient's bone; b) determining an expected shape of an opening to be formed in the patient's bone using the 3D model; c) designing a fixation plate having a body and a wedge element extending therefrom, and configuring the wedge element to conform to the expected shape of the opening; and d) manufacturing the fixation plate according to the design.

In an embodiment, the method further includes the steps of determining a desired amount of flexure to allow in the wedge element and configuring the wedge element with an evolutive canal to allow the desired amount of flexure subject to a load applied thereacross.

According to an aspect, a spacing element for spacing a fixation plate away from a bone to which the fixation plate is secured is provided. The spacing element has a body with a bone interface side and a plate interface side and sidewalls extending thereinbetween, said bone interface side having a bone contacting surface having contours conforming to surface contours of the bone.

In an embodiment, the sidewalls define a central aperture extending through the body for receiving a fastener therethrough, the central aperture opening on the bone interface side and on the plate interface side.

In an embodiment, the plate interface side has a plate contacting surface which is substantially planar.

In an embodiment, the plate interface side has a plate contacting surface having contours conforming to surface contours of the plate.

In an embodiment, the plate interface side is configured to engage with the plate in a predetermined orientation.

In an embodiment, the body is substantially cylindrical in shape.

In an embodiment, the body is made from a rigid, biocompatible material.

In an embodiment, body is made from metal.

According to an aspect, a fixation plate kit is provided. The fixation plate kit includes: a fixation plate having a body with a bone interface side and an outward facing side, the body having a plurality of fastener apertures defined therein for receiving fasteners to secure the fixation plate to a bone; and a plurality of spacing elements for positioning between the fixation plate and the bone when the fixation plate is secured to the bone, each of the spacing elements having a body with a bone interface side for contacting the bone, a plate interface side for contacting the plate, and sidewalls extending between the bone interface side and the plate interface side, the bone interface side of the spacing elements having a bone contacting surface with contours conforming to surface contours of the bone.

In an embodiment, the fixation plate is configured to secure to a predetermined position on the bone, further wherein the bone interface side of the fixation plate has contours following surface contours of the bone at the predetermined position.

In an embodiment, each of the plurality of spacing elements is configured to interface with the bone at predetermined positions relative thereto, further wherein the bone contacting surfaces of the plurality of spacing elements have surface contours conforming to the surface contours of the bone at the predetermine positions.

In an embodiment, each of the plurality of spacing elements is configured to interface with the fixation plate at predetermine positions relative thereto, further wherein the bone contacting surfaces of the plurality of spacing elements have surface contours conforming to the surface contours of the bone at the predetermined positions.

In an embodiment, each of the plurality of spacing elements is configured to interface with the fixation plate in alignment with a corresponding one of the fastener apertures.

In an embodiment, the sidewalls of the spacing elements define thicknesses thereof, further wherein each of the plurality of spacing elements is configured with a thickness to provide a uniform spacing between the bone and the bone interface side of the fixation plate body.

In an embodiment, the body has recesses defined on the bone interface side thereof configured to engage with corresponding spacing elements.

According to an aspect, a fixation plate for securing to a bone is provided. The fixation plate includes: a body having a bone interface side and an outward facing side, the bone interface side having surface contours conforming to surface contours of a predetermined position of the bone; and a plurality of spacing elements extending from the bone interface side for spacing the bone interface side of the body away from the bone when the fixation plate is secured thereto.

In an embodiment, each of the plurality of spacing elements has a bone contacting surface with contours conforming to the surface contours of the predetermined position of the bone.

In an embodiment, the fixation plate body has a plurality of fastener apertures defined therein for receiving fasteners to secure the fixation plate to the bone, further wherein the spacing elements are positioned in alignment with the fastener apertures.

In an embodiment, the spacing element comprises annular bumps extending from the fixation plate body around the fastener apertures on the bone interface side of the body.

In an embodiment, the spacing element is integrally formed as part of the fixation plate body.

According to an aspect, a surgical guide assembly for performing a knee osteotomy procedure is provided. The assembly includes: a body for securing to a patient's tibia bone; and a plurality of guide modules removably attached to the body, each guiding module being adapted to receive a corresponding surgical tool and to guide the corresponding surgical tool along a predetermined path during the knee osteotomy procedure.

In an embodiment, the plurality of guide modules includes at least one drilling module removably secured to the body, each drilling module including a plurality of drill guides for cooperating with a plurality of corresponding drill bits to guide a position, depth, and angle thereof to form drill holes in the patient's tibia bone in a predetermined configuration to weaken the patient's tibia bone in preparation for forming a cut therein.

In an embodiment, the drill guides are positioned and oriented in a co-planar, parallel arrangement to define parallel drill holes in the patient's bone in a common plane.

In an embodiment, the drill guides include a first group of parallel drill guides for creating drill holes in a first plane, and a second group of parallel drill guides for creating drill holes in a second plane.

In an embodiment, the body has a drill module interface adapted for selectively connecting one of the at least one drilling module.

In an embodiment, the at least one drilling module includes a first drilling module for guiding drill bits to form drill holes in a first parallel orientation in a common plane and a second drilling module for guiding drill bits to form drill holes in a second parallel orientation different from the first parallel orientation, and in the same common plane.

In an embodiment, the plurality of guide modules further includes a cutting module secured to the body, the cutting module including a slot sized and shaped to receive a corresponding osteotome therein, and to guide the osteotome to cut the patient's tibia bone at a position, angle, and depth corresponding to an area of the patient's tibia bone weakened by the drilling module.

In an embodiment, the cutting module is positioned adjacent the patient's tibia bone, and the drilling module is positioned adjacent the cutting module.

In an embodiment, the body includes an anchor module for anchoring removable modules relative to the patient's bone, the anchor module including a removable module interface for selectively interfacing with one of the guiding modules.

In an embodiment, the removable module interface includes at least one aperture for receiving corresponding protrusions extending from a removable module.

In an embodiment, the body includes a first section and a second section detachably connected to the first section.

In an embodiment, the second section is configured to be secured to an anterior surface of the patient's tibia bone, and the first section is configured to be secured to the patient's tibia bone lateral relative to the second section, the anchor module being provided in the first section.

In an embodiment, the first and second sections are independently securable relative to the patient's tibia bone to allow one of the first and second sections to be removed from the patient's tibia bone while the other one of the first and second sections remains secured to the patient's tibia bone.

In an embodiment, the anchor module includes a proximal section positioned proximate the joint between the patient's femur and tibia bones, and a distal section spaced further away from the joint between the femur and tibia.

In an embodiment, the proximal and distal sections are separable from one another to allow them to move independently while being secured to different sections of the patient's tibia bone.

In an embodiment, the plurality of guide modules further includes a predrilling module for predrilling holes in the patient's tibia bone for receiving fasteners to secure at least one of a plate and an implant to the patient's tibia bone.

In an embodiment, the predrilling module includes a predrilling module body having a bone interface side for abutting against the patient's tibia bone, an operative side opposite the bone interface side and a plurality of drill guides extending from the operative side for guiding corresponding drill bits.

In an embodiment, the predrilling module further includes an attachment mechanism for at least one of securing the predrilling module relative to the patient's tibia bone and assuring proper alignment of the predrilling module relative to the patient's tibia bone.

In an embodiment, the attachment mechanism includes an attachment interface for interfacing with the removable module interface of the anchor module to attach the predrilling module to the anchor module, the attachment mechanism allowing the predrilling module to be positioned in only one position when attached to the anchor module.

In an embodiment, the attachment interface includes two protrusions sized and shaped to engage in corresponding apertures of the anchor module.

In an embodiment, the protrusions are positioned to align with the anchor module while the patient's tibia bone is in a closed configuration to allow the predrilling module to engage with the patient's tibia bone and predrill holes prior to opening the bone.

In an embodiment, the assembly further includes a spreader module configured to operate in cooperation with the anchor module for opening the patient's tibia bone along a planar cut formed therein.

In an embodiment, the spreader module includes an upper arm and a lower arm pivotally connected to one another via a hinge, each one of the upper and lower arms having a load end and an effort end, the upper and lower arms being pivotable such that movement of the effort ends of the upper and lower arms towards one another moves the load ends of the upper and lower arms away from each other.

In an embodiment, the anchor module includes a proximal section and a distal section positioned on the patient's tibia bone on opposite sides of the planar cut, the upper arm including a protrusion for engaging with the proximal section and the lower arm including a protrusion for engaging with the distal section.

In an embodiment, at least some of the plurality of guide modules are removably and interchangeably attachable to the body.

In an embodiment, the body includes a bone interface side for abutting against the patient's tibia bone, the bone interface side including a surface having contours complementary in shape to the surface contours of a predetermined area of the patient's tibia bone.

According to an aspect, a tool for spreading and/or contracting a bone along a cut formed therein as part of a knee osteotomy procedure is provided. The spreading tool includes: an upper arm and a lower arm respectively extending along a length between an effort end and a load end, the upper and lower arms being pivotally connected to one another via a hinge positioned between the effort and load ends; and an anchor interface proximate the load ends for respectively anchoring the load ends of the upper and lower arms relative to respective first and second fixed positions on the bone; the tool being operable, via rotation of the upper and/or lower arms about the hinge, between a closed configuration in which the load ends of the upper and lower arms are proximate one another and an open configuration in which the load ends of the upper and lower arms are spaced apart from one another.

In an embodiment, the upper and lower arms extend opposite one another between the effort and load ends.

In an embodiment, the upper and lower arms are substantially arcuated, and extend away from one another between the hinge and the load ends and/or between the hinge and the effort ends.

In an embodiment, the anchor interface is adapted to engage in an anchor module secured on a surface of the bone.

In an embodiment, the anchor interface includes protrusions extending from the load ends of the upper and lower arms, said protrusions being adapted tor respectively engage in first and second anchoring points of the anchor module positioned on the bone on opposite sides of the cut.

In an embodiment, the protrusions extend substantially perpendicularly from the arms.

In an embodiment, the protrusions are cylindrical and have respective cylindrical axes.

In an embodiment, the protrusions are adapted to rotate about their respective cylindrical axis relative to the anchoring points in which they are respectively engaged.

In an embodiment, the tool further includes an actuating assembly operatively connected to the effort ends of the upper and lower arms, operable to pivot the upper and/or lower arms about the hinge.

In an embodiment, the upper and lower arms respectively have a threaded bore extending therethrough proximate the effort ends, and wherein the actuating assembly comprises a screw mechanism extending through the threaded bores and being adapted to pivot the arms about the hinge upon rotation of the screw mechanism.

In an embodiment, the screw mechanism is adapted to retain the spacing of effort ends when the actuating assembly is not operated.

In an embodiment, the actuating assembly further comprises a hand wheel connected to the screw mechanism for facilitating rotation of the screw mechanism by hand.

In an embodiment, the tool further includes a gauge extending between the upper and lower arms for indicating a magnitude of an opening angle defined between the load ends.

In an embodiment, the gauge includes a scale connected to the upper arm, and movable through an aperture provided in the lower arm.

In an embodiment, the lower arm includes a window communicating with the aperture to allow reading the scale through the window.

In an embodiment, the upper and lower arms are made from a rigid material.

In an embodiment, the upper and lower arms are made from 3D-printable material.

According to an aspect, a tool for spreading and/or contracting a bone along a cut formed therein as part of a knee osteotomy procedure is provided. The tool includes: an upper arm and a lower arm respectively extending along a length between an effort end and a load end, the upper and lower arms being pivotally connected to one another via a hinge positioned between the effort and load ends; an anchor interface proximate the load ends for respectively anchoring the load ends of the upper and lower arms relative to respective first and second anchoring points on opposite sides of the cut in the bone; the tool being operable towards an open configuration in which a spreading force is applied across the first and second anchoring points via the load ends, and towards a closed configuration in which a contracting force is applied across the first and second anchoring points via the load ends.

In an embodiment, the upper and lower arms extend opposite one another between the effort and load ends.

In an embodiment, the upper and lower arms are substantially arcuated, and extend away from one another between the hinge and the load ends and/or between the hinge and the effort ends.

In an embodiment, the anchor interface comprises protrusions extending from the load ends for interfacing with the anchoring points.

In an embodiment, the protrusions extend substantially perpendicularly from the arms.

In an embodiment, the protrusions are cylindrical and have respective cylindrical axes.

In an embodiment, the protrusions are adapted to rotate about their respective cylindrical axis relative to the anchoring points in which they are respectively engaged.

In an embodiment, the tool further includes an actuating assembly operatively connected to the effort ends and being operable to apply the force thereto.

In an embodiment, the upper and lower arms respectively have a threaded bore extending therethrough proximate the effort end, and wherein the actuating assembly comprises a screw mechanism extending through the threaded bores for pivoting the arms about the hinge upon rotation of the screw mechanism.

In an embodiment, the screw mechanism is adapted to retain the spacing of effort ends when the actuating assembly is not operated.

In an embodiment, the actuating assembly further comprises a hand wheel connected to the screw mechanism, for facilitating rotation of the screw mechanism by hand.

In an embodiment, the tool further includes a gauge extending between the upper and lower arms for indicating a magnitude of an opening angle defined between the load ends.

In an embodiment, the gauge comprises a scale connected to the upper arm, and movable through an aperture provided in the lower arm.

In an embodiment, the lower arm comprises a window communicating with the aperture to allow reading the scale through the window.

In an embodiment, the upper and lower arms are made from a rigid material.

In an embodiment, the upper and lower arms are made from 3D-printable material.

According to an aspect, a patient-specific tool is provided for performing a knee osteotomy procedure on a patient's tibia bone having a wedge opening having a top interior surface and a bottom interior surface. The tool includes: a body including a wedge element sized and shaped to fit in the wedge opening, the wedge element having at least one bone contacting surface having contours complementary in shape to the surface contours of the top and bottom interior surfaces of the patient's tibia bone.

In an embodiment, the body includes a handle end to facilitate manipulation of the tool during the knee osteotomy procedure and an operative end comprising the wedge element, the wedge element being shaped and configured to fit snugly in the wedge opening in the patient's tibia bone based on the expected shape thereof as determined according to a pre-operative plan.

In an embodiment, the wedge element includes a top surface shaped to conform to the contour of the top interior surface of the patient's tibia bone and a bottom surface shaped to conform to the contour of the bottom interior surface of the patient's tibia bone.

In an embodiment, the operative end of the body further includes a tab element to limit the insertion depth of the wedge element into the wedge opening.

In an embodiment, the tab element is shaped to conform to the exterior contours of the patient's tibia bone.

In an embodiment, the tab element includes a top surface shaped to conform to the exterior contour of the patient's tibia bone above the wedge opening, and a bottom surface shaped to conform to the exterior contour of the patient's tibia bone below the wedge opening.

In an embodiment, the handle end includes a handle to allow the tool to be easily grasped and manipulated by hand.

In an embodiment, the handle has a rectangular-shaped profile and includes an anterior side and a lateral side, the anterior and lateral sides being marked to indicate proper orientation during the procedure.

In an embodiment, the body includes a bone interface side configured to be positioned against the patient's tibia bone and an operative side comprising a plurality of drill guides extending therefrom for guiding corresponding drill bits for predrilling holes in the patient's tibia bone for receiving fasteners to secure one of a plate and an implant to the patient's tibia bone.

In an embodiment, the bone interface side comprises a bone-contacting surface having contours complementary in shape to the surface contours of the patient's tibia bone, the wedge element extending from the bone interface side.

In an embodiment, the body includes a proximal section for positioning adjacent a surface of the patient's bone above the wedge opening, a distal section for positioning adjacent a surface of the patient's bone below the wedge opening and an intermediate section for spanning the wedge opening, the wedge element being located on the intermediate section.

According to an aspect, a patient-specific opening validating tool is provided for validating a wedge opening of a patient's tibia bone during a knee osteotomy procedure. The tool includes: a body having a handle end to facilitate manipulation of the tool during the knee osteotomy procedure and an operative end comprising a wedge element shaped and configured to fit snugly in the wedge opening in the patient's tibia bone based on the expected shape thereof as determined according to a pre-operative plan.

In an embodiment, the wedge element includes a top surface shaped to conform to the contour of the top interior surface of the patient's tibia bone and a bottom surface shaped to conform to the contour of the bottom interior surface of the patient's tibia bone.

In an embodiment, the operative end of the body further comprises a tab element to limit the insertion depth of the wedge element into the wedge opening.

In an embodiment, the tab element is shaped to conform to the exterior contours of the patient's tibia bone.

In an embodiment, the tab element comprises a top surface shaped to conform to the exterior contour of the patient's tibia bone above the wedge opening, and a bottom surface shaped to conform to the exterior contour of the patient's tibia bone below the wedge opening.

In an embodiment, the handle end includes a handle to allow the tool to be easily grasped and manipulated by hand.

In an embodiment, the handle has a rectangular-shaped profile and includes an anterior side and a lateral side, the anterior and lateral sides being marked to indicate proper orientation during the procedure.

According to an aspect, a method is provided for validating a wedge opening of a patient's tibia bone during a knee osteotomy procedure, the wedge opening having top and bottom interior surfaces, the method including the steps of: providing an opening validating tool including a body having a handle end and an operative end comprising a wedge element shaped and configured to fit snugly in the wedge opening in the patient's tibia bone based on the expected shape thereof as determined according to a pre-operative plan; inserting the opening validating tool into the wedge opening using the handle end such that the wedge element conforms to the contour of interior surfaces of the wedge opening, wherein a snug fit of the wedge element confirms that the correct opening has been formed and an incorrect fit of the wedge element indicates that an adjustment of the wedge opening is necessary.

According to an aspect, a patient-specific predrilling guide is provided for performing a knee osteotomy procedure on a patient's tibia bone, the patient's tibia bone having a wedge opening having a top interior surface and a bottom interior surface. The guide includes: a body for securing to the patient's tibia bone, the body having a bone interface side configured to be positioned against the patient's tibia bone and an operative side comprising a plurality of drill guides extending therefrom for guiding corresponding drill bits for predrilling holes in the patient's tibia bone for receiving fasteners to secure one of a plate and an implant to the patient's tibia bone; and a wedge element extending from bone interface side, the wedge element having at least one bone contacting surface having contours complementary in shape to the surface contours of the top and bottom interior surfaces of the patient's tibia bone to allow the guide to be secured at a predetermined position relative to the wedge opening.

In an embodiment, the bone interface side has contours complementary in shape to the surface contours of the patient's tibia bone.

In an embodiment, the body includes a proximal section for positioning adjacent a surface of the patient's bone above the wedge opening, a distal section for positioning adjacent a surface of the patient's bone below the wedge opening and an intermediate section for spanning the wedge opening, the wedge element being located on the intermediate section.

According to an aspect, a guide for guiding drill bits to form holes in a bone in a predetermined pattern for receiving fasteners to secure an implant to the bone, the guide including: a guide body having a bone interface side opposite an operative side, the bone interface side including a bone contacting surface engageable with a surface of the bone; and a plurality of drill guides extending from the operative side of the guide body for guiding corresponding drill bits; wherein the bone contacting surface of the guide body is configured to substantially conform to surface contours of the bone at a predetermined position on the bone.

In an embodiment, each drill guide includes a guide barrel extending from the operative side along a lengthwise axis and terminating at a terminal end.

In an embodiment, the guide barrels extend from the operative side at predetermined angles and are positioned on the operative side according to the predetermined pattern.

In an embodiment, the guide barrels are adapted to limit insertion depth of the drill bits for forming holes in the bone having a predetermined depth.

In an embodiment, each guide barrel includes sidewalls defining a guide tunnel extending through the guide barrel along the lengthwise axis, the guide tunnel having openings on the bone interface side and operative side of the guide body configured to receive a corresponding drill bit therethrough.

In an embodiment, the sidewalls are adapted to constrain movement of the drill bit to a predetermined depth, position and/or orientation relative to the bone.

In an embodiment, the guide further includes a handle member connected to the guide body adapted to facilitate manipulation and positioning of the guide body.

In an embodiment, the handle member is a rigid elongated member extending from the operative side of the guide body.

In an embodiment, the guide body further comprises fastener apertures for receiving fasteners to secure the guide body to the bone.

In an embodiment, the guide barrels are positioned to assist in forming holes on either side of a planar cut formed in the bone.

In an embodiment, the guide body includes an alignment mechanism configured to engage with an anchor module secured on a surface of the bone and spanning transversely across the planar cut.

In an embodiment, the alignment mechanism includes an attachment interface for respectively interfacing with anchoring points of the anchoring module positioned on either side of the planar cut.

In an embodiment, the attachment interface is configured to interface with the anchoring points in only one orientation.

In an embodiment, the anchoring points include apertures, and wherein the attachment interface comprises protrusions configured to respectively engage in the apertures.

In an embodiment, the guide is configured to assist in forming holes in the bone prior to altering a geometry of the bone.

In an embodiment, the guide body is adapted to span across an opening formed along the planar cut, and includes a proximal section positioned above the opening and a distal section positioned below the opening.

In an embodiment, the guide body further includes an intermediate section spanning the opening between the proximal and distal sections, and an alignment mechanism extending from the intermediate section for engaging the bone to secure the guide body in a predetermined position relative to the bone.

In an embodiment, the alignment mechanism includes a wedge extending from the intermediate section adapted to be inserted within the opening.

In an embodiment, the wedge includes contours configured to match inner surface contours of the opening.

In an embodiment, the guide is made from a rigid material.

In an embodiment, the guide is made from 3D-printable material.

According to an aspect, a method is provided for designing a guide for guiding drill bits to form holes in a bone in a predetermined pattern for securing a knee osteotomy implant on the bone prior to altering a geometry of the bone. The method includes the steps of: creating a digital 3D model of the bone; virtually cutting the 3D model of the bone to form a planar cut therein; virtually opening the 3D model of the bone along the planar cut to a desired opening angle; virtually positioning an implant and corresponding fasteners on the 3D model of the bone to set final positions of drill holes; virtually closing the 3D model of the bone to determine corresponding initial positions of the drill holes; and designing the guide with drill guides positioned according to the initial positions of the drill holes.

According to an aspect, a guide is provided for assisting in forming holes in a bone according to a predetermined pattern for receiving fasteners to secure an implant on the bone. The guide includes: a guide body having a bone interface side opposite an operative side, the bone interface side comprising a bone contacting surface engageable with a surface of the bone; and a plurality of drill guides connected to the operative side of the guide body for guiding corresponding drill bits adapted to form the holes, wherein the drill guides are positioned to guide drill bits to form holes in the bone in initial positions prior to a planned alteration of a geometry of the bone which will cause the drill holes to move into final positions in alignment with fastener apertures in the implant.

In an embodiment, the guide is custom made according to the anatomy of the bone such that the bone contacting surface substantially conforms to surface contours of the bone at a predetermined position on the bone.

In an embodiment, each drill guide comprises a guide barrel extending from the operative side along a lengthwise axis and terminating at a terminal end.

In an embodiment, the guide barrels extend from the operative side at predetermined angles and are positioned on the operative side according to the predetermined pattern.

In an embodiment, the guide barrels are adapted to limit insertion depth of the drill bits for forming holes in the bone having a predetermined depth.

In an embodiment, each guide barrel includes sidewalls defining a guide tunnel extending through the guide barrel along the lengthwise axis, the guide tunnel having openings on the bone interface side and operative side of the guide body configured to receive a corresponding drill bit therethrough.

In an embodiment, the sidewalls are adapted to constrain movement of the drill bit to a predetermined depth, position and/or orientation relative to the bone.

In an embodiment, the guide further includes a handle member connected to the guide body adapted to facilitate manipulation and positioning of the guide body.

In an embodiment, the handle member is a rigid elongated member extending from the operative side of the guide body.

In an embodiment, the guide body further includes fastener apertures for receiving fasteners to secure the guide body to the bone.

In an embodiment, the guide barrels are positioned to assist in forming holes on either side of a planar cut formed in the bone.

In an embodiment, the guide body comprises an alignment mechanism configured to engage with an anchor module secured on a surface of the bone and spanning transversely across the planar cut.

In an embodiment, the alignment mechanism includes an attachment interface for respectively interfacing with anchoring points of the anchoring module positioned on either side of the planar cut.

In an embodiment, the attachment interface is configured to interface with the anchoring points in only one orientation.

In an embodiment, the anchoring points include apertures, and the attachment interface includes protrusions configured to respectively engage in the apertures.

In an embodiment, the guide is made from a rigid material.

In an embodiment, guide is made from 3D-printable material.

According to an aspect, a guide is provided for guiding drill bits to form holes in a bone in a predetermined pattern for receiving fasteners to secure an implant to the bone. The guide includes: a guide body having a bone interface side opposite an operative side, the bone interface side comprising a bone contacting surface engageable with a surface of the bone; a plurality of drill guides extending from the operative side of the guide body for guiding corresponding drill bits; and an alignment mechanism connected to the guide body for engaging with anchoring points on the bone to secure the guide body in a predetermined position relative to the bone, wherein the bone contacting surface of the guide body is configured to substantially conform to surface contours of the bone at a predetermined position on the bone.

In an embodiment, each drill guide comprises a guide barrel extending from the operative side along a lengthwise axis and terminating at a terminal end.

In an embodiment, the guide barrels extend from the operative side at predetermined angles and are positioned on the operative side according to the predetermined pattern.

In an embodiment, the guide barrels are adapted to limit insertion depth of the drill bits for forming holes in the bone having a predetermined depth.

In an embodiment, each guide barrel includes sidewalls defining a guide tunnel extending through the guide barrel along the lengthwise axis, the guide tunnel having openings on the bone interface side and operative side of the guide body configured to receive a corresponding drill bit therethrough.

In an embodiment, the sidewalls are adapted to constrain movement of the drill bit to a predetermined depth, position and/or orientation relative to the bone.

In an embodiment, the guide further includes a handle member connected to the guide body adapted to facilitate manipulation and positioning of the guide body.

In an embodiment, the handle member is a rigid elongated member extending from the operative side of the guide body.

In an embodiment, the guide body further includes fastener apertures for receiving fasteners to secure the guide body to the bone.

In an embodiment, the guide barrels are positioned to assist in forming holes on either side of a planar cut formed in the bone.

In an embodiment, the alignment mechanism is configured to engage with anchoring points on the surface of the bone on either sides of the planar cut.

In an embodiment, the anchoring points comprise apertures, and the alignment mechanism includes protrusions configured to respectively engage in the apertures.

In an embodiment, the alignment mechanism is configured to engage the anchoring points in only one orientation.

In an embodiment, the guide is configured to assist in forming holes in the bone prior to a altering a geometry of the bone.

In an embodiment, the guide body is adapted to span across an opening formed along the planar cut, and comprises a proximal section positioned above the opening and a distal section positioned below the opening.

In an embodiment, the guide body further includes an intermediate section spanning the opening between the proximal and distal sections, and an alignment mechanism extending from the intermediate section for engaging the bone to secure the guide body in a predetermined position relative to the bone.

In an embodiment, the alignment mechanism includes a wedge extending from the intermediate section adapted to be inserted within the opening.

In an embodiment, the wedge includes contours configured to match inner surface contours of the opening.

BRIEF DESCRIPTION OF THE DRAWINGS

FIG. 20 is a perspective view showing an open wedge formed in a patient's tibia bone supported by a straight wedge, according to an embodiment; FIG. 20A is a detail view of the wedge of FIG. 20; FIG. 20B is a partial cross section of the bone and wedge of FIG. 20, showing stress distribution at an interface between the wedge and the bone.

FIG. 21 is a perspective view showing an open wedge formed in a patient's tibia bone supported by a patient-specific, bone conforming wedge, according to an embodiment;

FIG. 21A is a detail view of the wedge of FIG. 21; FIG. 21B is a partial cross section of the bone and wedge of FIG. 21, showing stress distribution at an interface between the wedge and the bone.

FIGS. 25A, 25B, 25C and 25D are respective front perspective, rear perspective, front and side views of a full contact plate, according to an embodiment; FIG. 25E is a detail view of a portion of FIG. 25D showing the contact surface and chamfered edge of the plate.

FIGS. 26A, 26B, 26C, 26D and 26E are respective front perspective, rear perspective, front, rear and side views of a low contact plate, according to an embodiment;

FIG. 26F is a detail view of a portion of FIG. 25E showing the contact surface and chamfered edge of the plate.

DETAILED DESCRIPTION

Figure 1A:
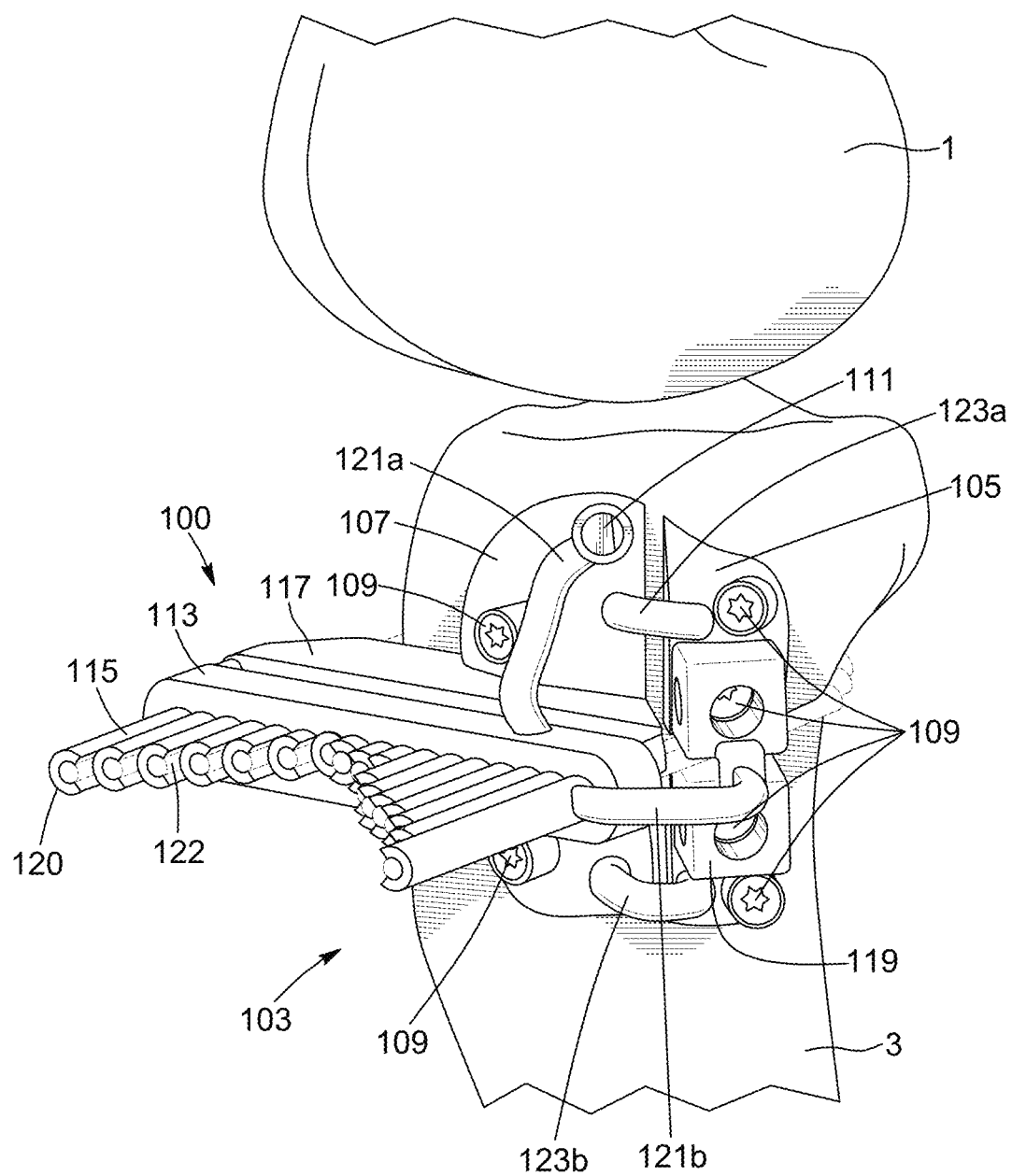
FIG. 1A is a perspective view of a surgical guide secured to a patient's tibia bone, according to an embodiment.
Figure 1B:
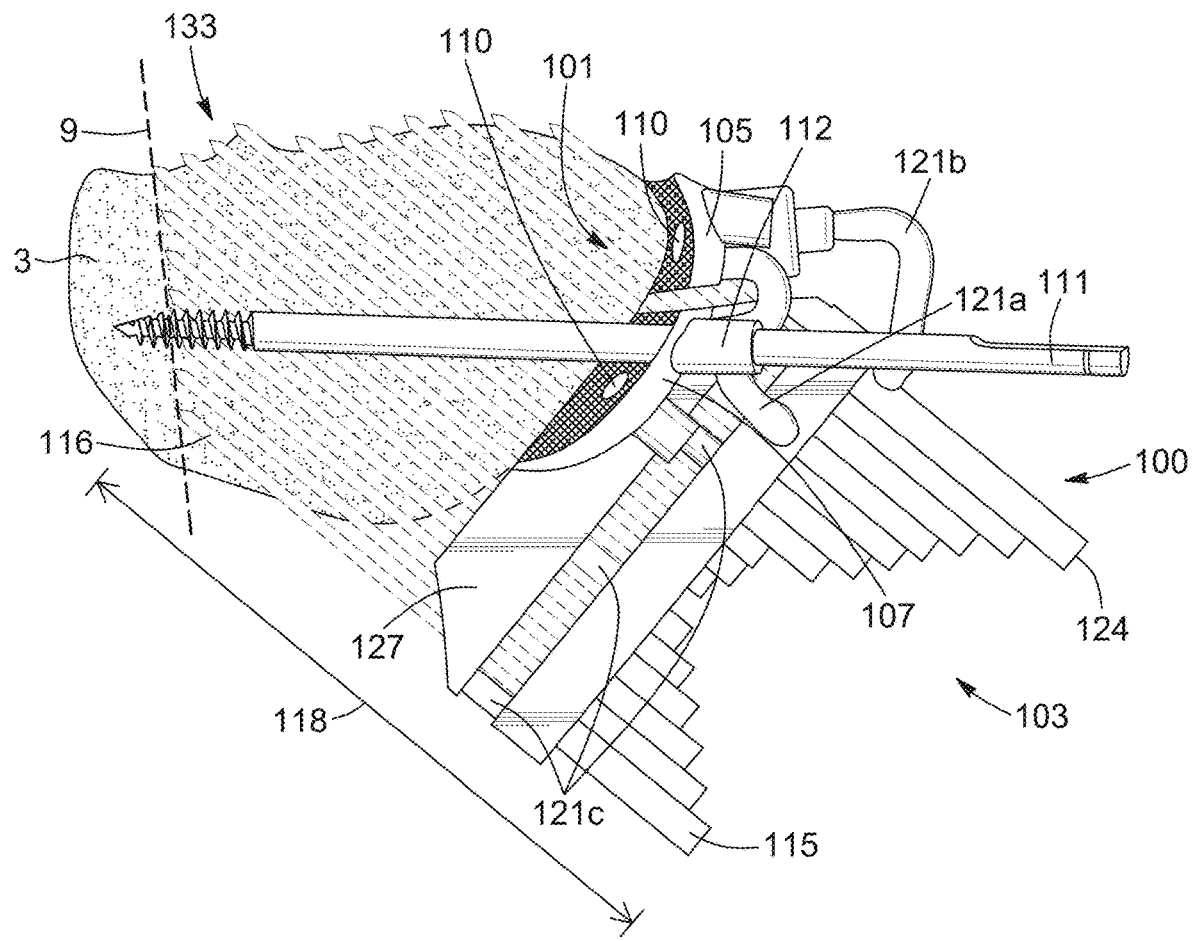
FIG. 1B is a top view of the surgical guide of FIG. 1A, showing drill holes formed through a cross section of the patient's tibia bone.

With reference to FIGS. 1A and 1B a surgical guide 100 is provided according to an embodiment. The surgical guide 100 is configured to be mounted to a patient's tibia bone 3 and includes a plurality of modules to guide various surgical tools used throughout the osteotomy procedure. The surgical guide 100 is patient-specific in that it is designed and manufactured according to the specific anatomy of a patient. In this fashion, the surgical guide 100 can be shaped and configured such that it can fit precisely on a predetermined position on the patient's bone 3 and be secured thereto to assure proper alignment of guides for various surgical tools. In the present embodiment, the surgical guide 100 has a body made from 3D printed plastic, although it is appreciated that other biocompatible materials compatible with other custom manufacturing methods are also possible.

The body of surgical guide 100 comprises a bone interface side 101 for facing the patient's bone 3, and an operative side 103 for facing away from the patient's bone 3. In the present embodiment, bone interface side 101 is configured to be positioned directly on the patient's bone, and comprises a surface having contours complementary is shape to the surface contours of a predetermined area of the patient's bone 3. In this configuration, bone interface side 101 can abut against the patient's bone, and key into a specific position thereon. In the present embodiment, bone interface side 101 comprises a solid surface, however it is appreciated that other configurations are possible. For example, the surface can be defined by an open lattice, and can comprise edges conforming to the contours of the patient's bone 3. Operative side 103 is provided opposite interface side 101 and includes a variety of components for interacting with surgical tools, as will be described in more detail hereinafter.

In the present embodiment, the body of surgical guide 100 is subdivided into two separable sections, including a lateral section 105 for securing relative to a lateral or medial surface of the patient's bone 3 and an anterior section 107 for securing relative to an anterior surface of the patient's bone 3. It is appreciated, however, that in other embodiments, more or fewer sections are possible to secure relative to different surfaces of the patient's bone 3 depending on surgical requirements. In the present embodiment, lateral section 105 and anterior section 107 are independently securable relative to the patient's bone 3. In this fashion, the lateral 105 or anterior 107 section can be removed from the patient's bone 3 when no longer needed, while the other section can remain secured in place. In the present embodiment, lateral 105 and anterior 107 sections are secured directly to the patient's bone, however it is appreciated that in some embodiments, only one of the lateral 105 and anterior 107 need be affixed directly to the bone. For example, lateral section 105 can be affixed directly to the bone 3, whereas anterior section 107 can be removably attached to lateral section 105 such that it is secured relative the patient's bone 3 without being directly affixed thereto.

In the present embodiment, lateral 105 and anterior 107 sections comprise bone-conforming plates secured to the patient's bone 3 via fasteners. The fasteners comprise surgical screws 109 although it is appreciated that other types of fastening mechanisms are also possible. The screws 109 engage in the patient's bone 3 through canals 110 opening on the bone interface 101 and operative 103 sides of the surgical guide 100. The canals 110 comprise sidewalls extending along a length for guiding insertion of screws 109 through canals 110 at a specified angle and depth. In this fashion, screws 109 drilled into the patient's bone 3 through canals 110 can be guided into a predetermined position, orientation and depth such that they can secure patient-specific surgical guide 100 to the patient's bone 3 in an optimal fashion, and such that the screws 109 will not interfere with tools used during subsequent steps during the osteotomy procedure. The sidewalls of canals 110 can further be configured to abut against a head of screw 109 to block the screw 109 from being inserted too deep into the patient's bone 3.

In the present embodiment, a plurality of canals 110 are provided for securing the surgical guide 100 to the patient's bone 3 via a plurality of screws 109 at strategic locations. It is appreciated, however, that in other embodiments, a different number of screws 109 and canals 110 can be provided, and that they can be positioned and oriented differently depending on the patient's specific anatomy and according to the planned procedure. Moreover, in the present embodiment, each of screws 109 is the same size, but it is appreciated that in other embodiments, different sized screws can be used to secure different parts of the surgical guide 100, and that the canals 110 can be sized and shaped accordingly. Finally, although the screws 109 are guided by canals 110 in the present embodiment, it is appreciated that other screw-guiding mechanisms are possible in other embodiments.

As mentioned above, lateral 105 and anterior 107 sections are separable from one another. In the present embodiment, lateral 105 and anterior 107 sections are generally disjointed from one another and are connected via connecting members. In other words, lateral 105 and anterior 107 sections are not directly fused together, and instead comprise separate spaced-apart sections removably secured to one another at a finite number of fixed points. In this configuration, each of lateral 105 and anterior 107 sections define two separate bone-contacting surfaces including two bone-conforming plates on bone interface side 101 of surgical guide 100. It is appreciated, however, that in other embodiments, lateral 105 and anterior 107 sections can together form a single coherent surface or plate for contacting the bone 3.

Connecting members 121, 123, can be provided to removably connect different sections of the surgical guide 100. In the present embodiment, the lateral 105 and anterior 107 sections are connected to one another at three fixed points via connecting members 121*b*, 123*a* and 123*b*. The connecting members 121*b*, 123*a*, 123*b* are stems comprising narrow strands of rigid material connected at a first end to the lateral section 105 and at a second end to the anterior section 107. The connecting members 121*b*, 123*a*, 123*b* are fused to lateral 105 and anterior 107 sections and/or are formed as integral parts thereof. In this fashion, lateral 105 and anterior 107 sections can be rigidly connected to one another and can be disconnected by respectively severing each of connecting members 121*b*, 123*a*, 123*b*. Connecting members 121, 123 are configured such that an intermediate portion thereof is spaced away from surgical guide 100 and/or the patient's bone 3, thereby allowing the connecting members 121, 123 to be readily severed using a severing tool (such as cutting pliers, a saw, or scissors, for example) while minimizing a risk of damaging surgical guide 100 or bone 3. In the present configuration, connecting members 121*b*, 123*a*, 123*b* loop away from the surgical guide 100 and comprise a rounded intermediate section spaced away from surgical guide 100. Although a particular configuration of connecting members 121, 123 has been shown, it is appreciated that other configurations are possible. In other embodiments, connecting members 121, 123 can have different shapes, and can include different connecting elements. For example, in some embodiments, instead of being fused and/or an integral part of lateral 105 and/or anterior 107 sections, connecting members 121, 123 can be separate pieces removably engageable in lateral 105 and/or anterior 107 sections. As can be further appreciated, in other embodiments, a different number of connecting members 121, 123 can be provided, and they can be positioned differently.

As mentioned above, the surgical guide 100 comprises a plurality of modules to guide various surgical tools used throughout the osteotomy procedure. Each module can perform a different function for assisting with various tasks throughout an osteotomy procedure. Some modules can form integral parts of the lateral 105 and/or anterior 107 sections secured directly to the patient's bone 3, whereas other modules can be independent elements which can be secured to relative to the patient's bone 3 by attaching to lateral 105 and/or anterior 107 sections. Although a particular set of modules will be described in detail hereinafter, it is appreciated that other modules and combinations thereof are possible depending on the requirements of the surgical procedure. Moreover, although some modules are described as performing particular functions, it is appreciated that some modules can perform two or more functions and/or have other advantages or uses not explicitly described herein, but that would be readily understood by a person of skill in the art upon reading the present disclosure.

Security Pin Guide Module

In the present embodiment, a security pin guide module is provided for guiding insertion of a corresponding security pin or rod 111 into the patient's bone 3. Security pin guide module is an integral part of body of surgical guide, and comprises a security pin guide 112 formed therein. More specifically, security pin guide 112 is provided on anterior section 107 of surgical guide 100, although it is appreciated that other configurations are possible. In the present embodiment, security pin guide 112 is positioned proximate a top portion of anterior section 107 and comprises a canal to guide an angle of security pin 111 as it is inserted into the patient's bone 3. The pin guide 112 is angled such that when the security pin 111 is inserted into the patient's bone 3 it runs parallel to the tibial plateau. The security pin 111 is made from a rigid, biocompatible material, such as stainless steel or titanium, and can be screwed into the patient's bone 3. Once inserted into the patient's bone 3, the security pin 111 can remain in place for the remainder of the osteotomy procedure to protect the tibial plateau from fracturing. Accordingly, the security pin guide module can be configured to be removable from security pin 111 once the security pin 111 is installed. For example, pin guide 112 can be configured such that security pin 111 can slide therethrough unobstructed, allowing pin 111 to slide out from pin guide 112 when the security pin guide module is removed, for example when the anterior section 107 is removed from the patient's bone 3. Other configurations of pin 111 and pin guide 112 are also possible.

Drilling Module

A drilling module 113 is provided to assist in creating drill holes 116 in the patient's bone 3 in preparation for forming a cut therein. In the present embodiment, the drilling module 113 is removably secured to the body of surgical guide 100 via connecting members 121. More specifically, a plurality of connecting members 121a, 121b, and 121c extend between the drilling module 113 and the body of surgical guide 100, securing the drilling module 113 to lateral 105 and anterior 107 sections of surgical guide 100. The connecting members 121 comprise stems of rigid material forming integral parts of both surgical guide 100 and drilling module 113, and drilling module 113 can be removed from surgical guide 100 by severing stems of connecting members 121.

Figure 9:
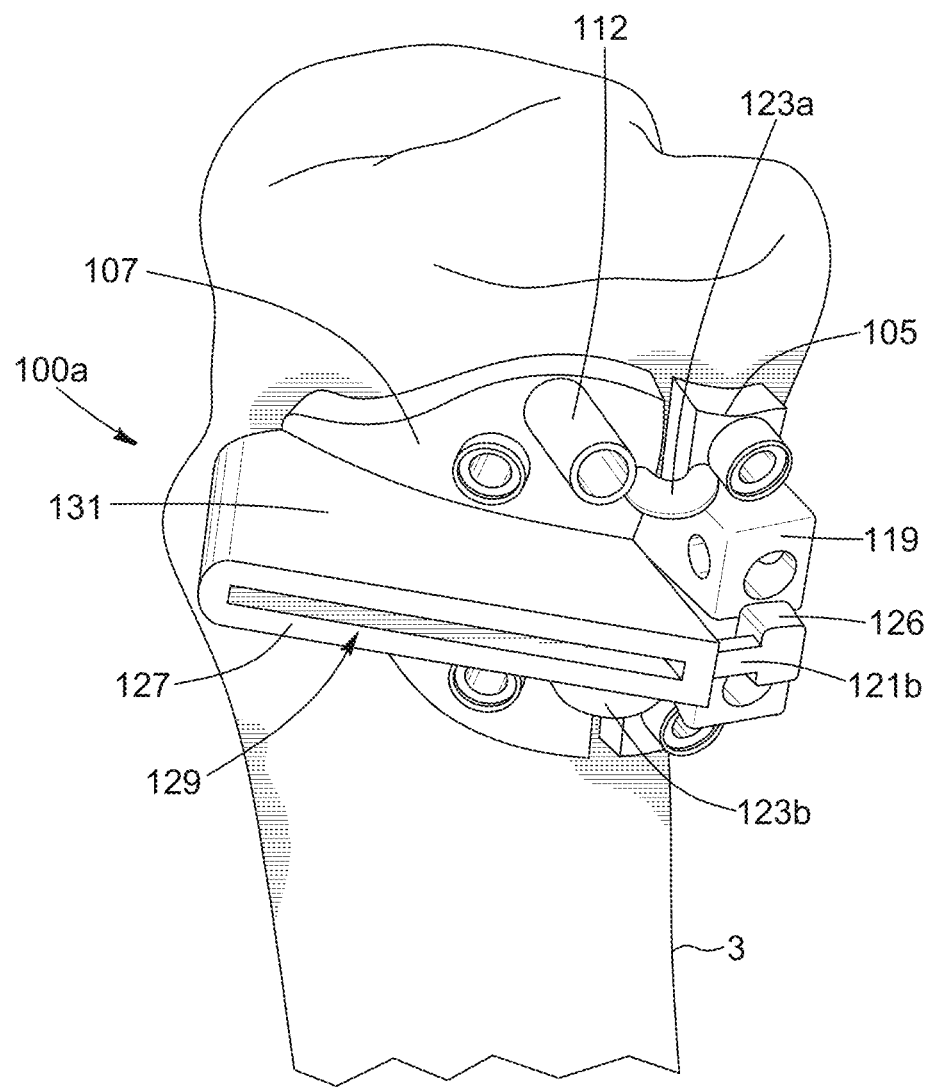
FIG. 9 is a perspective view of a surgical guide secured to the patient's tibia bone, according to an alternate embodiment in which the osteotome guide acts as an interface for connecting a removable drilling module.
Figure 10A:
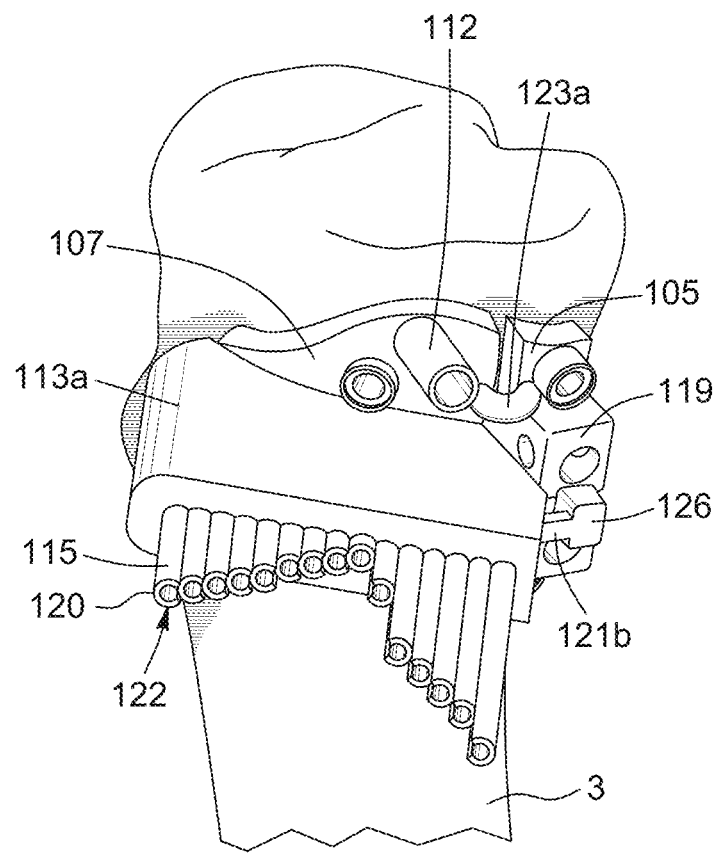
FIG. 10A is a perspective view of the surgical guide of FIG. 9, including a first removable drilling module secured thereto via the osteotome guide.
Figure 10B:
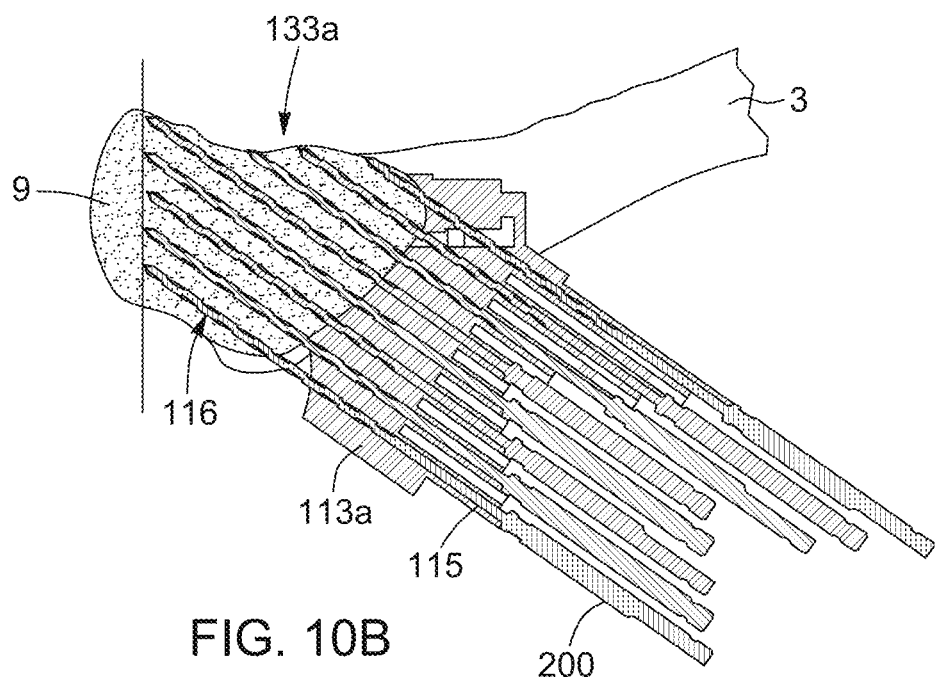
FIG. 10B is a top view of the surgical guide and drilling module of FIG. 10A, showing drill bits forming drill holes through a cross section of the patient's tibia bone.
Figure 11A:
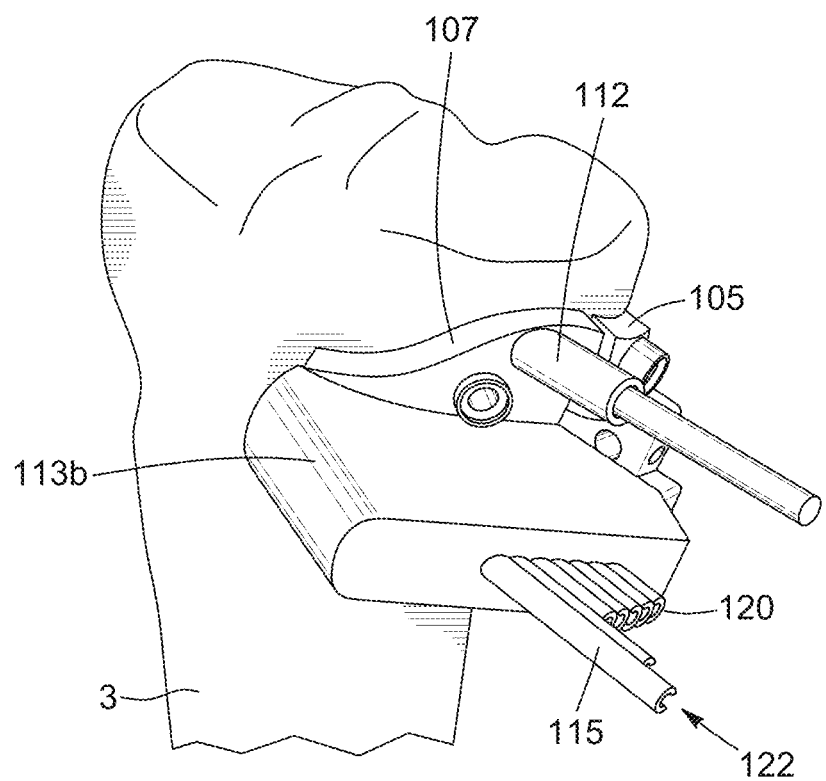
FIG. 11A is a perspective view of the surgical guide of FIG. 9, including a second removable drilling module secured thereto via the osteotome guide.
Figure 11B:
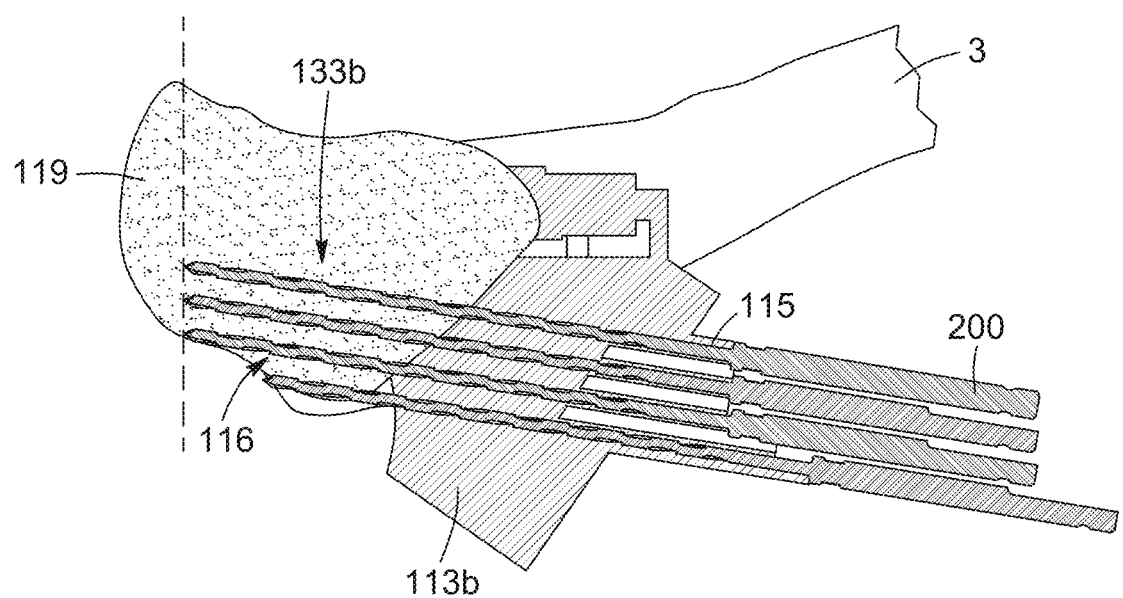
FIG. 11B is a top view of the surgical guide and drilling module of FIG. 11A, showing drill bits forming drill holes through a cross section of the patient's tibia bone.

Although in the present embodiment the drilling module 113 is secured to the body of surgical guide 100 via severable stems, it is appreciated that other connection mechanisms are possible to secure and position drilling module 113 relative to the patient's bone. For example, drilling module can engage with body of surgical guide 100 via fasteners, and/or can engage directly to the patient's bone. In an embodiment, for example as shown in FIG. 9, the drilling module 113 can clip onto a predetermined position on surgical guide 100. In the embodiment of FIG. 9, surgical guide 100a comprises a drill module interface 131 in the form of a tongue element. A corresponding removable drill guide module, such as drill guide modules 113a and 113b shown in FIGS. 10A and 10B, can comprise a slot or groove sized and shaped to receive tongue 131 therein. In this configuration, drill guide module 113a, 113b can clip onto a fixed position on surgical guide 100 by sliding over tongue 131. It is appreciated that in alternate embodiments, drill guide 113 can comprise a tongue for fitting in a corresponding groove in surgical guide 100 and/or a combination of tongue and grooves for fitting with corresponding tongue and groves in surgical guide 100.

Referring back to FIGS. 1A and 1B, the drilling module 113 comprises a plurality of drill guides 115 for cooperating with corresponding drill bits to guide a position, depth, and angle thereof to form drill holes 116 in the patient's bone 3 in a predetermined configuration. In the present embodiment, the drill guides 115 each comprise a guiding element accessible from the operative side 103 of surgical guide 100. The guiding element comprises a guide barrel 120 extending from the operative side 103 of surgical guide 100, although it is appreciated that other types of guide elements are also possible. The guide barrel 120 extends along a lengthwise axis, between a proximal end proximate the bone interface side 101 of guide 100, and a terminal end 124 on the operative side 103 of guide 100. The guide barrel 120 comprises sidewalls defining a hollow interior in the form of a guide tunnel 122 extending through the guide barrel 120 along the lengthwise axis thereof, and opening on the bone interface side 101 and operative side 103 of guide 100. The guide tunnels 122 are sized and shaped to receive a corresponding drill bit therein, allowing the drill bit to slide in and out of barrel 120, while sidewalls of barrel 120 constrain movement of the drill bit to a predetermined depth, position, and orientation relative to the patient's bone.

Figure 2:
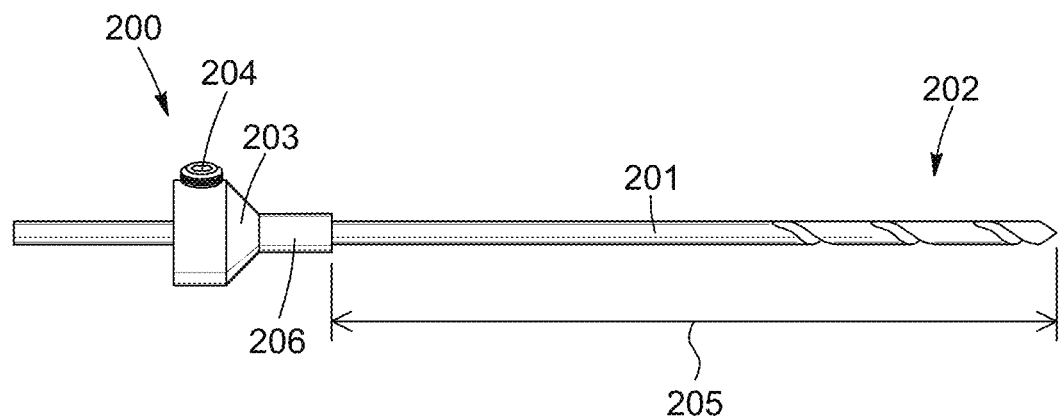
FIG. 2 is a side view of a drill bit configured to cooperate with corresponding drill guides in the surgical guide of FIG. 1A, according to an embodiment.
Figure 2A:
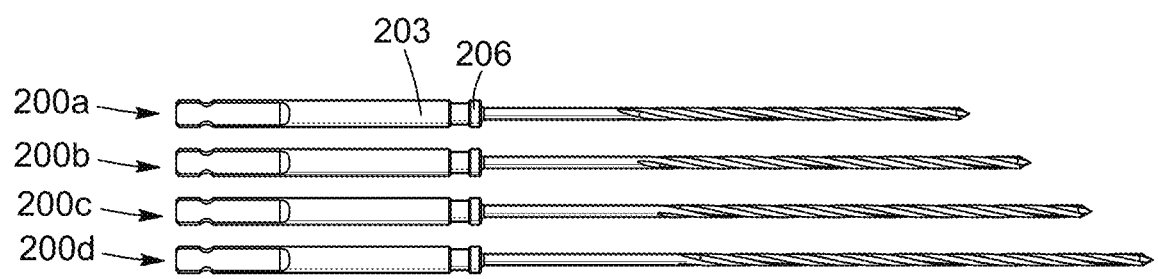
FIG. 2A is a side view of drill bits according to alternate embodiments having depth guides permanently secured relative to their cutting ends.

With reference to FIG. 2, a drill bit 200 configured to cooperate with drill guide is shown according to an embodiment. The drill bit 200 comprises a drill bit body 201 extending along a length, and terminating at a cutting end 202. A depth guide 203 is provided on the drill bit body 201 and spaced away from the cutting end 202, effectively defining an operative length 205 of drill bit 200. In the present embodiment, depth guide 203 is removably secured to drill bit body 201 via fastener 204, allowing operative length 205 of drill bit 200 to be adjusted by loosening fastener 204 and sliding depth guide 203 to a desired location along the length of the drill bit body 201. It is appreciated, however, that in other embodiments, depth guide 203 can be permanently affixed to, and/or form an integral part of, drill bit body 201, effectively defining a fixed predetermined operative length 205. For example, as shown in FIG. 2A, drill bits 200a, 200b, 200c and 200d having respective fixed lengths of 80 mm, 90 mm, 100 mm and 110 mm are shown. Each drill bit comprises a depth guide 203 permanently secured relative to cutting end 202. As can be appreciated, a collection of fixed drill bits can be provided as part of a kit, and each bit can be identified via markings, and/or via color coding. In some embodiments, the markings and/or color coding can match with corresponding marking and/or color coding on the drill guides 115 in the drilling module 113.

With reference now to FIGS. 1A, 1B, 2 and 2A, depth guide 203 comprises an abutment member 206 for limiting an insertion depth of drill bit 200 in guide barrel 120. When operative length 205 of drill bit 200 is fully inserted into guide barrel 120, the abutment member 206 abuts against terminal 124, effectively preventing further insertion of drill bit 200. As can be appreciated, in this configuration, drill bit 200 can only be inserted into guide barrel 120 at a fixed insertion depth 118 relative to the terminal end 124. The position of terminal end 124 relative to the patient's bone 3 thus defines the penetration depth of drill bit 200 into the patient's bone 3. Accordingly, the length of guide barrel 120 determines the bone penetration depth of drill bit 200: a longer guide barrel 120 results in a shallower bone penetration depth of drill bit 200, and a shorter guide barrel results in a deeper bone penetration depth. Similarly, the position and orientation of the guide barrel 120 defines the position and orientation at which the drill bit 200 penetrates the patient's bone 3.

In the present embodiment, a plurality of drill guides 115 are provided for cooperating with a calibrated drill bit 200 having a fixed operative length 205. The drill guides 115 comprise guide barrels 120 positioned and arranged to create drill holes 116 in a predefined pattern to weaken the patient's bone 3 in preparation for a planar cut. More specifically, the drill guides 115 are positioned and oriented in a co-planar, parallel arrangement to define parallel drill holes 116 in the patient's bone 3 in a common plane 133. The guide barrels 120 of drill guides 115 are sized based on the specific geometry of the patient's bone 3, such that the drill holes 116 cover a majority of a cross section of the patient's bone 3, while leaving a non-weakened section to eventually form a hinge along which the patient's bone 3 can be opened. More specifically, the guide barrels 120 are positioned such that drill holes define a hinge axis 9 at a border between weakened and non-weakened areas of the patient's bone 3 in the common plane 133. As can be appreciated, hinge axis 9 can be oriented depending on the type and position of opening to be formed in the patient's bone 3 as determined according to a preoperative plan, to correct the mechanical axis of the patient's bone 3 as needed. In the present embodiment, hinge axis 9 is a straight line, but it is appreciated that other shapes are also possible.

Although in the present embodiment the drilling module 113 is configured to create drill holes 116 in a parallel orientation, it is appreciated that in other embodiments, the drilling module 113 can be configured such that some or all drill holes do not run parallel to one another. For example, the drill holes 116 can be grouped into two or more arrangements which intersect with one another. Although different groups of drill holes can be guided by the same drilling module 113, it is appreciated that in some embodiments, two or more drilling modules 113 can be provided, for example to create drill holes 116 in different arrangements, to weaken the patient's bone 3 in different steps/stages, and/or to allow drill bits to be inserted at different angles of approach. Where a plurality of drilling modules 113 are provided, they can be positioned and/or attached on the same section of the guide 100, or can be positioned on different sections of the guide 100, for example to drill on different faces of the patient's bone 3 and/or allow drill bits to be inserted at different orientations, for example to facilitate drilling holes in a position which would otherwise be more difficult to access.

For example, as shown in FIGS. 9, 10A, 10B, 11A, and 11B, surgical guide 100a can be configured with an anterior section 107 having a drill module interface 131 for connecting one or more removable drill modules 113 thereto. A first drilling module 113a can be attached thereto to guide drill bits 200 to form drill holes 116 in a first parallel orientation 133a in the common plane 133 in the patient's bone. The first drilling module 113a can subsequently be removed, and in its place a second drilling module 113b can be attached to the same position on anterior section 107 via drill module interface 131. The second drilling module 113b can then guide drill bits 200 to form drill holes 116 in a second parallel orientation 133b different from the first parallel orientation 133a, and in the same plane 133. As can be appreciated, the two drilling modules 113a, 113b can allow for weakening the patient's bone 3 along the plane 133 in two phases and by inserting drill bits 200 at different orientations. This can, for example, allow a complete area of the patient's bone 3 to be weakened in preparation for cutting the patients bone, while reducing the size of the tissue incision required to access the patient's bone 3 to perform the procedure.

Figure 12A:
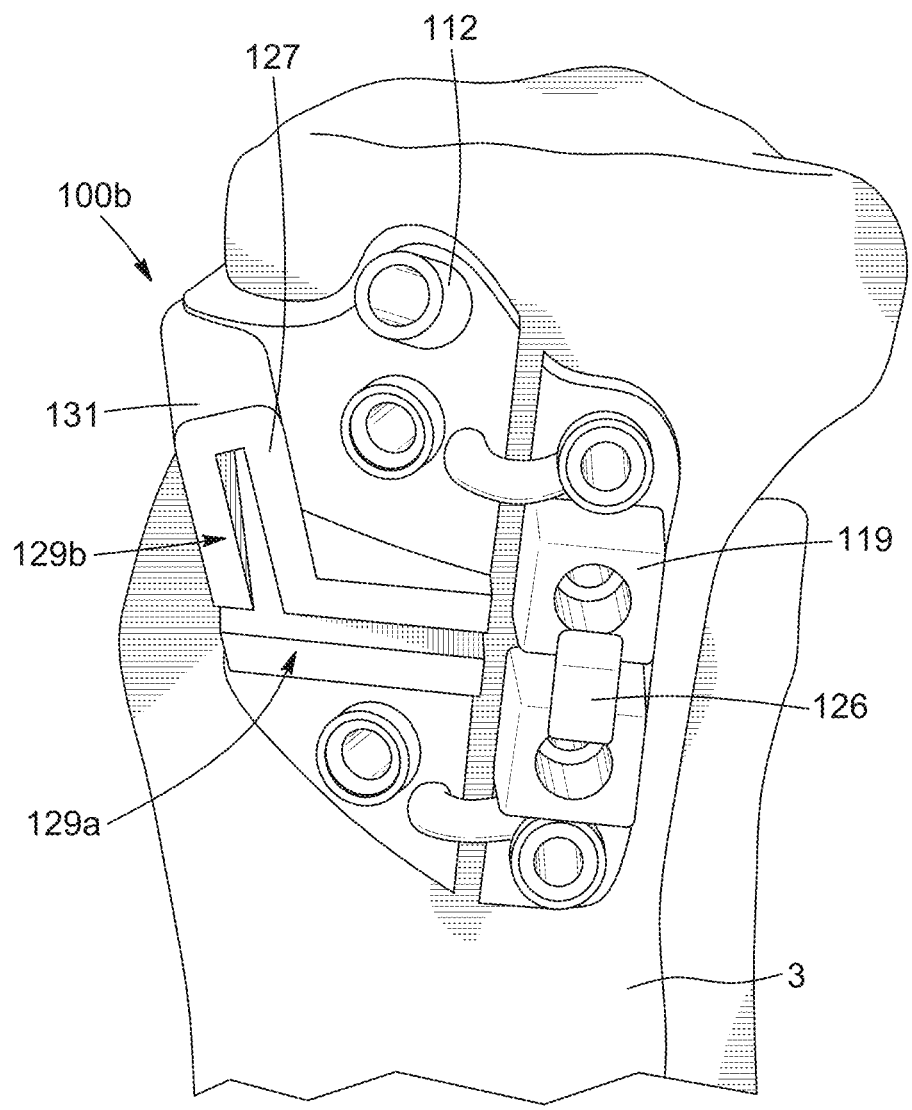
FIG. 12A is a perspective view of a surgical guide secured to the patient's tibia bone, according to an alternate embodiment in which the osteotome guide is configured to form a biplanar cut in the patient's bone.
Figure 12B:
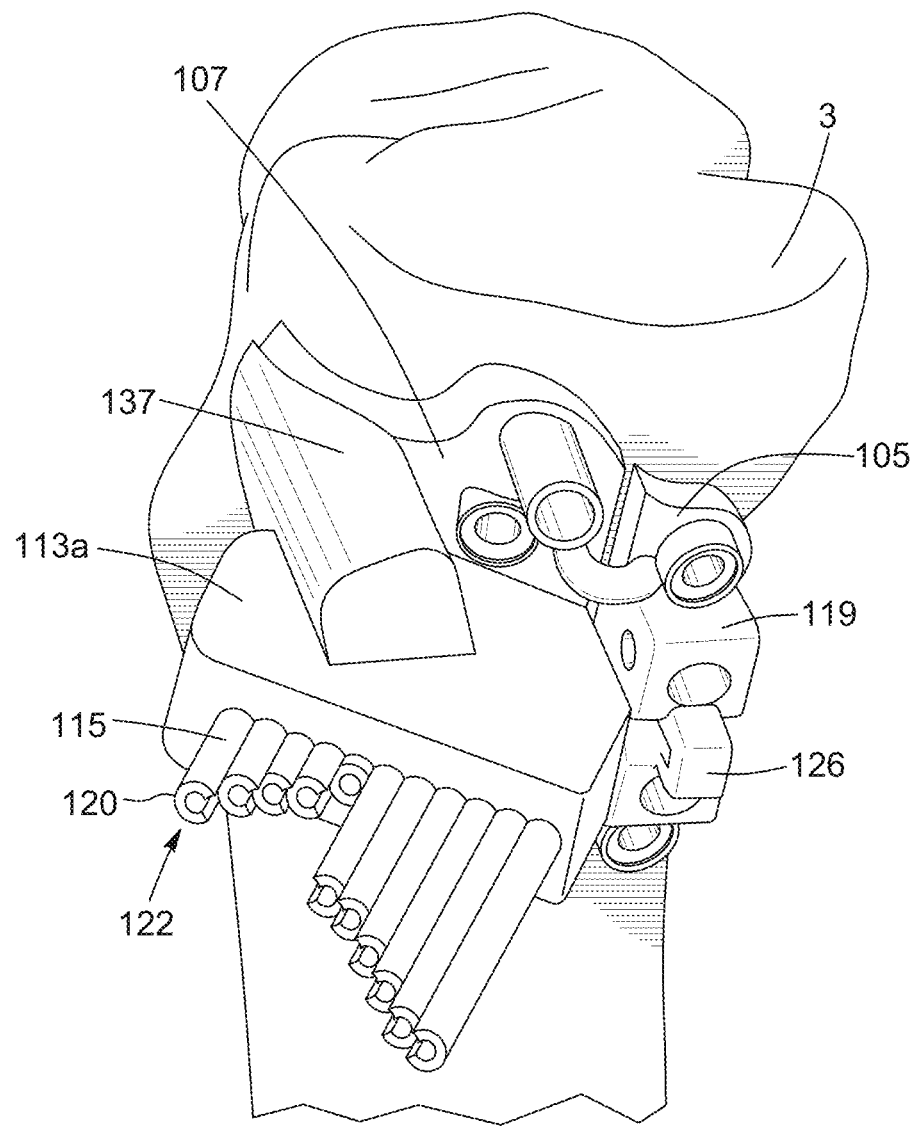
FIG. 12B is a perspective view of the surgical guide of FIG. 12A, including a first removable drilling module secured thereto via the osteotome guide, the first removable drilling module being configured to drill along a first plane.
Figure 12C:
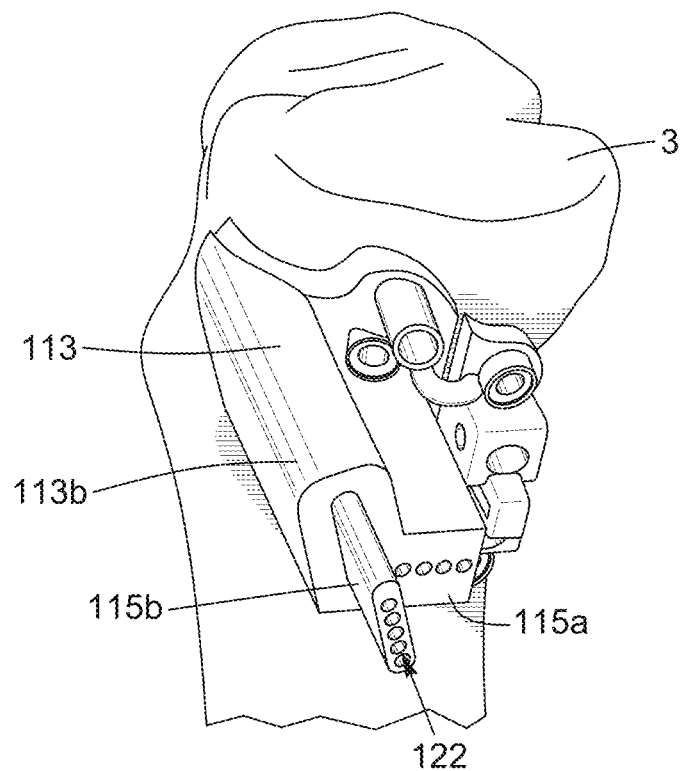
FIG. 12C is a perspective view of the surgical guide of FIG. 12A, including a second removable drilling module secured thereto via the osteotome guide, the second removable drilling module being configured to drill along the first plane and a second plane.

Finally, although in the presently described embodiments the drilling module 113 is configured to guide drill holes 116 in a common plane 133, it is appreciated that in other embodiments, the drilling module can be configured to guide drill holes 116 into two or more planes depending on the requirements of the surgical procedure. For example, with reference to FIGS. 12A, 12C, and 12D drilling module 113 can comprise a first group of parallel drill guides 115a for creating drill holes 116 in a first plane 133, and a second group of parallel drill guides 115b for creating drill holes 116 in a second plane 135. As can be appreciated, the first plane 133 is not parallel to second plane 135 and is substantially perpendicular thereto, allowing to weaken the bone 3 to eventually form a biplanar cut 5a, 5b therein.

As can be appreciated, in some embodiments, a single drilling module 113 can be configured to create all the necessary drill holes to weaken the bone 3 in planes 133, 135 in preparation for forming biplanar cuts 5a, 5b. However, in other embodiments, two or more drilling modules 113 can be provided to create the necessary drill holes in planes 133, 135 in phases. For example, in the embodiment shown in FIGS. 12A, 12B, 12C, and 12D, two drilling modules 113a and 113b are provided. A first drilling module 113a can be secured to drilling module interface 131 to create drill holes 116 in the first plane 133 in a first parallel orientation 133a. The drilling module 113a includes a cover element 137 for covering openings in the drilling module interface 131 extending along the direction of the second plane 135. Once the drill holes have been formed in the first plane 133, the drilling module 113a can be removed, and a second drilling module 113b can be secured to the drilling module interface 131. The second drilling module 113b is provided with a first group of drill guides 115a for drilling holes 116 in the first plane 133 in a second parallel orientation 133b different from the first parallel orientation 133a, thereby completing the required weakening of the bone in the first plane 133. The second drilling module 113b is further provided with a second group of drill guides 115b for drilling holes 116 in the second plane 135. In the present embodiment, the second group of drill guides 115b in the second drilling module 113b are sufficient to weaken the bone to form the second planar cut 5b. It is appreciated, however, that in other embodiments, further drill guides can be provided to cut in the second plane 135 in different parallel orientations.

Although in the embodiment described above, modules 113a and 113b are described as "first" and "second" modules, it is appreciated that their order of use can be inversed depending on the requirements of the surgical procedure. Moreover, although two modules were described, it is appreciated that in other embodiments, subsequent modules can be provided to further weaken the bone via drill holes 116 in different parallel orientations and/or in different planes as required. Moreover, in some embodiments, a cover element can be provided to cover opening in the drilling module interface 131 extending along the direction of the first plane 133, for example in a drilling module configured to drill holes only in the second plane 135.

Cutting Module

Referring back to FIGS. 1A and 1B, a cutting module 117 is provided to assist in cutting the patient's bone 3. In the present embodiment, the cutting module 117 comprises an osteotome guide 127 for guiding a corresponding osteotome to cut the patient's bone 3 at predetermined position, orientation and depth. The guide 127 is configured to guide osteotome to create a planar cut in the patient's bone 3 in the area weakened by the drill holes 116 formed using the drilling module 113. The cutting module 117 is provided in anterior section 107 of guide 100, and is affixed directly to the patient's bone via fasteners 109. It is appreciated, however, that in other embodiments, the cutting module 117 can be removably attached to the lateral 105 and/or anterior 107 sections of the surgical guide 100.

Although in the present embodiment a single cutting module 117 is shown, it is appreciated that two or more cutting modules can be provided in other embodiments. For example, in some embodiments, two or more cutting modules can be provided to help create a single planar cut in two or more stages. In some embodiments, a first cutting module can be configured to create a first planar cut in a first direction, and a second cutting module can be configured to create a second planar cut in a second direction. The cutting modules can be permanently or removably affixed relative to the same area of the patient's bone 3, and/or can be removably or permanently affixed relative to different areas of the patient's bone 3, for example to access the bone 3 from different positions.

The osteotome guide 127 comprises a body extending between a bone-contacting end on the bone interface side 101 of surgical guide 100, and a terminal end on operative side 103 of surgical guide 100. The body has a planar aperture or slot 129 extending therethrough and opening on the bone-contacting end and the terminal end. The slot 129 is sized and shaped to receive a corresponding osteotome therein, and to guide the osteotome to cut the patient's bone 3 at a position, angle, and depth corresponding to the area of the patient's bone 3 weakened by the drilling module 113. More specifically, osteotome can slide in and out of slot 129, while sidewalls around the aperture constrict the movement of osteotome to the correct position and angle to form the desired cut. Similarly, an abutting member of osteotome is configured to abut against terminal end of the osteotome guide 127 to limit an insertion depth of the osteotome. As can be appreciated, osteotome guide 127 can have visual indications provided thereon to further help guide osteotome visually and/or to indicate a type of osteotome to be used with guide 127.

In the present embodiment, in order to guide the osteotome to cut the area of the patient's bone 3 weakened by drilling module 113, the osteotome guide 127 is positioned in alignment with the drill guides 115. More specifically, the cutting module 117 is positioned adjacent the patient's bone 3, and the drilling module 113 is positioned adjacent the cutting module 117, such that the drill guides 115 open in alignment with the slot 129 in the osteotome guide 127. In this configuration, drill guides 115 guide drill bits 200 through the slot 129 in osteotome guide 127 before entering the patient's bone 3, thereby assuring that drill bits 200 and osteotome operate in the same plane 133. In the present configuration, cutting module 117 is affixed directly to patient's bone 3, while drilling module 113 is removably attached to cutting module 117. Drilling module 113 can thus be removed after drill holes 116 have been formed, providing the osteotome with direct access to cutting module 117. It is appreciated that other configuration are possible which can still allow brill bits 200 and osteotome to operate in the same plane. For example, in some embodiments, both drilling module 113 and cutting module 117 can be removably attachable to surgical guide 100. Drilling module 113 can be attached first to created drill holes 116. Drilling module 113 can be subsequently removed, and cutting module 117 can be attached to the same are of guide 100 as drilling module 113, allowing cutting module 117 to guide the osteotome in the same plane as the drill holes 116.

Figure 12D:
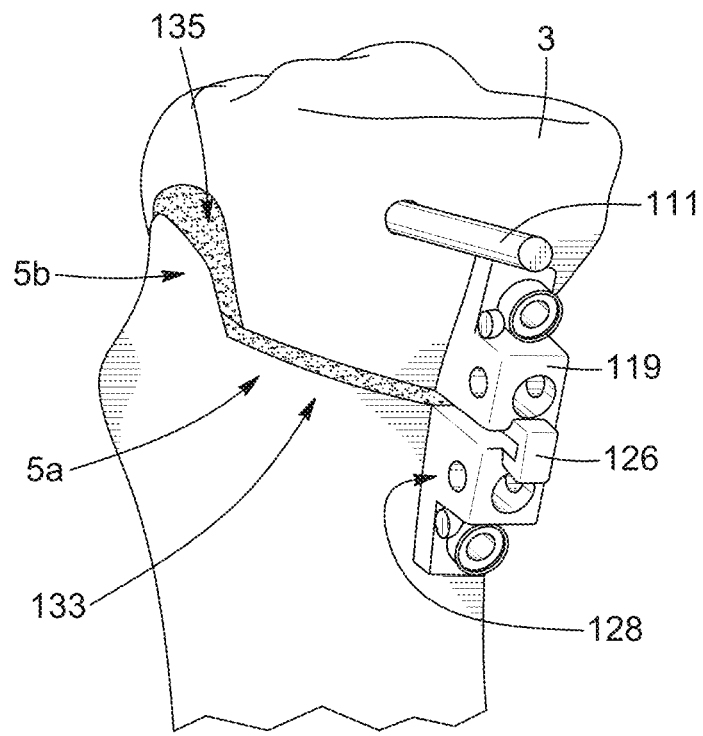
FIG. 12D is a perspective view of the patient's tibia bone with the anterior section of surgical guide of FIG. 12A removed, showing the biplanar cut formed in the patient's tibia bone.

In the present embodiment, the cutting module 117 is configured to guide osteotome to create a single planar cut 5 in the patient's bone 3, however it is appreciated that in other embodiment, the guide can be configured to create two or more cuts and/or cuts having a contour or curve. For example, with reference to FIGS. 12A and 12C, surgical guide 100b comprises an osteotome guide 127 configured with first 129a and second 129b slots for guiding osteotome to cut the patient's bone to create two planar cuts 5a and 5b along two different planes 133, 135. As can be appreciated, although two slots 129a and 129b are provided, use of the second slot 129b can be optional, allowing the same guide 100b to be compatible with both procedures involving single planar cuts 5 and biplanar cuts 5a, 5b. For example, as shown in FIG. 12D, a drilling module 113a can be provided which includes drill guides 115 in only the first plane 133, whereas a cover element 137 covers the slots 129b in the second plane 135. In this fashion, the bone is only weakened along the first plane 133, and cut 5a can be formed in said plane. Additionally or alternatively, when manufactured for such procedures, the slot 129b in guide 100b can be covered to prevent an osteotome from being inserted therein. As can be appreciated, the guide 100b can still include the section of tongue of drill module interface 131 which extends along the plane where slot 129b once extended. In this fashion, the shape of drilling module interface 131 can be the same regardless of whether or not a second plane is to be cut. This can allow for the same general shape/configuration of surgical guide 100b to be used for different types of surgical procedures involving single or biplanar cuts, and similarly allows for the same general shape/configuration of drill modules 113 to be used. This can simplify the manufacturing and design of surgical guide 100 and corresponding modules, as the same shape can be used for all procedures types, yet simply adapted to conform the anatomy of the patient's bone 3.

Anchor Module

Figure 3A:
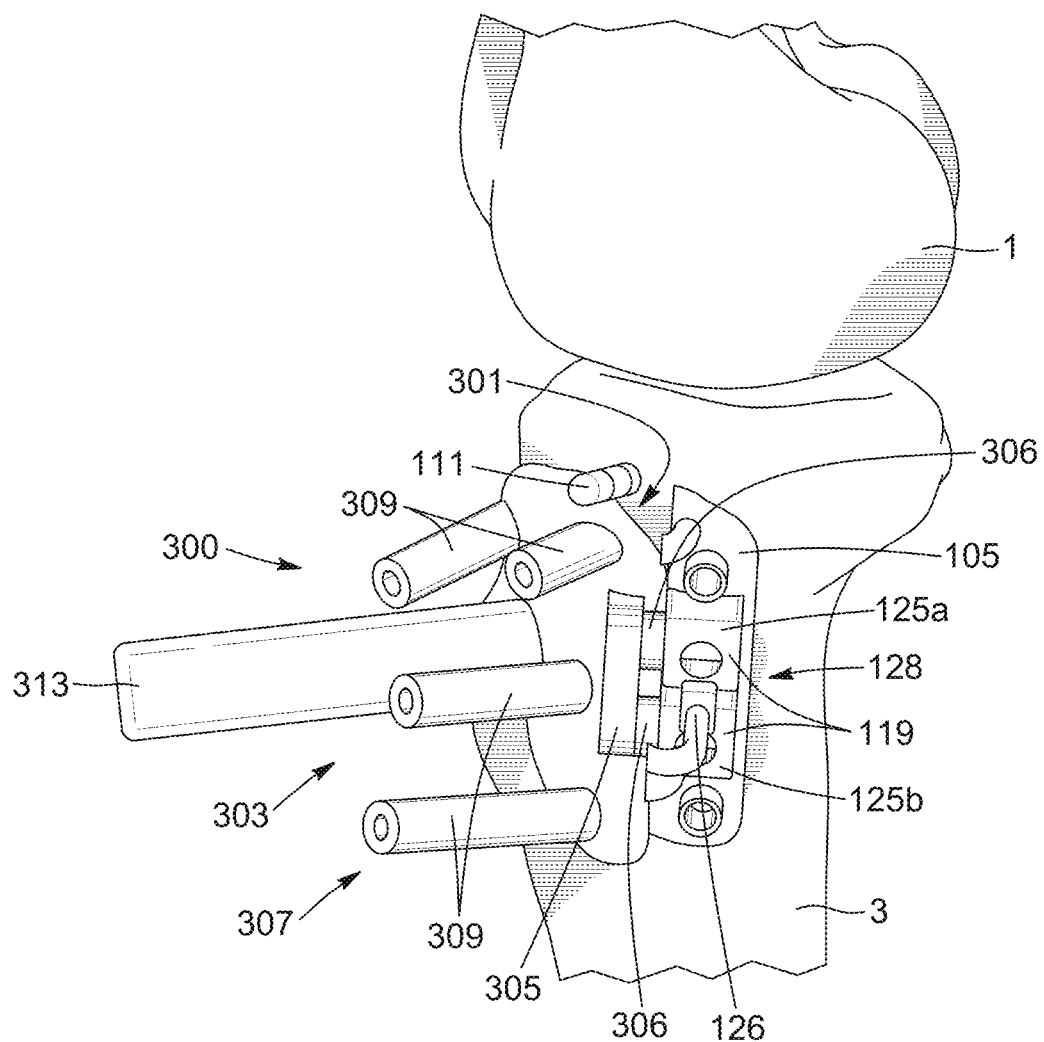
FIGS. 3A and 3B are respectively medial and anterior perspective views of a predrilling module secured to an anchor module on the patient's tibia bone, according to an embodiment.

With reference now to FIG. 3A, an anchor module 119 is provided to anchor removable modules relative to the patient's bone 3. In the present embodiment, anchor module 119 is provided in the lateral section 105 of the surgical guide 100, but it is appreciated that in other embodiments, anchor module 119 can be provided in a different section of guide 100. Moreover, in some embodiments, a plurality of anchor modules can be provided. The anchor module 119 is affixed directly to the patient's bone 3 via fasteners 109 and comprises a removable module interface 128 for interfacing with removable modules. The anchor module can thus act as a secure base to which other modules can be removably attached, allowing the removable modules to be properly aligned relative to the patient's bone 3 at relevant steps during the surgical procedure. In the present embodiment, the removable module interface 128 comprises apertures for receiving corresponding protrusions extending from a removable module, although it is appreciated that other removable connection interfaces are possible.

In the present embodiment, the anchor module 119 comprises two sections for providing two distinct anchoring points. More specifically, the anchor module 119 comprises a proximal section 125a positioned proximate the joint between the patient's femur 1 and tibia 3 bones, and a distal section 125b spaced further away from the joint between the femur 1 and tibia 3. The proximal 125a and distal 125b sections are separable from one another, allowing them to move independently while being secured to different sections of the patient's bone 3. In the present embodiment, proximal 125a and distal 125b sections are secured to one another via connecting member 126. The connecting member 126 can be severed to separate proximal 125a and distal 125b sections and allow them to move independently with different sections of bone. For example, in the present embodiment, proximal 125a and distal 125b sections are positioned on the patient's bone 3 on opposite sides of the planar cut formed by drilling module 113 and cutting module 117. After the planar cut is formed, connecting member 126 can be severed to separate proximal 125a and distal 125b sections. The bone 3 can be opened along the planar cut, with the proximal 125a and distal 125b sections moving away from one another while being respectively connected to the bone 3 above and below the opening formed in the bone 3. In this fashion, the proximal section 125a can provide an anchoring point above or proximal the opening in the bone 3, while the distal section 125b provides an anchoring point below or distal the opening in the bone 3. It is appreciated that other positions and configurations of anchor module 119 and corresponding sections are possible, depending on the surgical procedure. It is further appreciated that the separable sections of anchor module 119 can be connected to one another via different removable connection mechanisms.

Predrilling Module

Figure 3B:
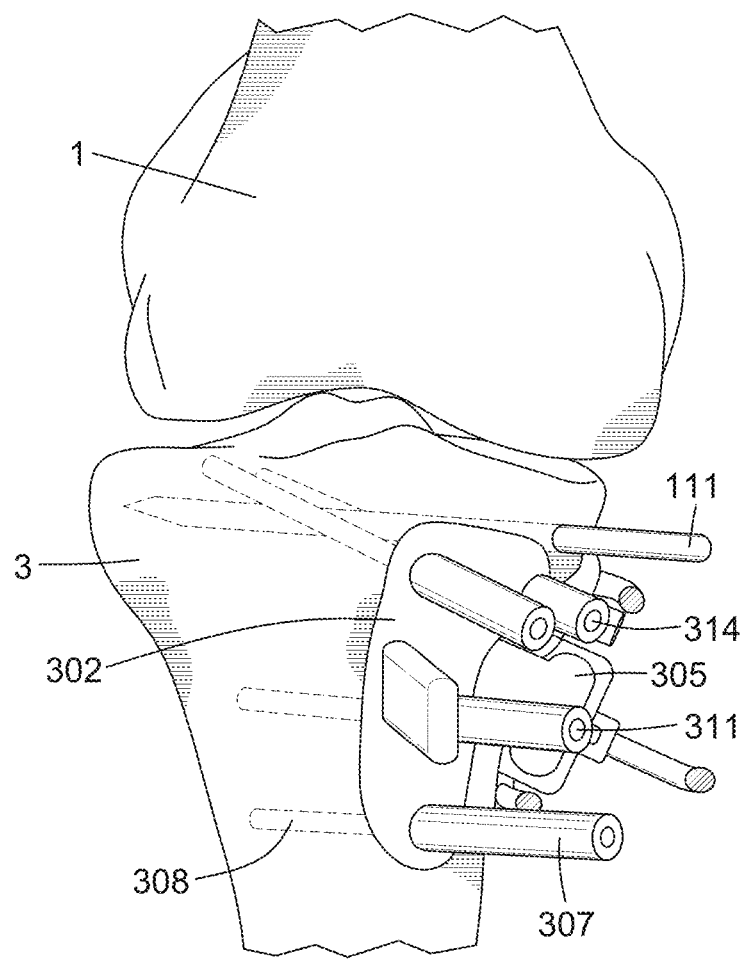

With reference to FIGS. 3A and 3B, a predrilling module 300 is provided for predrilling holes in the patient's bone 3 for eventually receiving fasteners to secure a plate or other implant to the patient's bone 3. The predrilling module 300 is patient-specific in that it is custom made according to the anatomy of the patient's bone 3 and according to a preoperative plan. In this fashion, the predrilling module 300 can be configured to precisely fit on a predetermined position of the patient's bone 3 to assure proper alignment, and to assist in drilling holes in the patient's bone 3 in predetermined positions, orientations and depths.

In the illustrated embodiment, the predrilling module 300 comprises a body 302 having a bone interface side 301 and an operative side 303. The bone interface side 301 comprises a bone-contacting surface having contours complementary in shape to the surface contours of the patient's bone 3. In this configuration, bone interface side 301 can abut against the patient's bone 3, and key into a specific position thereon. In the present embodiment, bone interface side 301 comprises a solid surface, however it is appreciated that other configurations are possible. For example, the surface can be defined by an open lattice, and can comprise edges conforming to the contours of the patient's bone 3.

The operative side 303 is provided opposite the bone interface side 301 and comprises a plurality of drill guides 307 extending therefrom for guiding corresponding drill bits. In the present embodiment, the drill guides 307 each comprise a guide barrel 309 extending from the body of the predrilling module 303 at a predetermined angle along a lengthwise axis and terminating at a terminal end 314. The guide barrel 309 comprises sidewalls defining a hollow interior in the form of a guide tunnel 311 extending through the guide barrel 309 along the lengthwise axis thereof and opening on the bone interface side 301 and operative side 303 of predrilling module 303. The guide tunnels 311 are sized and shaped to receive a corresponding drill bit therein, allowing the drill bit to slide in and out of barrel 309, while sidewalls of barrel 309 constrain movement of the drill bit to a predetermined depth, position, and orientation relative to the patient's bone 3. An abutting member on the drill bit can limit an insertion depth of an operative end of the drill bit into the barrel 309 as it abuts with terminal end 314 of guide barrel 309. As can be appreciated, in this configuration, the length of barrel 309 can limit insertion depth of a drill bit and assure the depth of drill holes formed therewith.

The plurality of drill guides 307 are configured to cooperate with a calibrated drill bit having a fixed operative length. The guide barrels 309 of the drill guides 307 are sized, positioned and oriented to create drill holes 308 in a predefined pattern for receiving fasteners to secure an implant, such as plate, to the patient's bone 3. As will be described in more detail hereinafter, the implant to be secured can be patient-specific and can be designed to be affixed using different types of fasteners. Based on the anatomy of the patient's bone 3, a preoperative plan can define a configuration of fasteners, including size, depth, orientation, and position, such that the implant can be affixed optimally. The drill guides 307 can thus be configured to guide drill bits to form drill holes 308 in preparation for receiving the configuration of fasteners defined in the preoperative plan. For example, the length of each guide barrel 309 can be adjusted to limit the insertion depth of the drill bit, creating drill holes 308 with different predetermined depths. Similarly, the position an orientation of guide barrels 309 can be adjusted to define drill holes 308 which extend at different angles and positions. Finally, diameters of guide tunnels 311 can be adjusted to accommodate drill bits of different diameters to create drill holes of different sized for accommodating different sizes of fasteners.

In the present embodiment, the predrilling module 300 is configured to predrill holes 308 in the patient's bone 3 prior to a surgical alteration of the bone's geometry. The predrilling module 300 is thus configured to account for the drill holes 308 moving as the geometry of the bone is altered during surgery, such that the drill holes 308 will be in alignment with the fasteners of an implant once the bone alterations are complete. For example, in the context of a high-tibial open-wedge osteotomy procedure, the predrilling module 300 can be configured to predrill holes while the patient's bone 3 is in a closed configuration (i.e. before the patient's bone 3 is opened along the planar cut formed using the drilling 113 and cutting 117 modules). In this configuration, the guide barrels 309 are positioned to form drill holes 308 which will eventually align with the location of fasteners for affixing an implant once the patient's bone 3 is opened along the planar cut to an opened configuration. As can be appreciated, the required position of drill holes 308 can be determined by modelling the patient's bone 3, virtually opening the bone model to a desired opening angle, and virtually positioning an implant and corresponding fasteners on the bone model to set final positions of the drill holes 308. The bone model can be subsequently closed virtually to determine corresponding initial positions of the drill holes 308. The predrilling module 300 can then be designed according to the initial positions of the drill holes 308.

As shown in FIGS. 3A and 3B, predrilling module 300 comprises an attachment/alignment mechanism 305 for securing the predrilling module 300 relative to the patient's bone 3 and/or for assuring proper alignment of the predrilling module 300 relative to the patient's bone 3. In the present embodiment, the attachment/alignment mechanism 305 comprises an attachment interface for interfacing with removable module interface 128 in anchor module 119. The attachment/alignment mechanisms 305 is configured such that the predrilling module 300 can attach to anchor module 119 in only one position/orientation, thus assuring that predrilling module 300 is properly aligned once it is attached to anchor module 119. For example, in the present embodiment, the attachment interface comprises two protrusions or pins 306 sized and shaped to engage in corresponding apertures in anchor module 119. The protrusions 306 provide two fixed attachment points which must be respectively align with two fixed anchoring points in the anchor module 119 for the predrilling module 300 to engage with anchor module 119. In the present embodiment, the protrusions 306 are positioned to align with anchor module 119 while the patient's bone 3 is in a closed configuration, thereby allowing the predrilling module 300 to engage with the patient's bone 3 and predrill holes 308 prior to opening the bone 3 (i.e. the protrusions 306 respectively align with the proximal 125a and distal 125b sections while they are adjacent one another). It is appreciated that in other embodiments, the protrusions 306 can be positioned to align with the anchor module 119 when the patient's bone is in the opened configurations (i.e. when the proximal 125a and distal 125b sections are space apart from one another across the opening in the patient's bone 3).

Although in the present embodiment a single mechanism 305 provides both the functions of securing and aligning predrilling module 300 relative to the patient's bone 3, it is appreciated that in other embodiments, different mechanisms can be provided to align and/or to secure predrilling module 300, and that separate mechanisms can be provided to respectively perform the alignment or attachment functions. For example, in some embodiments, predrilling module 300 can be secured to the patient's bone directly via fasteners. In some embodiments, the bone interface side 301 of predrilling module 300 can be shaped to have contours complementary in shape to the contours of a specific area of the patient's bone 3. In some embodiments, mechanism 305 can comprise a member configured to interface and/or insert into a hole or other feature formed in the patient's bone 3, for example in the opening formed along the planar cut.

The predrilling module 300 further comprises a handle member 313 which allows the module 300 to be more easily manipulated and positioned. In the present embodiment, the handle member 313 is a rigid elongated member extending from the body of the predrilling module 300 along a lengthwise axis and facilitates manipulation of the module 300 by hand. It is appreciated that in other embodiments, different types of handle members can be provided. For example, handle member can be removable and/or can comprise an interface for a positioning tool or guide. In the present embodiment, the handle member 313 has inscriptions provided thereon to identify the predrilling module 300 and/or to indicate the type of drill bits with which the predrilling module 300 is designed to cooperate.

Figure 13:
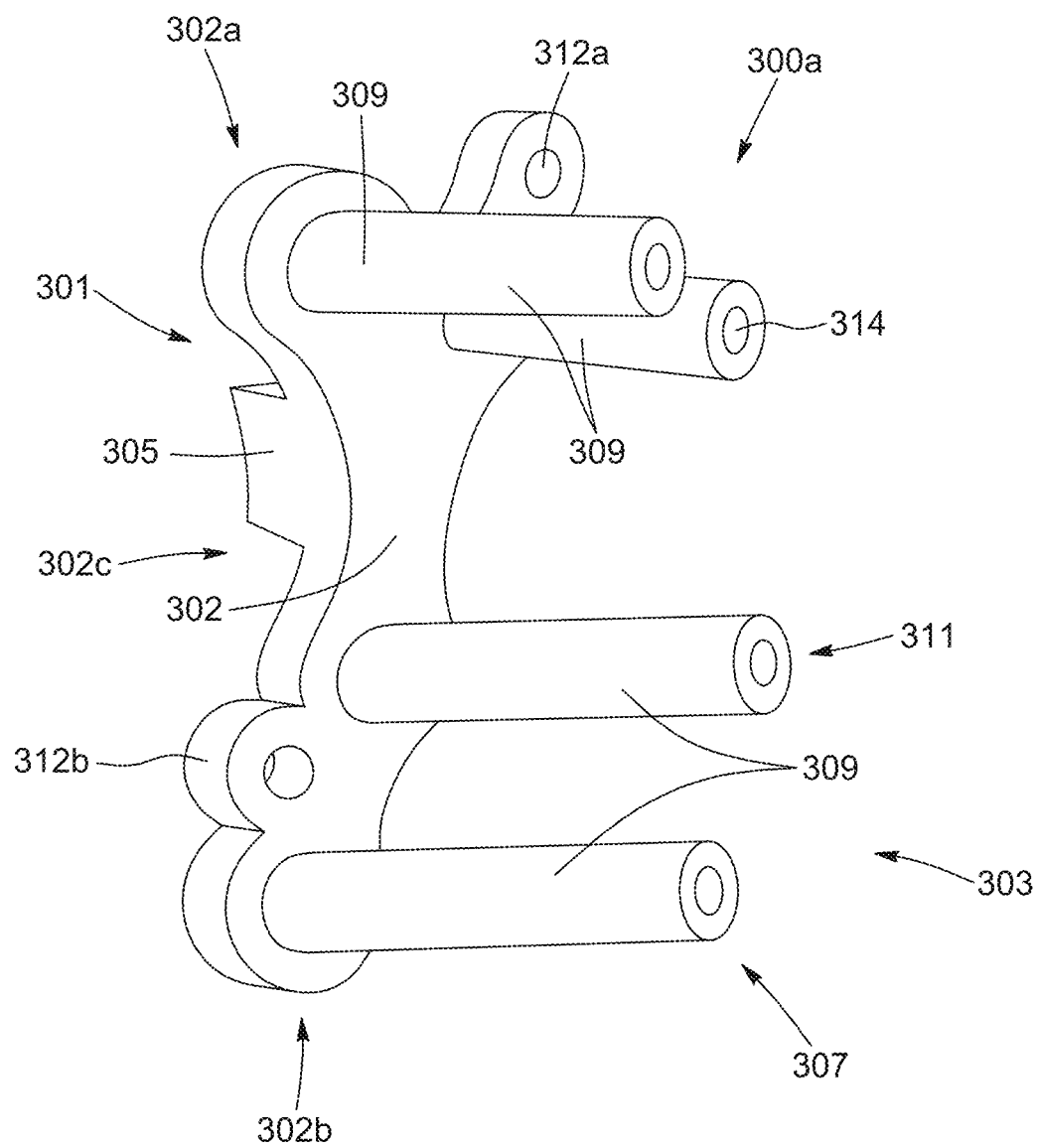
FIG. 13 is a perspective view of a predrilling module, according to an alternate embodiment in which the predrilling module is configured to drill holes for the fixation plate after an open wedge has been formed in the patient's bone.

Although in the illustrated embodiment the predrilling module 300 is configured to drill holes 308 prior to a change in the geometry of the patient's bone 3, it is appreciated that the predrilling module 300 can be configured differently according to the requirements of the surgical procedure. For example, as shown in FIG. 13, an embodiment of a predrilling module 300a is shown in which the module 300a is configured to drill holes 308 after the geometry of the patient's bone 3 has been surgically altered. In this embodiment, the predrilling module 300a is configured to span across opening 7 formed in the patient's bone 3, and position drill guides 307 to define drill holes 308 directly in their final position. More specifically, the predrilling module 300a has a body 302 substantially similar to a fixation plate which will ultimately be used to secure the opening 7 in the patient's bone 3. The bone 3 can thus be opened along planar cut 5 to form opening 7, and once the opening 7 is formed, the predrilling module 300 can be secured to the bone at the same position where the fixation plate will eventually be attached. The predrilling module 300 will thus have its drill guides 307 positioned exactly where the fastener apertures of fixation plate will eventually be positioned. Therefore, after drill holes 308 are formed, predrilling module 300 can be removed and replaced with fixation plate. Fixation plate can be positioned to align with the holes 308 and then secured in place via fasteners.

In the present embodiment, the body 302 of predrilling module 300 has a bone interface side 301 having a bone-contacting surface substantially conforming to a surface contour of the patient's bone 3 at a predetermined position. The body 302 is configured with a proximal section 302a for positioning adjacent a surface of the patient's bone 3 above opening 7, a distal section 302b for positioning adjacent a surface of the patient's bone 3 below opening 7, and an intermediate section 302c for spanning the opening 7. The attachment/alignment mechanism 305 comprises a wedge extending from bone interface side 301 on the intermediate section 302c of body 302, and configured to be inserted into the opening 7. As can be appreciated, wedge 305 can be sized and shaped according to the expected dimensions of the desired opening 7 according to a preoperative plan. It can further comprise contours matching inner surface contours of the opening 7, as will be described in more detail below in connection with the opening validator. The wedge 305 can thus allow predrilling module 300 to secure at a predetermined position relative to opening 7, while also validating that the bone 3 has been opened to the correct angle. Once module 300 has been correctly positioned, it can be secured in place relative to the patient's bone 3 before drilling is performed through drill guides 307. In the present embodiment, the body 302 comprises fastener apertures 312a, 312b in the proximal 302a and distal 302b sections to allow the body 302 to be secured directly to the patient's bone 3 via fasteners. It is appreciated, however, that other attachment mechanism are possible. For example, the module 300 could secure to an anchor module already attached to the patient's bone 3 at the correct position.

Spreader Module

Figure 4:
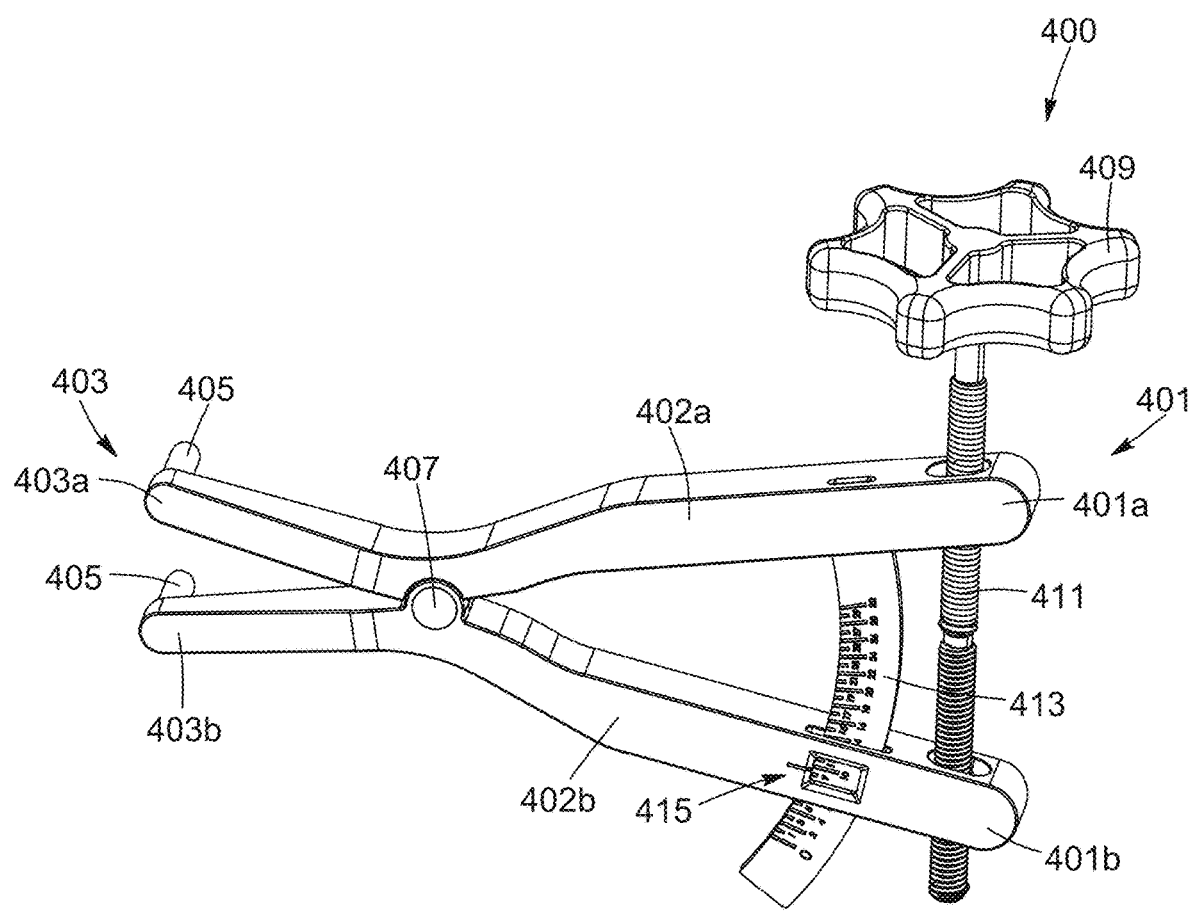
FIG. 4 is a perspective view of a spreading module, according to an embodiment.
Figure 4A:
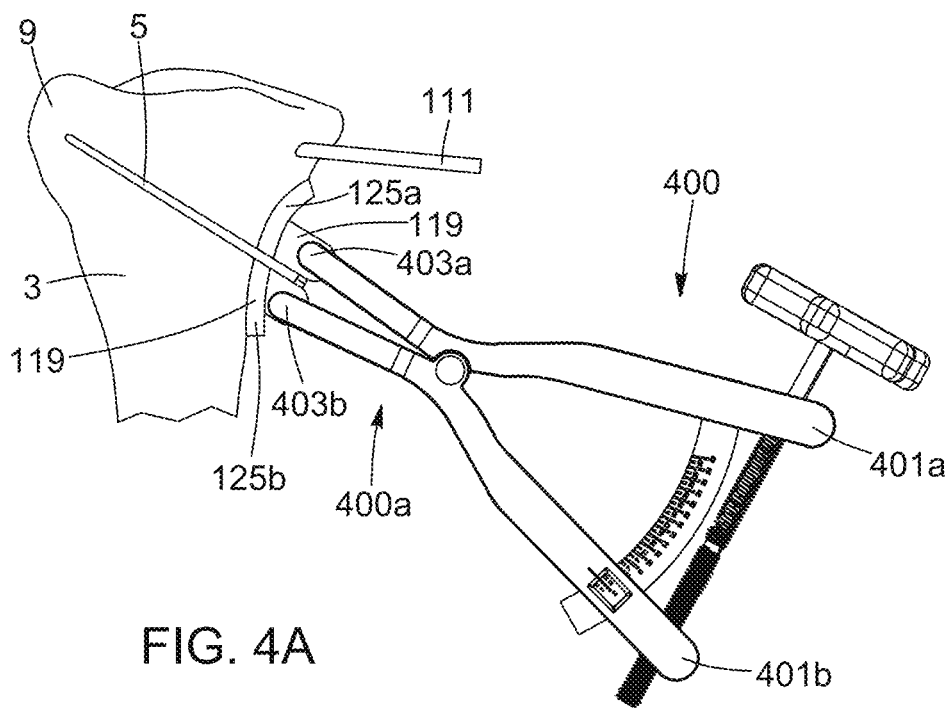
FIGS. 4A and 4B are side views showing operation of a spreading module respectively in a closed configuration and an open configuration.
Figure 4B:
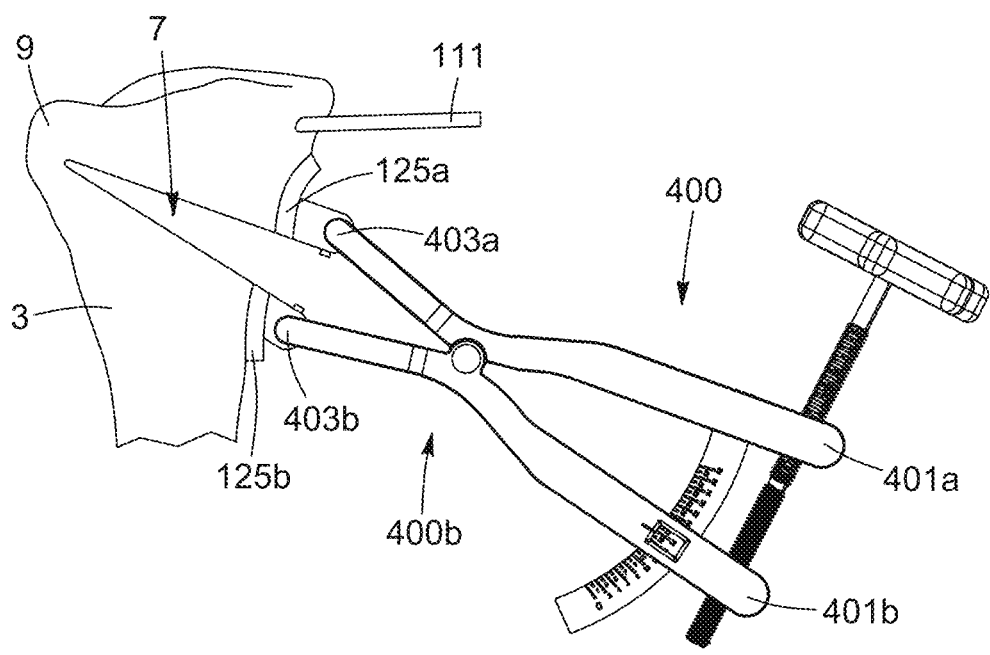

With reference now to FIGS. 4, 4A and 4B, a spreader module 400 (or spreading tool) to assist in spreading the patient's bone 3 is shown according to an embodiment. In the present embodiment, the spreader module 400 is configured to open the patient's bone 3 along a planar cut 5 formed therein. The planar cut 5 is opened at an angle about a hinge 9, thereby defining an open wedge 7 in the patient's bone. The spreader module 400 is configured to operate in cooperation with anchor module 119 secured to the patient's bone 3, but it is appreciated that other configurations are possible. As can be appreciated, the spreader module 400 can be a generic tool, and need not be custom made according to the patient. Instead, the surgical guide 100 can be designed to cooperate with generic spreader module 400. Accordingly, spreader module 400 can be made out of any rigid material, according to any manufacturing process.

However, it is appreciated that in some embodiments, the spreader module 400 can be custom designed for the patient and to conform to a specific geometry of the guide 100. In such embodiments, the spreader module 400 can be made from materials suitable for custom manufacturing, for example from the same 3D printed plastic from which the surgical guide 100 and corresponding modules are made.

In the present, spreader module 400 comprises an upper arm 402a and a lower arm 402b pivotally connected to one another via a hinge 407. As can be appreciated, spreader module 400 is generally configured as a double lever, with an effort end 401 and a load end 403, and hinge 407 acting as a fulcrum therebetween. More specifically, as effort ends 401a, 401b of upper and lower arms 402a, 402b are moved towards one another, upper and lower arms 402a, 402b pivot about hinge 407 causing load ends 403a, 403b to move away from one another. In other words, a force applied at effort end 401 causing ends 401a and 401b to converge is transferred to load end 403, causing load ends 403a and 403b to separate. It is appreciated that other configurations of spreader module 400 are possible, so long as it permits a separating force to be applied to load ends 403a and 403b. For example, in some embodiments, the spreader module 400 can be configured such that a spreading of effort ends 401a, 401b transfers a spreading force to load ends 403a, 403b. In other embodiments, different types of spreading mechanisms are possible.

In the present embodiment, force on effort end 401 is applied via a hand wheel 409. As wheel 409 is operated, screw mechanism 411 rotates and engages in threaded bores in effort ends 401a, 401b, thereby drawing effort ends 401a, 401b together or spreading them apart depending on the rotating direction of screw 411. As can be appreciated, in this configuration, a rotational force applied to wheel 409 is converted into a linear force which draws effort ends 401a, 401b together or spaces them apart. Moreover, the rotational force applied to and wheel 409 merely causes a change in spacing of effort ends 401a, 401b. A constant force does not need to be applied to wheel 409 to retain effort ends 401, 401b at a fixed spacing; instead, when no force is applied, the engagement of screw mechanism 411 retains arms 402 of spreader module 400 at their current angle, retaining effort ends 401a, 401b at a fixed spacing until force is applied to wheel 409. Spacing of effort ends 401a, 401b can thus be precisely controlled by hand, via small and/or measured rotational movements of hand wheel 409. It is appreciated, however, that a force controlling spacing of effort ends 401a, 401b can be applied via different mechanisms, and that such mechanisms need not necessarily be operated by hand. For example, in some embodiments, force can be applied via hydraulics or motors, and/or can be controlled electronically.

As mentioned above, spreader module 400 is configured to cooperate with anchor module 119 secured to the patient's bone 3. Spreading module 400 comprises an anchor interface 405 at load end 403 for interfacing with anchor 119 and transferring spreading force thereto. More specifically, in the present embodiment, the anchor interface 405 comprises protrusions or pins sized and shaped to engage in corresponding apertures in anchor module 119. A protrusion or pin at load end 403a of upper arm 402a is positioned to engage with proximal section 125a of anchor module 119, whereas a protrusion or pin at load end 403b or lower arm 402b is positioned to engage with distal section 125b of anchor module. In this configuration, arms 402a, 402b of spreader module independently engage in the distinct anchoring points 125a, 125b, allowing arms 402a, 402b to apply a spreading force thereon in opposite directions, and move anchoring points 125a, 125b away from one another.

In the present embodiment, the protrusions or pins extend from arms 402a, 402b substantially perpendicular therefrom, and along an axis substantially parallel to the pivot axis of hinge 407. As can be appreciated, in this configuration, spreader module 400 can engage with anchor 119 by sliding protrusions or pins of anchor interface 405 laterally into the corresponding apertures of anchor 119. A vertical spreading force can be subsequently applied to arms 402a, 402b without causing interface 405 to disengage. In the same manner, spreader module 400 can be easily disengaged from anchor 119 by sliding the protrusions or pins out along the lateral direction. As can be further appreciated, in this configuration, spreader module 400 can engage with anchor module 119 and operate along the lateral section of the patient's bone 3, leaving anterior section of the bone 3 clear so as to not interfere with subsequent steps in the surgical procedure. Apertures in anchor module 119 open on both anterior and lateral sides thereof, allowing the spreader module 400 to engage on either the anterior or lateral side of anchor module 119 depending on the requirements of the surgical procedure. It is appreciated, however, that in other embodiments, spreader module 400 can engage on other sides of anchor module 119, such as on its front side, and/or on top/bottom sides.

In the present embodiment, pins or protrusions of anchor interface 405 are substantially cylindrical and engage in substantially circular apertures in anchor module 119. As can be appreciated, in this configuration, pins or protrusions can rotate freely inside apertures of anchor module 119, allowing relative angular displacement of ends 403a, 403b relative to anchoring points 125a, 125b while engaged therein. It is appreciated, that in other embodiments, anchor interface 405 and/or anchor module 119 can comprise different engagement mechanisms. For example, in some embodiments, anchor interface 405 can be secured to anchor module 119 via fasteners. In some embodiments, ends 403a, 403b can key into anchoring points 125a, 125b at specific relative orientations, and/or pins or protrusions can be pivotally secured to ends 403a, 403b of arms 402a, 402b.

Spreader module 400 is operable to move between a closed configuration 400a and an opened configuration 400b. In the closed configuration 400a, anchor interface 405 on load ends 403a, 403b are substantially proximate one another and aligned with anchoring points 125a, 125b prior to spreading the patient's bone 3. In the opened configuration 400b, anchor interface 405 on load ends 403a, 403b are spaced apart from one another, and load end 403a, 403b are angled relative to one another at an opening angle. In the present embodiment, a gauge 413 is provided to indicate the magnitude of opening angle. The gauge 413 comprises a scale affixed to upper arm 402a, and movable through a corresponding aperture in lower arm 402b. A window 415 in lower arm 402b provides a visual indicator for reading scale. It is appreciated, however, that other gauge mechanisms are possible to indicate the magnitude of opening angle. In the present embodiment, gauge 413 is calibrated such that scale is zeroed when the spreader module 400 is in the closed configuration 400a. The opening angle indicated by gauge 413 can thus provide an accurate and precise indication of the opening angle of spreader module 400. In some embodiments, the gauge 413 can be further calibrated such that it corresponds to the opening angle about hinge 9 in patient's bone 3. In this configuration, the gauge can provide a precise and accurate indicate of opening angle of the open wedge 7 formed in the patient's bone, as the bone is opened along cut 5 using spreader module 400.

Although the module 400 is referred to herein as a "spreader" module, it is appreciated that it can be used not only to spread the patient's bone 3, but also to contract the patient's bone 3, for example as part of a closed-wedge osteotomy. In such procedures, the spreader module 400 can be operated to draw anchoring points 125a, 125b closer together, for example to close an open wedge 7 cut into the patient's bone 3. More particularly, spreader module 400 can engage with anchoring points 125a, 125b while in the opened configuration 400b, with the anchoring points 125a, 125b being positioned on opposite sides of an open wedge 7. The spreader module 400 can be subsequently operated towards the closed configuration 400a by turning hand wheel 409, thereby drawing anchoring points 125a, 125b together and closing the wedge 7.

Opening Validator

Figure 5:
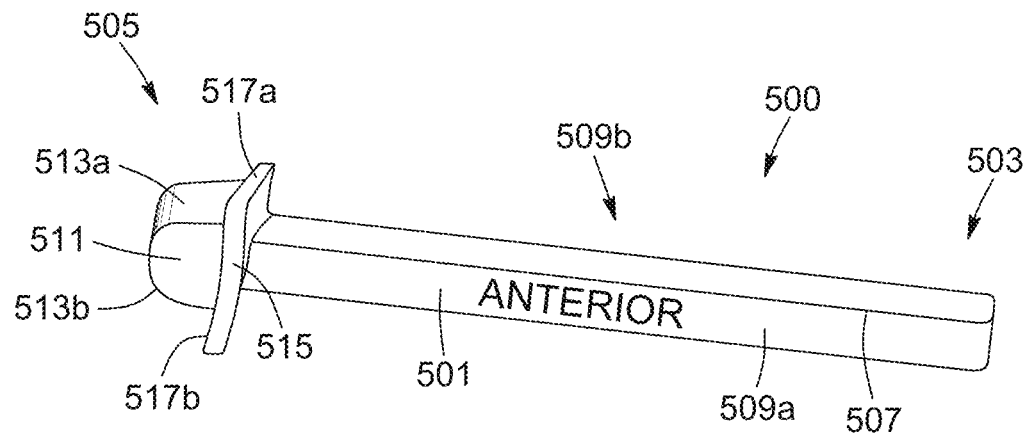
FIG. 5 is a perspective view of an opening validator, according to an embodiment.
Figure 5A:
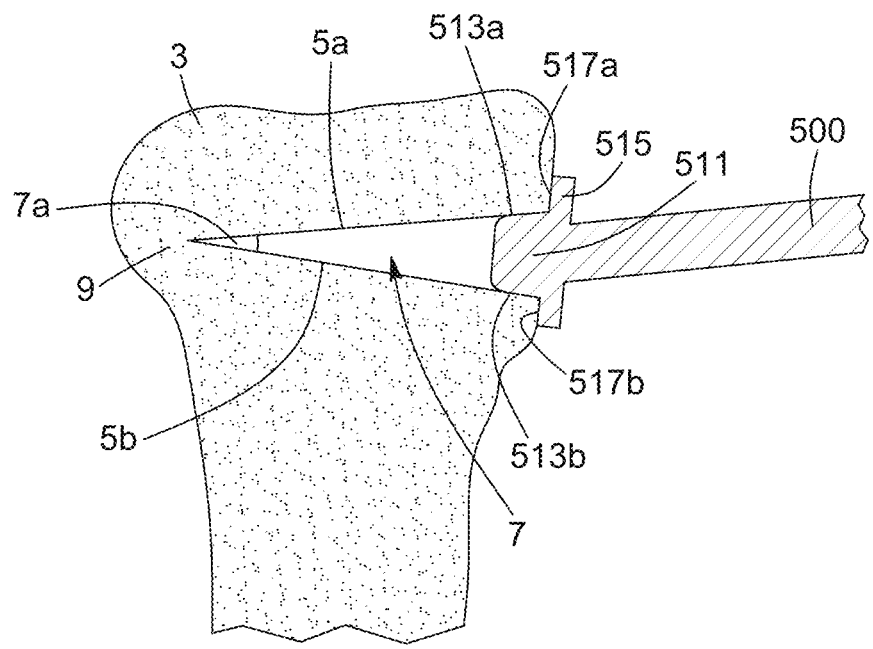
FIG. 5A is a cross sectional view showing the opening validator of FIG. 5 inserted into an open wedge formed in the patient's tibia bone.

With reference now to FIGS. 5 and 5A, an opening validator 500 for validating the open wedge 7 formed in the patient's bone 3 is shown according to an embodiment. As can be appreciated, a desired opening angle of open wedge 7 can be predetermined according to a preoperative plan. Although the gauge in spreader module 400 can provide an indication of the opening angle during the procedure, opening validator 500 can provide a more precise confirmation as to whether the patient's bone 3 has been opened the right amount to attain the desired angle of open wedge 7. Accordingly, opening validator 500 is provided to directly measure the open wedge 7 formed in the patient's bone 3.

In the present embodiment, opening validator 500 is a patient-specific tool designed to match the anatomy of the patient's bone 3. More specifically, the opening validator 500 is shaped and configured to fit snugly in the opening 7 in the patient's bone 3 based on the expected shape thereof as determined according to a pre-operative plan. During the surgical procedure, as the patient's bone 3 is being spread to form opening 7, the opening validator 500 can be inserted into the opening 7. A snug fit of opening validator 500 can confirm that the correct opening 7 has been formed, whereas an incorrect fit can indicate that an adjustment of opening 7 is necessary. It is appreciated that other mechanisms for validating the opening are also possible.

As shown in FIG. 5, the opening validator 500 comprises a unitary body 501, made from a rigid, biocompatible material. In the present embodiment, the body 501 is made from a 3D printed plastic, although it is appreciated that other materials are possible, and that the validator 500 can be made using other custom manufacturing processes. The body 501 includes a handle end 503 and an operative end 505.

Handle end 503 is configured to facilitate manipulation of opening validator 500 during the surgical procedure. In the illustrated embodiment, handle end 503 comprises a handle 507 to allow the validator 500 to be easily grasped and/or manipulated by hand. It is appreciated, however, that other interfaces for manipulating the validator 500 are also possible. In the present embodiment, the handle 507 has a substantially rectangular-shaped profile, including an anterior side 509a and a lateral side 509b. The anterior 509a and lateral 509b are marked to indicate proper orientation during the surgical procedure. It is appreciated, however, that other shapes of handle 507 are also possible.

Operative end 505 is configured to engage with the opening 7 formed in the patient's bone 3 at a predetermined position and orientation. More specifically, the operative end 505 comprises a wedge element 511 sized and shaped to fit in the opening 7, and a tab element 515 to limit the insertion depth of wedge 511. Wedge element 511 is shaped to conform to the contour of interior surfaces 5a, 5b of the patient's bone 3 formed by planar cut 5 and confirm the height of opening 7 proximate the exterior surface of bone 3, and thus confirm opening angle 7a. More specifically, wedge elements 511 comprises a top surface 513a shaped to conform to the contour of top or proximal interior surface 5a, and a bottom surface 513b shaped to conform to the contour of bottom or distal interior surface 5b. Similarly, tab element 515 is shaped to conform to the exterior contours of the patient's bone 3. More specifically, tab element 515 comprises a top surface 517a shaped to conform to the exterior contour of the patient's bone 3 above the cut 5, and a bottom surface 517b shaped to conform to the exterior contour of the patient's bone 3 below the cut 5. As show in FIG. 5A, when opening 7 in the patient's bone 3 is opened to the right angle, and when validator 500 is correctly positioned therein, top 513a and bottom 513b surfaces of wedge element 511, and top 517a and bottom 517b surfaces of tab element 515 will simultaneously conform and engage with the corresponding surfaces of the patient's bone 3, thereby locking opening validator 500 in place and confirming that configuration of opening 7 matches the pre-operative plan. Any mismatch between the surfaces of the validator 500 elements and the surfaces of the patient's bone 3 can indicate that ad adjustment is required.

Figure 13A:
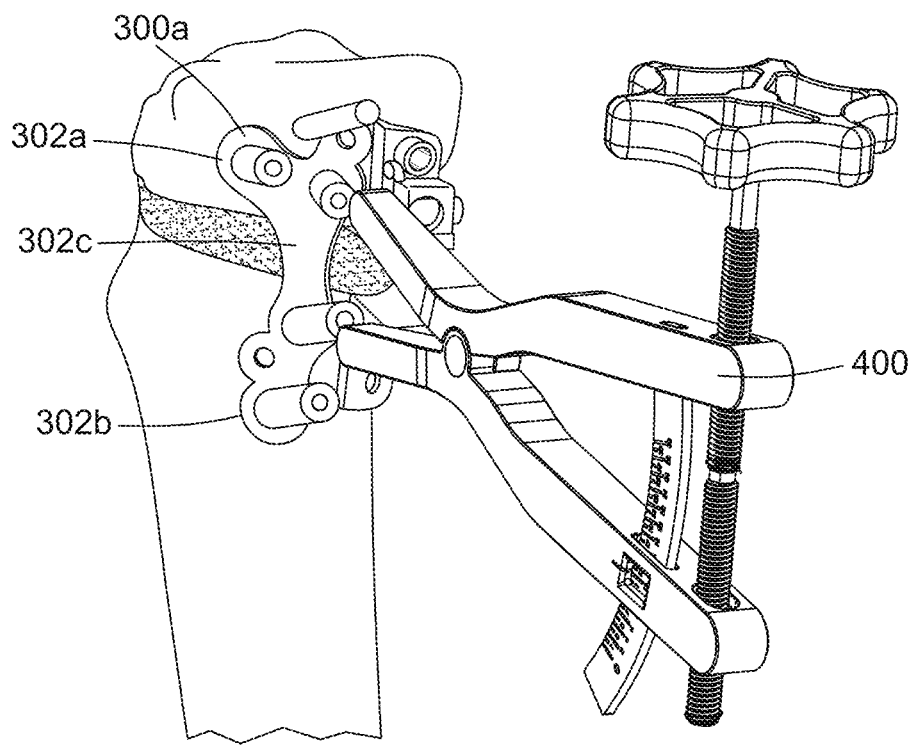
FIGS. 13A and 13B are perspective views showing positioning of the predrilling module of FIG. 13 and validating of the opening formed in the patient's bone.
Figure 13B:
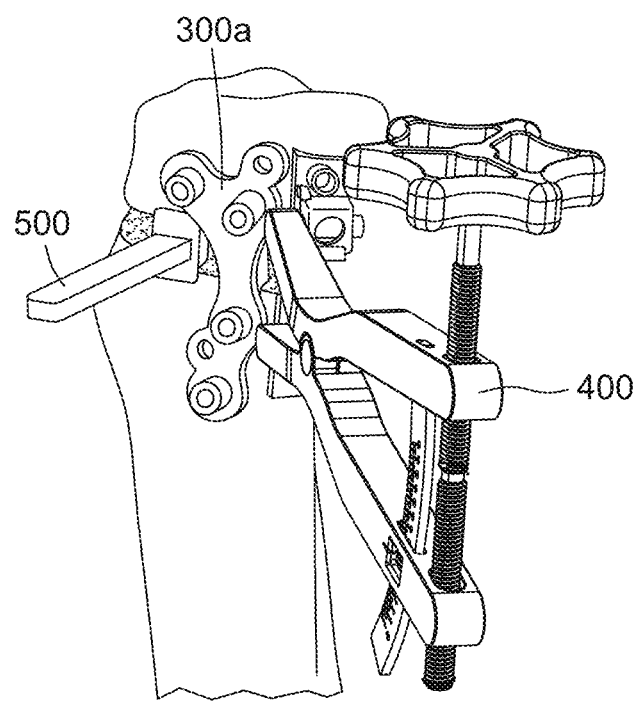
Figure 14:
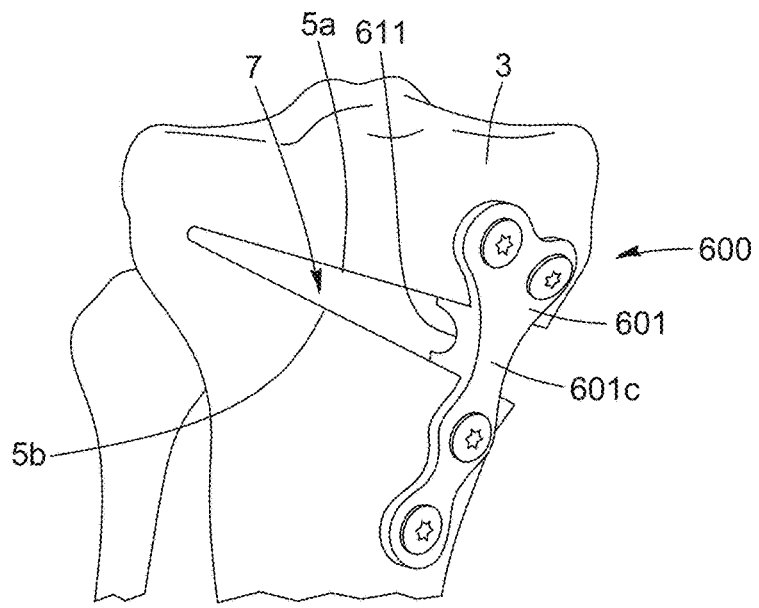
FIG. 14 is a perspective view of a fixation plate securing an open wedge formed in a patient's tibia bone, according to an embodiment in which the fixation plate is provided with a wedge element.
Figure 14A:
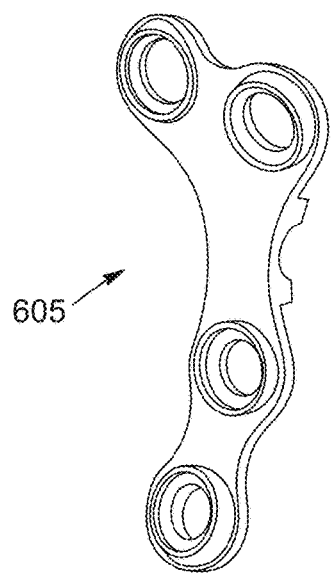
FIGS. 14A, 14B and 14C are respectively front perspective, rear perspective and side views of the fixation plate of FIG. 14.
Figure 14B:
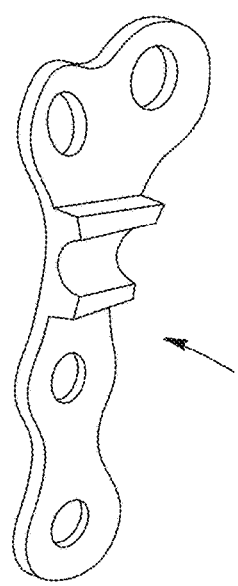
Figure 14C:
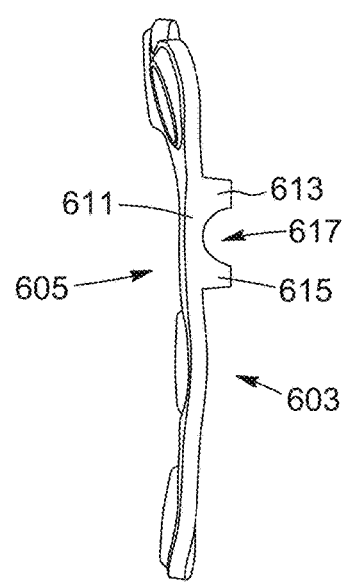

As can be appreciated, opening validator 500 can be used to assure that opening 7 in patient's bone 3 is formed correctly prior to proceeding with subsequent steps of the procedure. For example, it can confirm opening 7 prior to attaching a fixation plate, as will be described below, to secure and retain opening. As another example, as illustrated in FIGS. 13A and 13B, the opening validator 500 can confirm opening 7 prior to attaching predrilling module 300a, and thus help position the same, such that fastener holes can be drilled in the patient's bone 3 after opening 7 has been formed.

Fixation Plate

Figure 6A:
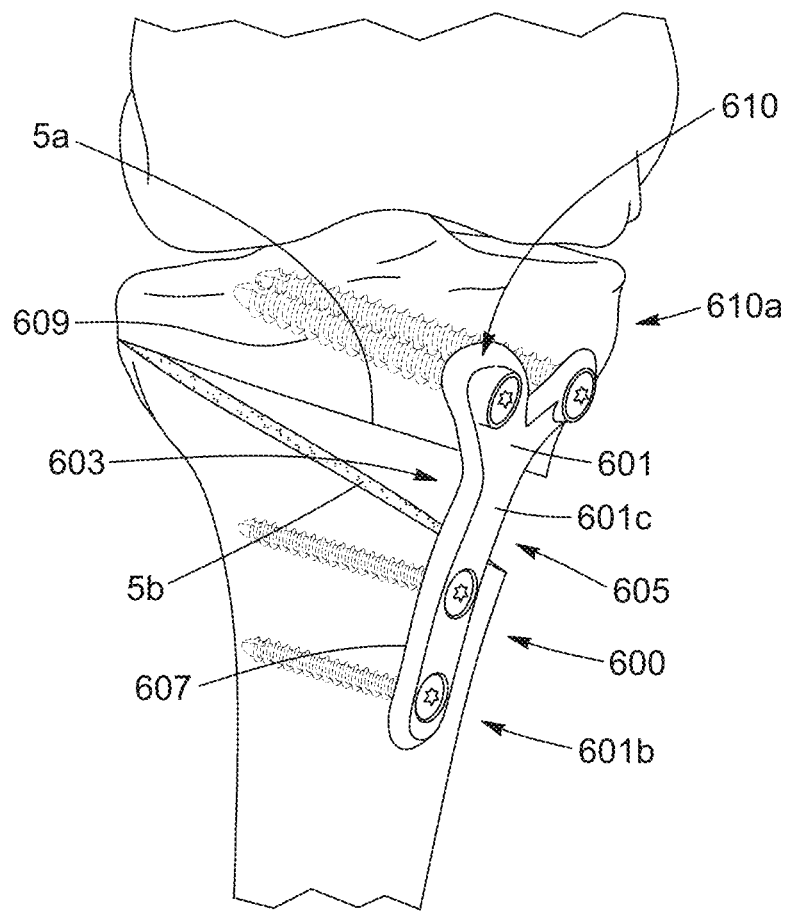
FIG. 6A is a perspective view of a fixation plate securing an open wedge formed in the patient's tibia bone, according to an embodiment.
Figure 6B:
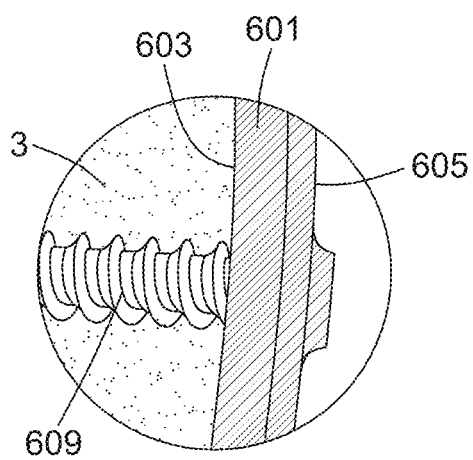
FIG. 6B is a partial-cross section detail view of the fixation plate secured directly to the patient's tibia bone via a fastener.

With reference now to FIGS. 6A and 6B, a fixation plate 600 is shown. Fixation plate 600 comprises a body 601 made from a rigid, biocompatible and degradation-resistant material, such as stainless steel or titanium, although it is appreciated that other materials are possible, including different metals and/or plastics and/or a combination thereof. In the present embodiment, fixation plate 600 is an osteotomy plate for securing to an antero-medial side of the patient's bone 3 and retaining the opening 7 formed therein during an open-wedge osteotomy procedure. It is appreciated that in other embodiments, fixation plate 600 can be configured for securing to another side of the patient's bone 3 depending on surgical requirements. In the present embodiment, body 601 comprises a proximal section 601a for securing to the patient's bone 3 above opening 7, a distal section 601b for securing to the patient's bone 3 below opening 7, and an intermediate section 601c for spanning the opening 7. As will be described in more detail hereinafter, the present fixation plate 600 is patient-specific in that it has been designed based on the specific anatomy of the patient's bone 3 and based on the specific needs of the patient determined during a preoperative plan. The shape and configuration of fixation plate 600 can therefore vary from one procedure to another based upon the bone anatomy of different patients and based on their different needs.

The body 601 of fixation plate 600 is sized, shaped, and configured to fit snugly on the patient's bone 3 while also providing the required support and being minimally noticeable under the patient's skin. In the present embodiment, body 601 is thin and substantially flat, and is configured to follow the contours of the patient's bone 3. In this configuration, for example, when the fixation plate 600 is secured to the patient's bone 3, it can protrude from the surface of the patient's bone 3 at a uniform height along the entire body 601. Moreover, in some embodiments, body 601 can be designed to have a thickness which varies in different locations, allowing body 601 to have increased or reduced strength or rigidity where required and/or allow body 601 to protrude less noticeably from the patient's bone at certain areas.

The body 601 of fixation plate 600 comprises a bone interface side 603 and an outward-facing side 605. Bone interface side 603 comprises an inner surface for positioning adjacent the patient's bone 3. The contours of inner surface of bone interface side 603 are complementary in shape to surface contours of a predetermined position on the patient's bone 3. In this fashion, fixation plate 600 can fit snugly on a position of the patient's bone 3 determined preoperatively. Outward-facing side 605 is substantially smooth and/or flat to make it minimally noticeable under the patient's skin. In the present embodiment, the outward-facing side 605 comprises sloped and/or chamfered edges 607 which provide a smoother transition between the body 601 of fixation plate 600 and the patient's bone 3.

The fixation plate 600 is secured to the patient's bone 3 via fasteners 609. In the present embodiment, fasteners 609 comprise surgical screws which are drilled into the patient's bone 3, although it is appreciated that other type of fasteners are possible. The fasteners 609 engage with plate 600 via apertures or canals 610 opening on the bone interface side 603 and the outward facing side 605 of the plate 600. As can be appreciated, canals 610 can be sized and shaped to receive different sizes of fasteners 609. Moreover, canals 610 can be configured to guide fastener 609 at a predetermined angle or orientation as it is inserted into the patient's bone 3. For example, in the present embodiment, canals 610 comprise sidewalls extending through the thickness of the body 601 of plate 600 at a predetermined angle to guide the fasteners 609 as they are drilled through the canals 610. In some embodiments, the sidewalls of canals 610 can be threaded, for example to engage with corresponding threads of fasteners 609 as the fasteners 609 are being drill through canals 610, and/or to engage or lock with a head of the fasteners 609 once fully inserted. The sidewalls of canals 610 can further be configured to abut against a head of fastener 609 to block the fastener 609 from being inserted too deep into the patient's bone 3.

As can be appreciated, based on a preoperative plan, fixation plate 600 can be designed with a different number and configuration of canals 610 for receiving a different number and configuration of fasteners 609 based on the specific needs of the patient to promote optimal securing of the plate 600. Moreover, the fixation plate 600 can be configured such that it can accommodate combinations of different sizes of fasteners 609 (both diameter and length) and different orientation of fasteners 609, for example based on the position of the patient's bone 3 to which a particular fastener 609 is to be secured. In the illustrated embodiment, the plate 600 is configured to accommodate two large laterally-spaced fasteners 609 in the proximal section of body 601a, and two smaller vertically-spaced fasteners 609 in the distal section of body 601b. As will be explained in more detail hereinafter, many other configurations of plate 600 are possible.

In some embodiments, additional support members can be provided to further assist fixation plate 600 in retaining the opening 7 formed in the patient's bone 3 and/or to assist in correctly positioning fixation plate 600 relative to opening 7. By way of example, and with reference to the embodiment of FIGS. 14, 14A, 14B, and 14C, a wedge element 611 can be provided to abut against internal surfaces 5a, 5b on opposite sides of opening 7 when fixation plate 600 is positioned on the patient's bone 3. As can be appreciated, as a load is applied across opening 7, the wedge element 611 can exert an opposing force on the patient's bone 3 via internal surfaces 5a, 5b. In this configuration, a load across the opening 7 can be borne by the wedge element 611 and dissipated through the patient's bone 3, rather than being borne by the fasteners 609 holding the plate 600 in place. In the illustrated embodiment, wedge element 611 is formed as an integral part of body 601 of fixation plate 600, and is made from the same rigid, biocompatible material, i.e. stainless steel or titanium. It is appreciated, however, that in other embodiments, wedge element 611 can be a separate piece which can be fastened or secured to the fixation plate 600 and/or directly to the patient's bone 3. It is further appreciated that wedge element 611 can be made of a different material, such as a rigid plastic or the like, depending on the required structural properties.

In the present embodiment, wedge element 611 extends from the bone interface side 603 of fixation plate 600, and is positioned on intermediate section 601c of fixation plate body 601. In this configuration, wedge element 611 extends inside opening 7 when the fixation plate 600 is secured to the patient's bone 3. The wedge element 611 comprises a proximal abutment 613 for abutting against a proximal internal surface 5a of bone 3, and a distal abutment 615 for abutting against a distal internal surface 5b of bone 3. Proximal 613 and distal 615 abutments are spaced apart from one another via a concave canal 617. In this configuration, a certain amount of flexure is permitted in the rigid body 601 of fixation plate 600 as a load is applied across abutments 613, 615. It is appreciated, however, that in other embodiments, wedge element 611 can be a solid block having abutments 613, 615 defined on opposite sides thereof.

As with the other components of fixation plate 600, the wedge element 611 can be configured according to patient-specific needs. For example, based on a preoperative plan and 3D models of the patient's bone 3, various components, surfaces, contours, etc. of the wedge element 611 and be shaped and configured to conform to the specific anatomy of the patient's bone 3 and/or opening 7 formed therein. Wedge element 611 can further be configured to provide varying levels of structural support as required based on patient-specific needs.

Figure 16:
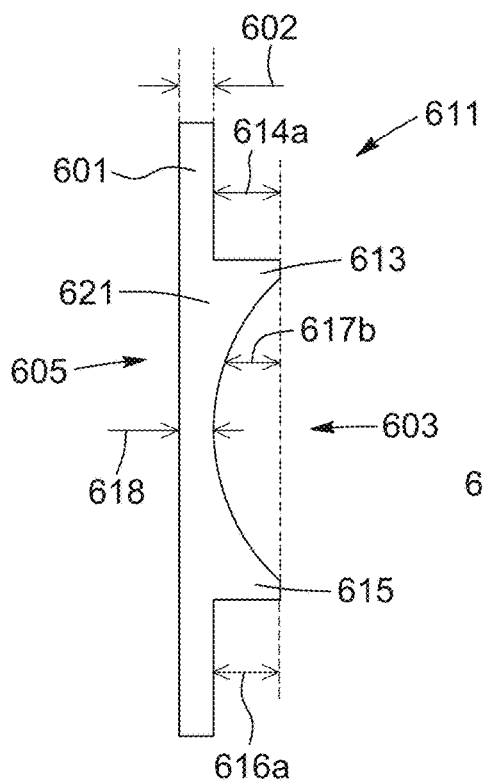
FIG. 16 is a side view of section of a fixation plate having a straight wedge element, according to an embodiment.
Figure 16A:
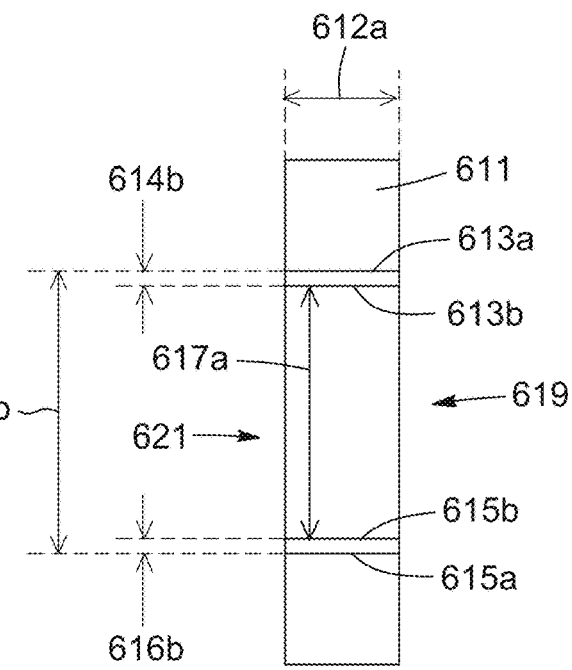
FIG. 16A is a rear view thereof.
Figure 17:
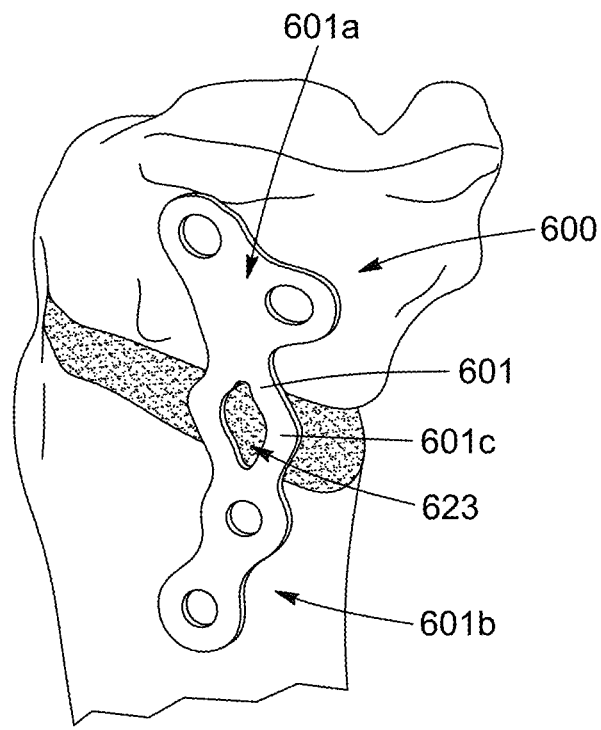
FIG. 17 is a perspective view of a fixation plate securing an open wedge formed in a patient's tibia bone, according to an embodiment in which the fixation plate is provided with two wedge elements.
Figure 17A:
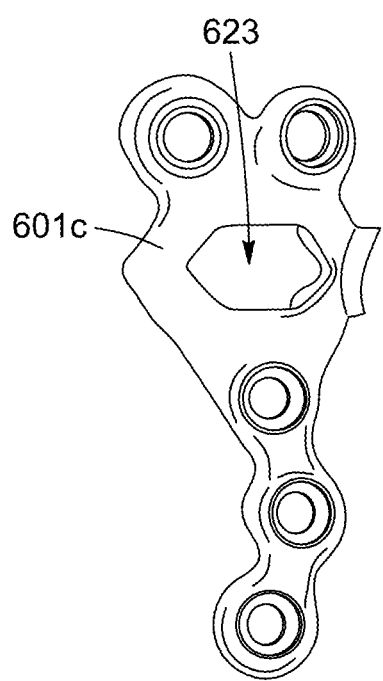
FIGS. 17A and 17B are respective front and rear views of the fixation plate of FIG. 17.
Figure 17B:
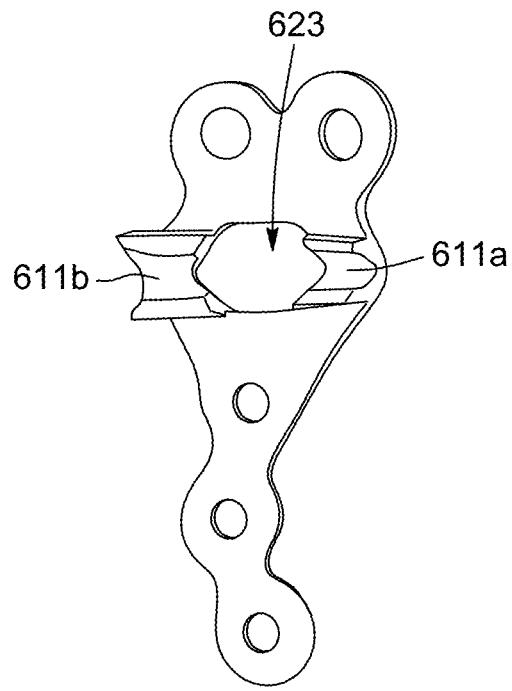
Figure 18A:
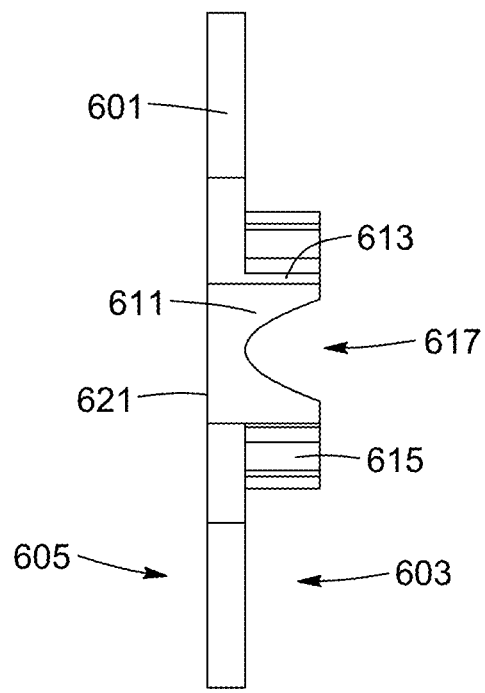
FIG. 18A is a side view of a portion of a fixation plate having two wedge elements, according to an embodiment.
Figure 18B:
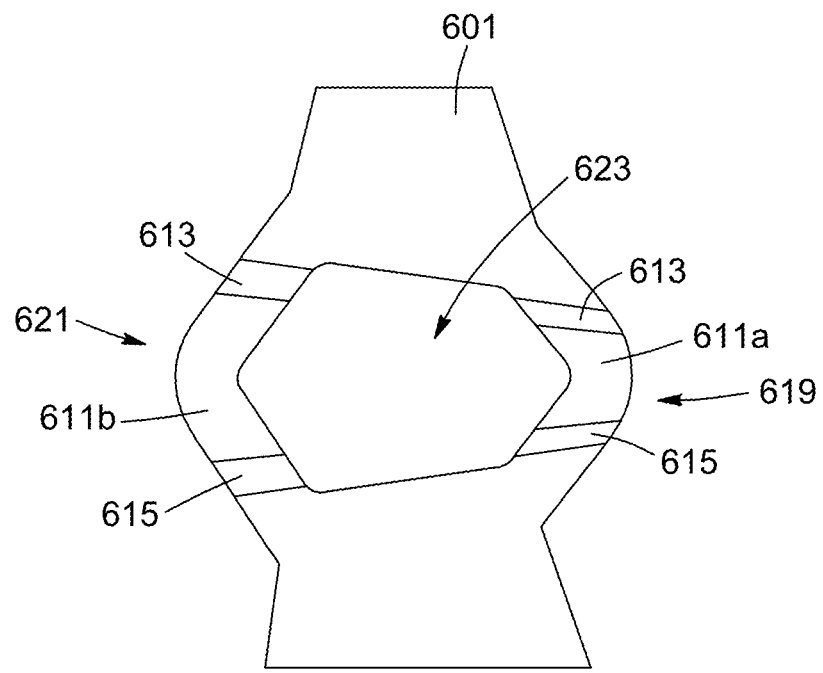
FIG. 18B is a rear view of the fixation plate of FIG. 18A.

More specifically, and with reference to FIGS. 16 and 16A, an exemplary embodiment of a wedge element 611 is shown. In the illustrated embodiment, the body 601 of fixation plate 600 has a nominal thickness 602 in intermediate section 601c, and wedge element 611 extends therefrom. The wedge element 611 comprises proximal 613 and distal 615 abutments extending from body 601 and extends along a width 612a between anterior 619 and posterior 621 sides. The proximal 613 and distal 615 abutments have respective bone contacting bearing surfaces 613a and 615a spaced apart from one another by a spanning distance 612b, for respectively abutting against proximal 5a and distal 5b internal surfaces on opposite sides of opening 7 in the patient's bone 3. As can be appreciated, the spanning distance 612b can be adjusted according to the expected size of opening 7 as determined in a preoperative plan, to extend precisely between proximal 5a and distal 5b internal surfaces and abut against the same. By precisely spanning the distance between proximal 5a and distal 5b internal surfaces, wedge element 611 can provide the necessary support to retain the internal surfaces 5a, 5b a fixed distance from one another, and retain opening 7 at the desired opening angle. In this configuration, wedge element 611 can further assist in correctly positioning fixation plate 600 on the patient's bone 3. As can be appreciated, the wedge 611 will only be able to fit inside the opening 7 at a position where the opening is wide enough to accommodate the spanning distance 612b of abutments 613, 615. Accordingly, the wedge element 611 can be designed with a spanning distance 612b such that it fits inside opening 7 at a predetermined position and orientation relative to the patient's bone 3, as determined in a preoperative plan, thereby positioning the fixation plate 600 to which the wedge element 611 is secured.

Figure 24A:
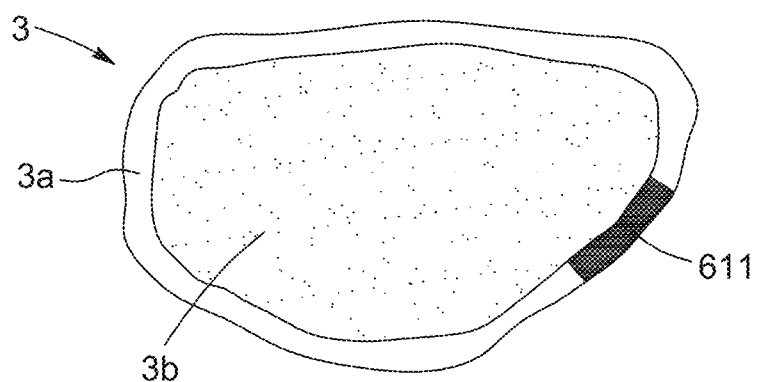
FIG. 24A is a cross sectional view showing a fixation plate secured to a patient's tibia bone, according to an embodiment in which the fixation plate is provided with a single wedge element conforming to the patient's cortical bone.

In the present embodiment, and as shown in FIG. 24A, wedge 611 is configured to abut against the patient's cortical bone 3a, i.e. the hard outer layer of patient's bone 3, as opposed to the soft trabecular bone 3b. Accordingly, and referring back to FIGS. 16 and 16A, proximal 613 and distal 615 abutments can be sized and shaped to interface with the patient's cortical bone 3a while avoiding contact with the patient's trabecular bone 3b. More particularly, in the present embodiment, bone contacting surfaces 613a and 615a are substantially planar and extend substantially perpendicular relative to body 601 through respective depths 614a and 616a. As can be appreciated, depths 614a and 616a can be adjusted based on the thickness of the patient's cortical bone 3a, such that the abutments 613 and 615 extend into opening 7 to a depth corresponding to the thickness of the cortical bone 3a, for example to approximately 4 mm. In the present embodiment, bone contacting surfaces 613a and 615a have the same depths 614a, 616a, but it is appreciated that in other embodiments, the depths can be different, for example depending on the expected position and orientation of wedge 611, and/or variances in the thickness of the patient's cortical bone 3a. As can be appreciated, the surface areas of bearing surfaces 613a and 615a are defined by depths 614a, 616a, and width 612a of wedge 611. Accordingly, width 612a can be adjusted, in addition to depths 614a, 616a, according to the required surface area of bearing surfaces 613a, 615a. In the present embodiments, width 612a is approximately 8 mm, but other sizes are also possible depending on patient-specific requirements.

As mentioned above, the wedge element 611 can be configured to provide different levels of support based on patient-specific needs. For example, for some patients, it may be desirable to have more rigidity in the fixation plate 600, whereas for other patients, it may be desirable to allow a certain amount of micromovements via flexure or deformation of the fixation plate 600 across the opening 7. Accordingly, respective thicknesses 614b and 616b of proximal 613 and distal 615 abutments can be adjusted based on a desired level of rigidity. For example, in some embodiments, such as the one illustrated in FIGS. 16 and 16A, abutments 613, 615 can be relatively thin members extending from body (for example with thicknesses 614b and 616b of approximately 1 mm), thus allowing a certain amount of deformation as loads are applied to their respective bearing surfaces 613a, 615b. In other embodiments, abutments 613, 615 can be relatively thick and/or can have a thickness corresponding to the spanning distance 612b of wedge 611 (i.e. the wedge being formed from a solid block of material, with abutments 613, 615 defined on opposite sides thereof), thereby providing increased rigidity and allowing little to no deformation of wedge 611 under typical loads. In the embodiment illustrated in FIGS. 16 and 16A, the respective thicknesses 614b, 616b of abutments 613 and 615 are the same, however it is appreciated that in other embodiments they can be different, for example to provide different levels of rigidity in proximal and distal sections of plate 600 and/or to control the distribution of forces in wedge 611 as a load is applied to abutments 613, 615.

As can be appreciated, abutments 613 and 615 can be designed with different shapes and configurations which can further affect the rigidity and/or the distribution of forces in wedge 611. For example, in the embodiment shown in FIGS. 16 and 16A, abutments 613 and 615 are configured as curved members with a progressive reduction of their depths 614a, 616a towards a central area of wedge 611. In other words, a canal 617 extends along a height 617a between respective interior edges 613b, 615b of abutments 613 and 615. The canal 617 has a depth 617b which increases towards the central area of wedge 611, thereby subtracting from the depths of abutments 613, 615. In the present embodiment, the depth 617a of canal 617 follows a polynomial curve (i.e. $AX^2+BX+C$), reaching a maximum depth 617b midway along its height 617a. Thus, when viewed from posterior 219 or anterior 221 sides, the canal 617 has a parabolic or C-shaped profile. In this configuration, when a load is applied across abutments 613, 615, stresses can be focused towards the central area of the wedge 611. Although in the present embodiment the canal 617 is substantially C-shaped, it is appreciated that other configurations are also possible, including different shapes having progressive and/or abrupt changes in depth 617b. For example, in some embodiments, the canal 617 can have a substantially V-shaped profile, a substantially rectangular-shaped profile, etc. In the present embodiment the maximum depth 617a of canal 617 corresponds to the depths 614a, 616a of abutments 613, 615. In this configuration, the canal 617 does not extend past the thickness 602 of plate 600. It is appreciated, however, that other configurations are possible. For example, the canal 617 can be shallower than depths 614a, 616a, such that a minimum or base thickness 618 of plate 600 between abutments 613, 615 is thicker than a nominal thickness 602 of plate 600 adjacent to the wedge 611.

In the illustrated embodiment, the wedge 611 can be referred to as a straight wedge in that the bearing surfaces 613a, 615a are substantially straight and uniform. For example, bearing surfaces 613a, 615a are substantially rectangular, and are substantially parallel to one another. Similarly, the canal 617 is straight and uniform along the width 612a of wedge 611. It is appreciated, however, that the shape and orientation of bearing surfaces 613a, 615a, and/or canal 617 can be adjusted to better conform to the specific needs of a patient. For example, as illustrated in FIGS. 20, 20A and 20B the surface area of bearing surfaces 613a, 615a of a straight wedge 611 may not be in full contact with interior surfaces 5a, 5b of opening 7, and can thus create areas of increased pressure. However, if wedge 611 is configured to follow the shape of interior surfaces 5a, 5b as shown in FIGS. 21, 21A and 21B, a superior interface between wedge 611 and the patient's bone 3 can be achieved (i.e. increased surface area of contact), allowing for better stress distribution through the bone.

Figure 15:
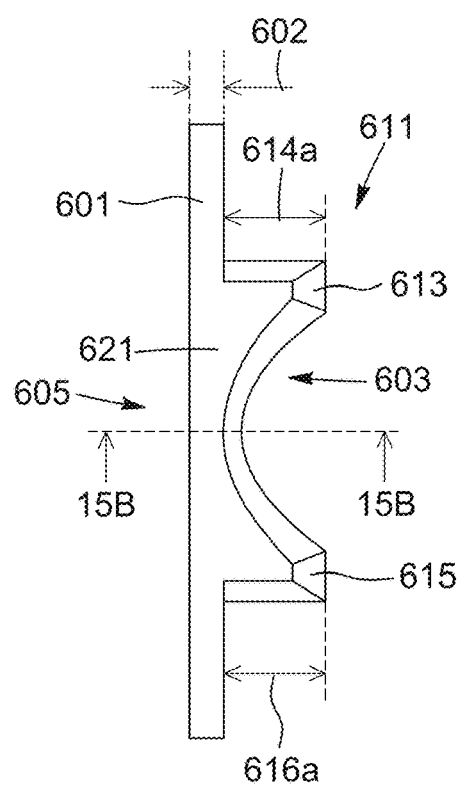
FIG. 15 is a side view of a portion of a fixation plate having a wedge element with an evolutive canal and patient-specific bone conforming surfaces, according to an embodiment.
Figure 15A:
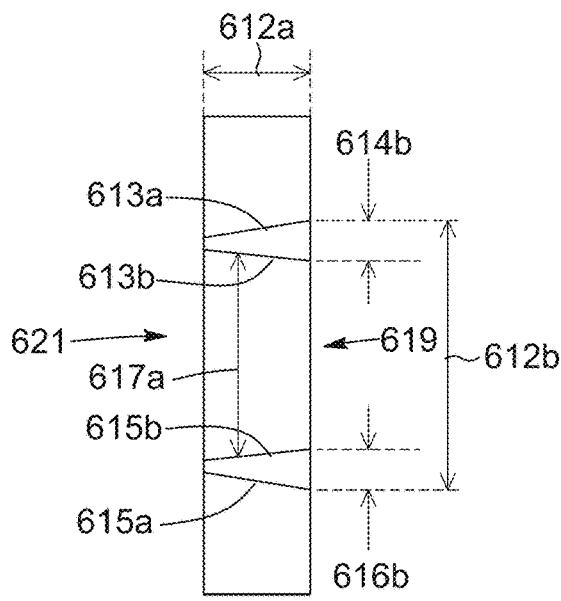
FIG. 15A is a rear view of the fixation plate of FIG. 15.
Figure 15B:
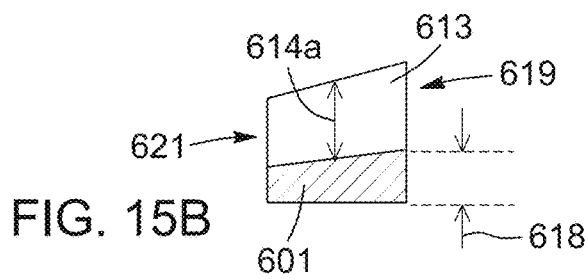
FIG. 15B is a cross sectional view of the fixation plate of FIG. 15 taken along line 15B-15B.
Figure 22:
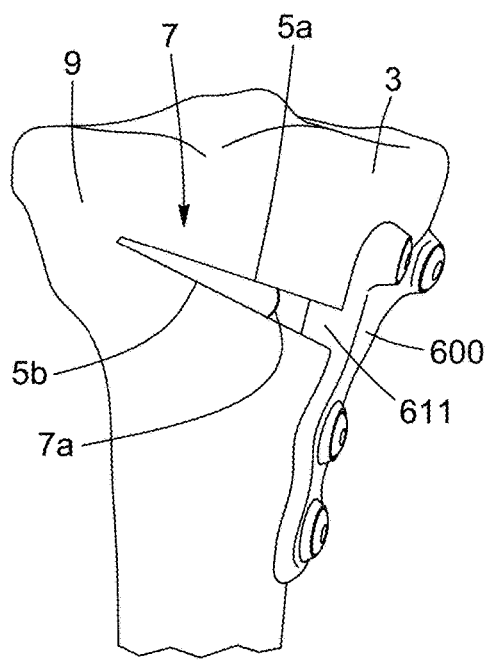
FIG. 22 is a side perspective view of an open wedge formed in a patient's tibia bone supported by a fixation plate with a bone conforming wedge having tapered bearing surfaces, according to an embodiment.
Figure 22A:
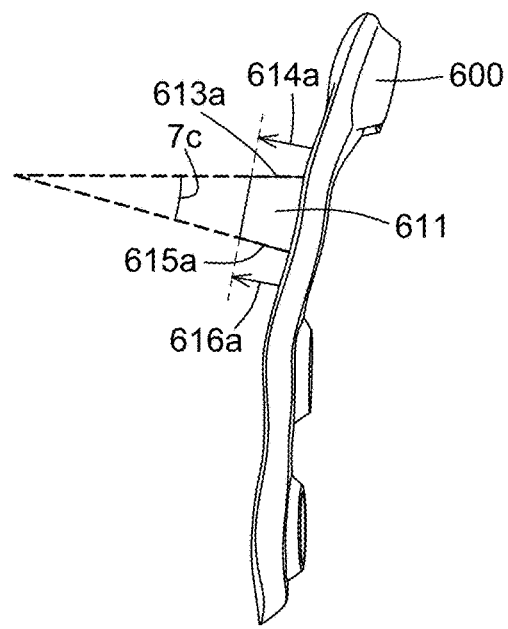
FIG. 22A is a side view of the fixation plate of FIG. 22.

With reference now to FIGS. 15, 15A and 15B, a wedge element 611 is shown according to an alternate embodiment in which abutments 613, 615 are shaped to follow the specific shape and contours of opening 7. More specifically, in the illustrated embodiment, bearing surfaces 613a, 615a are sloped or tapered along the direction of width 612a. Similarly, bearing surfaces 613a, 615b are sloped or tapered along the direction of their depths 614a, 616a. In this configuration, when the wedge 611 is positioned inside opening 7, bearing surfaces 613a, 615a can follow the slope of interior surfaces 5a, 5b, and increase the contact surface area therewith. This configuration of wedge 611 can further allow for the correction of *varus*/valgus deformity in the frontal plane as well as the correction of the tibial slope in the sagittal plane. In the present embodiment, bearing surfaces 613a, 615b are tapered inwards along width 612a towards the posterior side 621, to follow a corresponding narrowing of opening 7 towards a posterior side of the patient's bone 3. It is appreciated, however, that the tapering direction and magnitude can differ according to the expected shape of the opening 7 as determined in a preoperative plan. It is also appreciated that the proximal 613a and distal 615a bearing surfaces can be tapered at different angles. In the present embodiment, bearing surfaces 613a, 615a are also tapered inward along the direction of their depths 614a, 616a. In this configuration, the bearing surfaces 613a, 615a can follow the slope of interior surfaces 5a, 5b as they converge towards hinge 9 at opening angle 7a, as shown in FIGS. 22 and 22A. Again, it is appreciated that the tapering angle of bearing surfaces 613a, 615a can be different.

Figure 23:
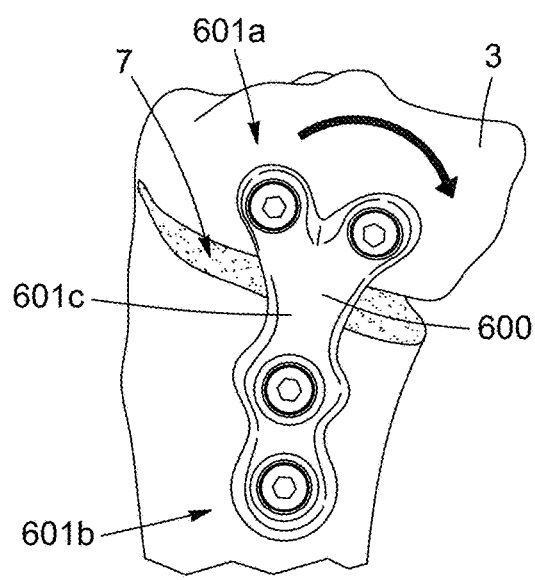
FIG. 23 is a front perspective view of an open wedge formed in a patient's tibia bone supported by a fixation plate with a bone confirming wedge having offset bearing surfaces, according to an embodiment.
Figure 23A:
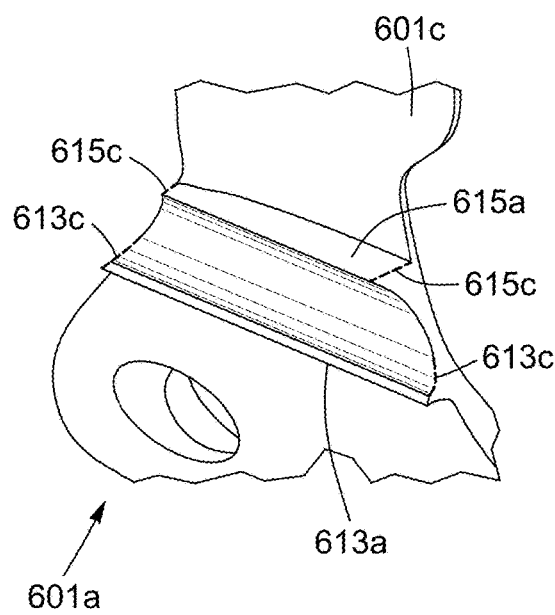
FIG. 23A is a detail view of the wedge element of the fixation plate of FIG. 23.

In the present embodiment, the width 612a of the wedge 611 is uniform along the wedge span 612b. In other words, bearing surfaces 613a, 615a are aligned with one another, and have the same width 612a. It is appreciated, however, that in other embodiments, bearing surfaces 613a, 615a can have different widths and/or can be offset from one another. For example, as illustrated in FIGS. 23 and 23A, load distribution in the patient's bone 3 can be physiologically more important in the medial compartment. Accordingly, when plate is secured to patient's bone 3 across opening 7, the plate 600 can undergo a rotation effort in the antero-medial plane. To equilibrate the stress induced in the wedge 611 and bone 3, bearing surfaces 613a, 615a can have different widths and/or can be offset, for example by being configured with tapered side edges 613c, 615c. It is appreciated that other relative size and positions of bearing surfaces 613a, 615a are also possible in different embodiments, according to patent specific requirements.

In the embodiment illustrated in FIGS. 15, 15A and 15B, the wedge element 611 is further configured with bearing surfaces 613a, 615a which conform to a shape of the patient's cortical bone 3a to ensure better contact therewith, and avoid contact with the trabecular bone 3b. As can be appreciated, the thickness of the patient's cortical bone 3a can vary at different points along the circumference of the patient's bone 3. Accordingly, the respective depths 614a, 616a of abutments 613, 615 can in direction of wedge width 612a. In the present embodiment, and as best illustrated in FIG. 15B, depths 614a of proximal abutment 613 decreases from anterior side 619 to posterior side 621, thus defining a bearing surface 613a having a sloped or tapered interior edge shaped to match a thinning of the patient's cortical bone 3a towards posterior side 621. Although in the present embodiment the interior edge of bearing surface 613a has a sloped, linear shape, it is appreciated that other shapes are also possible depending on the specific shape of the patient's cortical bone 3a. Moreover, although only the proximal abutment 613 is shown in FIG. 15B, it is appreciated that distal bearing surface 615a can be configured with a similar or different shape.

In the present embodiment, the wedge element 611 is further configured with an evolutive canal 617, i.e. a canal having a shape which changes or evolves along width 612a of wedge 611. As shown in FIGS. 15, 15A and 15B, the height 617a of canal 617 varies along width 612a wedge. More specifically, interior edges 613b, 615b of abutments 613, 615 are tapered inwards from posterior side 621 to anterior side 619, resulting in the canal height 617a decreasing from posterior side 621 to anterior side 619. In the present embodiment, edges 613b, 615b are angled inward towards one another at substantially equal and opposite angles, although it is appreciated that in other embodiments, angles of edges 613b, 615b can differ, or edges 613b, 615b can be angled and parallel to one another. It is further appreciated that in other embodiments, edges 613b, 615b can follow curved paths. As can be appreciated, the present configuration of canal 617 can also allow abutments 613, 615 to have evolutive thicknesses 614b, 616b along width 612a. More particularly, in the present embodiment, respective thicknesses 614b, 616b of abutments 613, 615 increase from posterior side 621 to anterior side 619.

In the present embodiment, the wedge element 611 is further configured with a minimum or base thickness 618 of plate 600 which varies along width 612a of wedge 611. As best shown in FIG. 15B, the base thickness 618 increases from posterior side 621 to anterior side 619. For example, on posterior side 621, the base thickness 618 can correspond to the nominal thickness 602 of plate 600, whereas on anterior side 619, the base thickness 618 can be greater than the nominal thickness 602. Although in the present embodiment the base thickness 618 increases linearly along width 612a, it is appreciated that in other embodiments, the change in thickness 618 can be nonlinear. As can be appreciated, variances in base thickness, along with the variances in the canal configuration and/or abutment thicknesses can allow for the rigidity and/or permitted amount of micromovements between abutments 613, 615 to vary across the width 612a of wedge 611.

In the embodiments described above, plate 600 is provided with a single wedge 611 was shown for engaging in opening 7 along an antero-medial side of the patient's bone 3. It is appreciated, however, that in other embodiments, other wedge configurations are possible. For example, with reference to FIGS. 17, 17A, 17B, 18A and 18B, a double wedge plate 600 is shown according to an embodiment. In the illustrated embodiment, plate 600 is provided with a first anterior wedge 611a, and a second posterior wedge 611b spaced apart from one another in intermediate section 601 of plate body 601. In the present configuration, wedges 611a and 611b are spaced apart from one another via an opening 623 in plate body 601. As can be appreciated, opening 623 can help reduce the weight of plate and/or to encourage flexure in the intermediate section 601c. It is appreciated that in other embodiments, opening 623 need not be provided, and plate body 601 can be closed between wedges 611a and 611b.

Figure 24B:
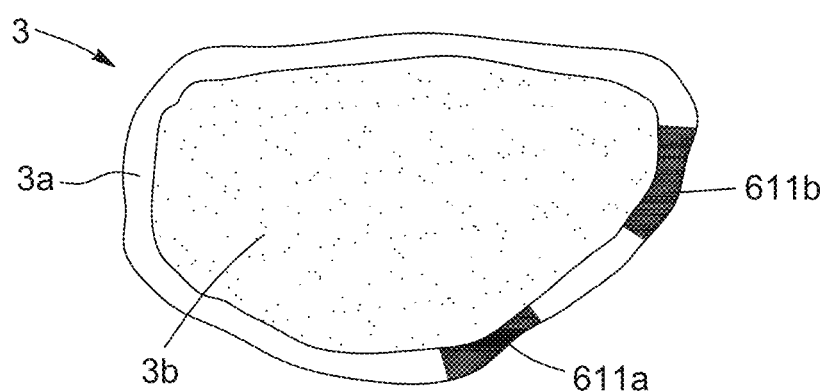
FIG. 24B is a cross sectional view showing a fixation plate secured to a patient's tibia bone, according to an embodiment in which the fixation plate is provided with two wedge elements conforming to the patient's cortical bone.

When plate 600 is engaged with patient's bone 3, wedges 611a and 611b engage in opening 7 on an antero-medial side of the patient's bone 3, providing support at anterior and posterior positions. As with the embodiments of the patient-specific wedges described above, each of wedges 611a and 611b can be configured according to patient-specific needs, and based on patient-specific anatomy. For example, as illustrated in FIG. 24B, each of wedges 611a and 611b can be shaped and configured to follow and abut the patient's cortical bone 3a. The other size and shape parameters of wedges 611a and 611b, as described above, can also be customized based on the expected position of wedge 611a, 611b as determined preoperatively, and the dimensions of wedges 611a, 611b can differ from one another. For example, in the present embodiment, posterior wedge 611b has a spanning distance greater than the spanning distance of anterior wedge 611a to account for a widening of opening 7 towards the posterior. The size, shape and configuration of wedges 611a, 611b can further be configured such that wedges 611a and 611b work together to provide the necessary level of support, and/or account for stress distribution in the plate 600 and/or the patient's bone 3 based on patient-specific requirements as determined preoperatively.

Figure 19:
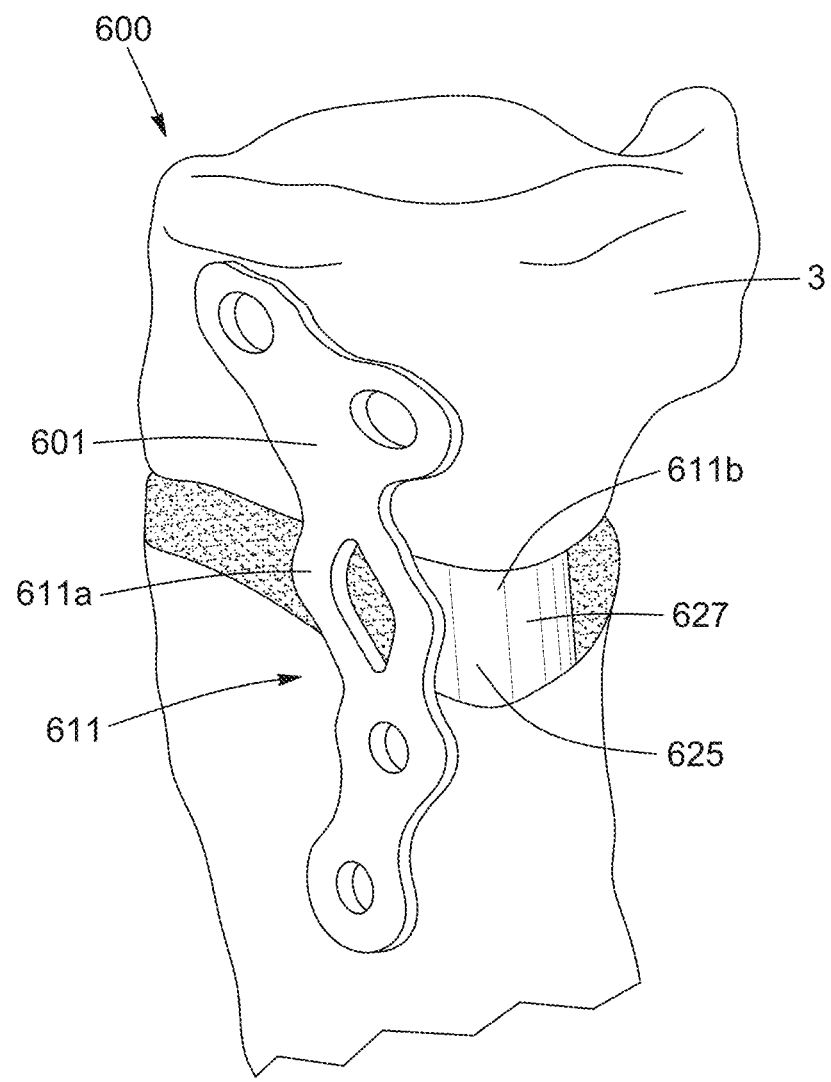
FIG. 19 is a perspective view of a fixation plate securing an open wedge formed in a patient's tibia bone, according to an embodiment in which the fixation plate is provided with a C-shaped wedge element.
Figure 24C:
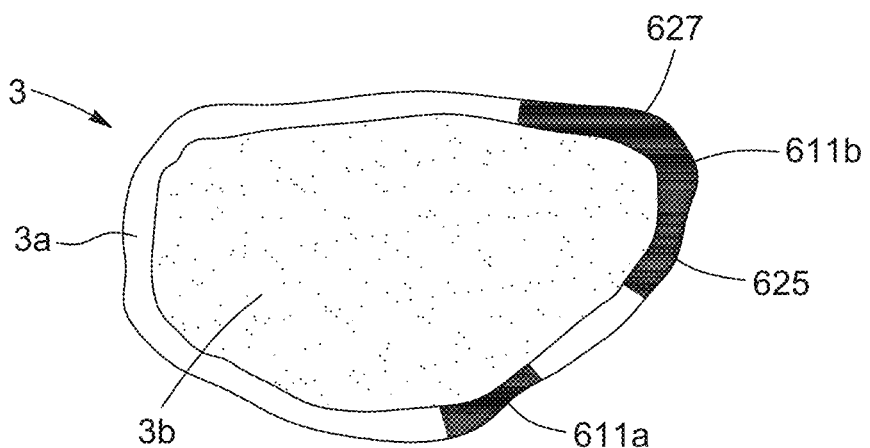
FIG. 24C is a cross sectional view showing a fixation plate secured to a patient's tibia bone, according to an embodiment in which the fixation plate is provided with C-shaped wedge element conforming to the patient's cortical bone.

In the embodiments described above, the wedge 611 is configured to engage in, and provide support to, opening 7 on an antero-medial side of the patient's bone 3. It is appreciated, however, that in some embodiments, further support may be desired towards the anterior and/or posterior of the patient's bone 3. Accordingly, in some embodiments, the wedge 611 can be configured as an extended wedge with a section which extends away from the plate body 601 in the anterior and/or posterior direction. With reference to FIG. 19, an exemplary fixation plate 600 with an extended wedge 611 is provided. In the illustrated embodiment, the wedge 611 is a double wedge and comprises an anterior wedge element 611a and a posterior wedge element 611b. The posterior wedge element 611b is configured as an extended wedge which comprises an anterior section 625 extending from plate body 601 along the antero-medial section of the patient's bone 3, and a posterior section 627 which extends from anterior section 625 towards the posterior of the patient's bone 3. As can be appreciated, and as shown in FIG. 24C, the extended wedge element 611b is configured to follow the contour of the patient's bone 3 as it wraps around towards the posterior, and therefore defines a C-shape. It is appreciated, however, that other shapes are possible. It is further appreciated that in other embodiments, the extended wedge can comprise an anterior-extending section which can wrap around an anterior surface of the bone. It should be appreciated that although the posterior wedge 611b is configured as an extended wedge in the present embodiment, in other embodiments the anterior wedge 611a can be configured as an extended wedge in place of, or in addition to the posterior wedge 611b. Finally, it should be appreciated that an extended wedge can be provided as part of a plate having a single wedge.

As can be appreciated, as with the other embodiments of wedges describes above, the extended wedge 611 can have contours and surfaces that conform to the specific shape of the patient's bone 3. For example, as shown in FIG. 24C, the extended wedge 611b can be sized and shaped to follow and abut against the patient's cortical bone 3a, while avoiding the trabecular bone 3b. The extended wedge 611b can further be configured with tapered and/or offset abutments surfaces as described above and can be provided with a straight or evolutive channel to provide flexure if desired.

Spacing Element

In the embodiment illustrated in FIG. 6B, the fixation plate 600 is in direct contact with the patient's bone 3. In other words, the inner surface of bone interface side 603 of fixation plate 600 abuts directly against the surface of the patient's bone 3. It is appreciated, however, that in other embodiments, the fixation plate (or section thereof) can be spaced apart from the patient's bone 3 and not be in direct contact therewith. Accordingly, bone interface side 603 can be configured to conform to surface contours of the patient's bone 3 at a predetermined spacing therefrom, and spacing elements can be provided to create a spacing between inner surface of bone interface side 603 and the surface of the patient's bone 3 when the fixation plate 600 is secured to the patient's bone 3.

Figure 7:
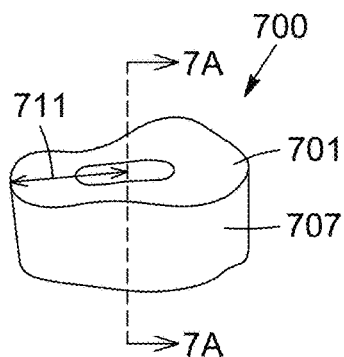
FIG. 7 is a perspective view of a spacing element, according to an embodiment.
Figure 7A:
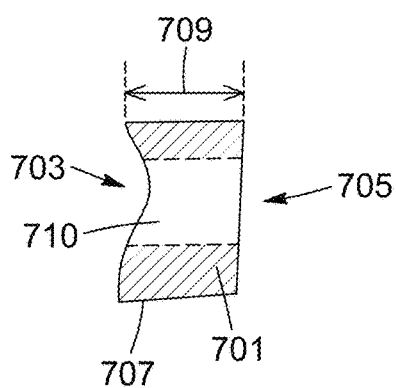
FIG. 7A is a cross sectional view of the spacing element of FIG. 7 taken along 7A-7A.

With reference to FIG. 7, a spacing element 700 for spacing a fixation plate from a patient's bone is shown according to an embodiment. Spacing element 700 comprises a body 701 made from a rigid, biocompatible material, such as metal, which can be the same or different material than fixation plate. Body 701 has a bone interface side 703 for contacting the patient's bone, and a plate interface side 705 for contacting the fixation plate. Sidewalls 707 extend between the bone interface side 703 and the plate interface side 705, defining a thickness 709 of the spacing element. The body 701 further defines a central aperture 710 for allowing a corresponding fastener to pass there-through. The central aperture extends through the thickness 709 of the body 701, and opens on the bone interface side 703 and the plate interface side 705. In the present embodiment, the body 701 is substantially cylindrical in shape, with a radius 711. It is appreciated, however, that other shapes are also possible. For example, in some embodiments, body 701 can be frustoconical in shape, and can have a radius 711 which varies along thickness 709.

In the present embodiment, the spacing element 700 is custom made to conform to the specific anatomy of a patient's bone. More specifically, the bone interface side 703 comprises a surface having contours conforming to the surface contours of the patient's bone. As can be appreciated, the position of spacing element 700 can be determined during pre-operative planning using a 3D model of the patient's bone, and the surface of bone interface side 703 can be configured to conform to the patient's bone at the determined position, such that the spacing element 700 fits snugly against the patient's bone at a specific position and orientation. The thickness 709 and radius 711 of spacing element 700 can further be adjusted based on patient-specific requirements. For example, as will be discussed in more detail below, thickness 709 can be adjusted to create a larger or smaller spacing distance, and radius 711 can be adjusted to increase or decrease the surface area of spacing element 700 in contact with the patient's bone and/or the fixation plate. In the present embodiment, the surface of plate interface side 705 is substantially flat and planar, however it is appreciated that in other embodiments, it can be configured to conform to a particular contour of the plate. Moreover, in some embodiments, plate interface side 705 and/or sidewalls 707 can be shaped and configured to key into fixation plate, for example to assure proper alignment and relative orientation of spacing element 700 and fixation plate. In some embodiments, interface side 705 can be configured to removably adhere or secure to fixation plate.

Figure 8:
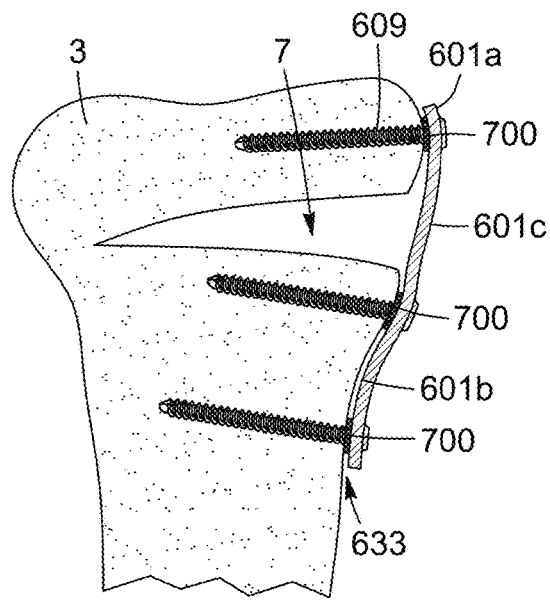
FIG. 8 is a cross sectional view of a fixation plate secured to a patient's tibia bone via fasteners using spacing elements, according to an embodiment.

With reference to FIG. 8, spacing element 700 is positioned between the fixation plate 600 and the patient's bone 3 to create a spacing 633 there-between. In the present embodiment, a plurality of spacing elements 700 is provided. Each of the spacing elements 700 is aligned with a corresponding fastener 609 and is specifically configured to conform to a particular position on the patient's bone 3. Each fastener 609 extends through the fixation plate 600 and through a corresponding spacing element 700 before securing in the bone 3. In the present embodiment, a spacing element 700 is provided for each fastener 609, although it is appreciated that in other embodiments, spacing elements 700 can be provided for only some of the fasteners 609. In the present embodiment, the spacing elements 700 are positioned relative to the fixation plate 600 during the surgical procedure, although it is appreciated that in other embodiments, spacing elements 700 can be pre-adhered to fixation plate 600.

Figure 8A:
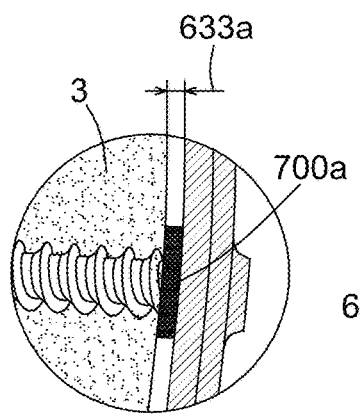
FIGS. 8A, 8B and 8C are partial-cross section detail views of the fixation plate spaced apart from the patient's bone at different distances via different sizes of spacing elements.
Figure 8B:
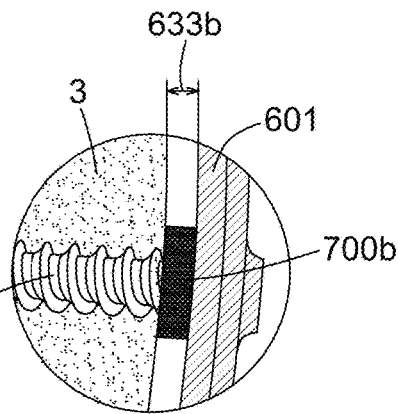
Figure 8C:
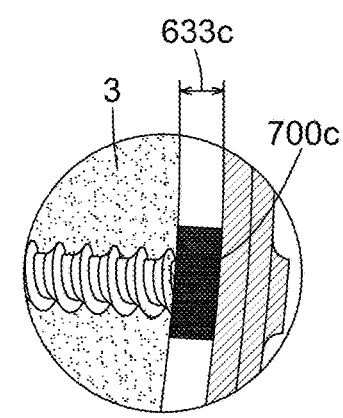

As can be appreciated, the number and configuration of the spacing elements 700 can be selected based on patient-specific spacing requirements. For example, in the present embodiment, spacing elements 700 are configured to provide a spacing 633 of approximately 2 mm. However, as illustrated in FIGS. 8A, 8B and 8C, other embodiments of spacing elements 700a, 700b, 700c can have different thicknesses 709 to provide different spacing distances 633a, 633b, 633c, for example within the range of approximately 1.8 mm to 2.2 mm. In the embodiment illustrated in FIG. 8, the spacing elements 700 are configured to provide a consistent or uniform spacing along the entire area of fixation plate 600. However, it is appreciated that in other embodiments, plate 600 and spacing elements 700 can be configured such that some sections of spacing plate 600 are spaced further apart from the patient's bone 3 than other sections. For example, proximal section 601a can be spaced away from bone 3 at a first spacing distance 633a, whereas distal section 601b can be spaced away from bone 3 at a second spacing distance 633b. Accordingly, a single plate 600 can be secured to bone 3 using a plurality of spacing elements 700 having different thicknesses. Moreover, in some embodiments, the spacing elements 700 used for the same plate 600 can have different radii 711, such that some spacing elements 700 have larger bone-contacting surfaces than others.

In the above-described embodiments, spacing elements 700 are independent from plate 600 in that they are not integrally formed as part of plate body 601. Instead, the described spacing elements 700 can be removable and/or repositionable relative to plate 600 and/or can be made from different materials than plate 600. It is appreciated, however, that in other embodiments, spacing elements 700 can be integrally formed as part of plate 600. Accordingly, a plate with integrally formed spacing elements 700 can be referred to as a low contact plate, in that the plate is configured to have a bone interface side with reduced contact surface area with the patient's bone 3 by way of spacing elements 700. In contrast, a plate without spacing elements can be referred to as a full contact plate, in that the bone interface side will be in full contact with the patient's bone 3.

With reference to FIGS. 25A, 25B, 25C, 25D and 25E, an exemplary full contact plate 600 is shown according to an embodiment. In the illustrated embodiment, the plate 600 comprises a body 601 with a bone interface side 603 opposite an outward facing side 605. Fastener aperture 610 extend through body 601 and open on the bone interface 603 and outward facing 605 sides. As can be appreciated, the bone interface side 603 is substantially flat and featureless (i.e. without bumps, protrusions, etc.), defining a continuous or unbroken bone contacting surface 604 extending substantially throughout the entirety of the bone interface side 603. Although in the present embodiment the bone interface side 603 is substantially planar, it is appreciated that this is for illustrative purposes only, and that in other embodiments the bone interface side 603 can follow the contours of the surface of a patient's bone 3 while having a flat and featureless surface to allow full and direct contact with the surface of the patient's bone 3.

In the present embodiment, outward facing side 605 is provided with surface features to allow for a smooth transition between the surface of the patient's bone 3 and the plate 600. A sloped or chamfered edge 607 extends around the perimeter of body 601 on outward facing side 605, providing a gradual transition between the bone interface side 603 and a highest point on the outward facing side 605. The plate 600 is further configured with annular recesses 608a and/or annular bumps or protrusions 608b around fastener apertures 610 on outward facing side 605. The recesses 608a and/or bumps 608b can allow for a fastener to be seated in plate 600 when engaged in aperture 610 and prevent the fastener from protruding from a highest point of outward facing side 605. As can be appreciated, this configuration can allow for a smooth transition between fastener head and plate 600.

An exemplary low contact plate 600 is shown according to an embodiment in FIGS. 26A, 26B, 26C, 26D, 26E and 26F. As can be appreciated the structure of low contact plate 600 is substantially similar to the full contact plate described above, including similar surface features on outward facing side 605. However, as best seen in FIGS. 26B, 26D, 26E and 26F, bone interface side 603 is provided with surface features in the form of annular bumps or protrusions around apertures 610, defining spacing elements 700. In the present embodiment, spacing elements 700 are integrally formed as part of plate body 601 and are formed from the same material. It is appreciated, however, that in other embodiments, spacing elements 700 can be fused to body 601 and/or can be made of a different material. As can be appreciated, spacing elements 700 define a plurality of bone contacting surfaces 604 on bone interface side 603. This can reduce the overall area of plate body 601 in contact with the patient's bone 3, as the plate will only contact the bone along the surface 604 of spacing elements 700, rather than along the entirety of the bone interface side 603. It should be appreciated that in the present embodiment, bone contacting surfaces 604 on spacing elements 700 are substantially planar for illustrative purposes only. In other embodiments, the bone contacting surfaces 604 on spacing elements 700 can be shaped to conform to the surface contours of the patient's bone 3 to assure full contact between surface 604 and the surface of the patient's bone 3. Finally, although in the present embodiment spacing elements 700 are provided as annular surface features around apertures 610, it should be appreciated that in other embodiments, the surface features defining spacing elements 700 can be provided elsewhere on bone interface side 603 of plate 600.

Fasteners

As discussed above, fixation plate 600 can be secured to a patient's bone 3 via fasteners 609. The fixation plate 600 can be configured with different numbers of apertures 610 to accommodate different numbers of fasteners 609, and apertures 610 can be sized to accommodate different sizes of fasteners 609 and oriented to guide fasteners 609 at predetermined angles into the patient's bone 3. Accordingly, the surgeon can select the desired number, size, position, and orientation of fasteners 609 during a preoperative plan, and fixation plate 600 can be configured to accommodate the same. The surgeon can further select a desired length of fastener, for example depending on the desired depth that fastener should extend into the patient's bone 3.

Figure 27:
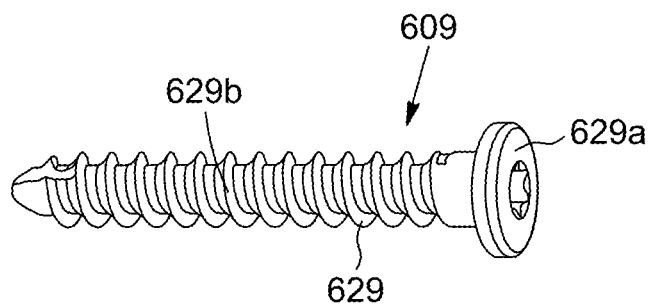
FIG. 27 is a perspective view of a fastener for a fixation plate, according to an embodiment.
Figure 27A:
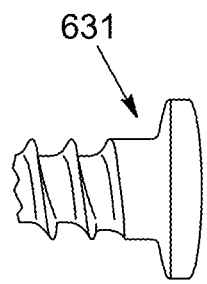
FIG. 27A is a detail view of the head of the fastener of FIG. 27.

As can be appreciated, different types of fasteners 609 can be provided to secure fixation plate 600 to the patient's bone 3. With reference to FIGS. 27 and 27A, an exemplary embodiment of a fastener 609 in the form of a flat-headed surgical screw is provided. The fastener 609 comprises a body 629 with a head 629*a* and a threaded section 629*b*. The fastener 609 is a flat-headed fastener in that head 629*a* has a substantially planar surface, although it is appreciated that in other embodiments, other shapes are possible.

Figure 28:
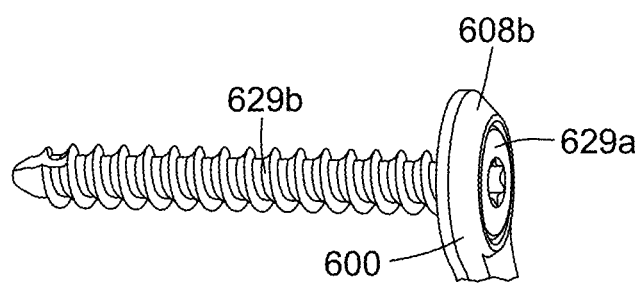
FIG. 28 is a perspective view of the fastener of FIG. 27 installed in a fixation plate having a chamfered edge, according to an embodiment.
Figure 28A:
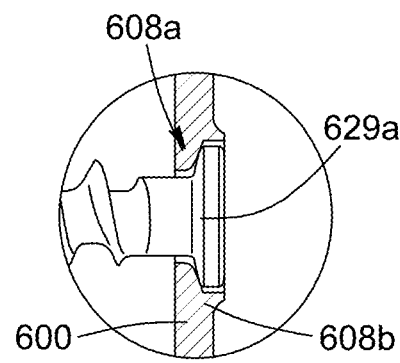
FIG. 28A is a partial cross-sectional view of the plate of FIG. 28 showing a seat for minimizing protrusion of the fastener head from the plate.

As illustrated in FIGS. 28 and 28A, the illustrated fastener 609 is sized and shaped to cooperate with aperture 610 in plate 600. More specifically, fastener 609 is sized to engage in a fastener seat 608 defined via annular recess 608*a* and annular bump 608*b* around aperture 610. In this configuration, when fastener 609 is engaged in aperture 610, head 629*a* is flush with annular bump 608*b*, defining a smooth contour therewith, and preventing fastener 609 from protruding from plate 600.

Figure 29:
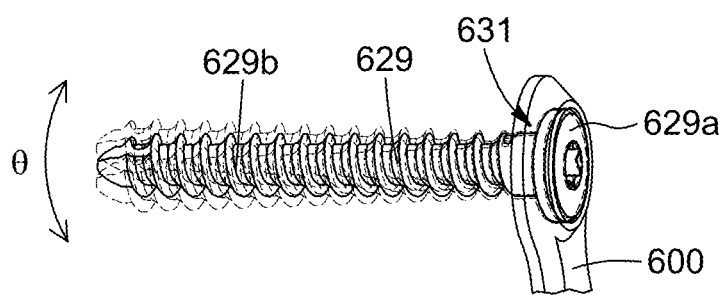
FIG. 29 is a partially transparent, perspective view of the fastener and plate for FIG. 28, showing permitted angulation of the fastener relative to the plate.

In the present embodiment, fastener 609 is configured to allow supplementary angulation while it is inserted during a surgical procedure. As can be appreciated, sidewalls of aperture 610 and/or fastener seat 608 can be angulated such that fastener 609 will be oriented at a predetermined angle when it is inserted into aperture 610, as defined according to the preoperative plan. However, with further reference to FIG. 29, in the present embodiment, the fastener head 629*a* is provided with an undersurface 631 configured to cooperate with fastener seat 608 to allow supplemental fastener angulation □. More specifically, in the present embodiment, undersurface 631 and/or annular recess 608*a* are curved, thereby allowing head 629*a* to pivot slightly in seat 608, thereby allowing a supplemental angulation □ of fastener 609. In this configuration, when the fastener 609 is inserted, it will penetrate the patient's bone 3 generally at an angle as determined preoperatively. However, a surgeon will have the freedom of adjusting the angle of fastener slightly by supplemental angulation □, for example by up to 3 degrees. In some embodiments, a locking element can be provided to lock the angle of fastener 609 after is has been inserted and avoid subsequent movement thereof. For example, a cap element can be screwed over and/or engage with head 629*a* to prevent subsequent angulation of fastener 609.

Although a particular type of fastener 609 was described herein, it is appreciated that other types of fasteners are also possible. For example, in some embodiments, the fastener 609 can be self locking. In such configurations, the fastener head 629*a* can be provided with threads for engaging with corresponding threads seat 608 of plate 600, thereby locking fastener head 629*a* in seat at a predetermined orientation and preventing supplementary angulation thereof.

Preoperative Planning and Surgical Toolkit

As can be appreciated, the tools and guides described above can be provided as part of a surgical toolkit comprising generic and patient-specific components. In other word, the toolkit includes components designed specifically for a patient, and which can only be used to carry out a specific planned surgery (i.e. single use components), and non-specific components which can be re-used during subsequent surgical procedures (i.e. multi-use components). The patient-specific components can be designed and fabricated to assist in performing steps of a high-tibial osteotomy procedure as determined according to a preoperative plan.

Figure 30:
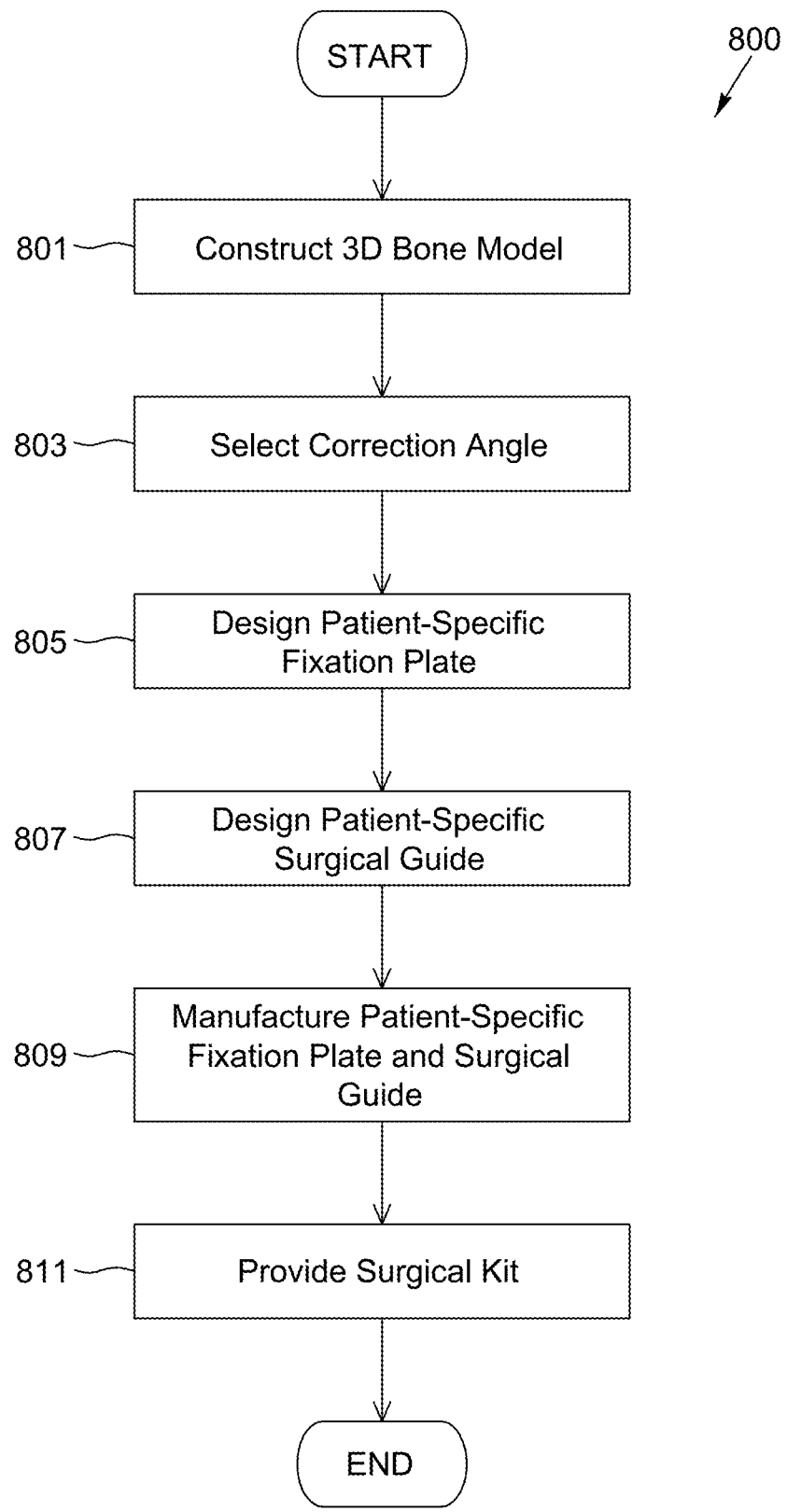
FIG. 30 is a flow chart illustrating a preoperative planning method, according to an embodiment.

With reference to FIG. 30, a preoperative planning method 800 is shown according to an embodiment. The method 800 comprises a first step 801 of constructing a 3D model of a patient's bones. The 3D model can be constructed, for example, by using different types of medical imaging techniques, such as a CT scan, to acquire images of the patient's bones, and assembling said images to form a 3D model which describes the structure of the patient's bones, including their shapes, surfaces, and/or volumes, among other parameters. The 3D model can subsequently be used to preoperatively simulate the effect of surgical interventions on the patient's bones.

A second step 803 of the method can comprise selecting a desired correction angle to apply to the patient's tibia bone via surgical intervention. In an embodiment, a computer program can calculate the mechanical axis of the patient's knee and/or the distribution of stresses within the patient's knee, using the 3D model. The computer program can allow modifying the 3D model to adjust the orientation of the patient's tibia bone relative to the patient's femur. The mechanical axis and/or distribution of stresses in the knee can be recalculated following the adjustment, and a correction angle can be selected once a desired knee alignment has been attained.

As can be appreciated, in some embodiments, the correction angle can be selected automatically by the computer program. In such embodiments, the computer program can determine an optimal correction angle which would result in a mechanical axis which evenly distributes stresses throughout the patient's knee, or which reduces stresses on a worn part of the patient's knee. In other embodiments, the optimal correction angle can be selected by a user. For example, the 3D model, mechanical axis and/or stress distributions can be presented on a display of a computing device, and the user can be provided with controls to adjust the correction angle. As the user adjusts the correction angle, the mechanical axis and the distributions of stresses can be recalculated in real time and shown on the display to help the user visualize the effect of changing the correction angle. The user can then select a desired correction angle once the mechanical axis and/or stress distributions are as desired. In some embodiments, a computer can automatically recommend an optimal correction angle based on predetermined parameters, and the user can adjust the 3D model as necessary to select a final desired correction angle.

Once the correction angle has been selected, a third step 805 can comprise designing a patient-specific fixation plate to retain the patient's tibia bone at the selected correction angle. As can be appreciated, the 3D model can be used to determine the expected shape and form of the patient's bone caused by surgical intervention. More specifically, the steps of the surgical procedure can be simulated using the 3D model, allowing the 3D model to describe the expected shape and form of the patient's bone during and after the surgical procedure. For example, the 3D model of the patient's tibia bone can be virtually cut and opened or closed to attain the selected correction angle. A patient-specific fixation plate can then be designed to conform to the final expected shape and contours of the patient's bone and the open or closed wedge formed therein, based on the shape and form described by the 3D model.

In an embodiment, the fixation plate can be designed from scratch and completely custom made for the patient. Rather than starting from a model or template and modifying the same to conform to the patient (ex: providing a model of a standard T-shaped plate, and modifying the contours of the standard plate to match the contours of the patient's bones), the fixation plate can be designed from scratch based on patient-specific needs, such as a desired number, position, configuration, of fasteners, among others. Accordingly, the fixation plate can be designed with non-standard, complex and/or freeform shapes to conform to patient-specific needs.

For example, in some embodiments, the computer program can provide a user interface which allows the user to design and visualize the fixation plate on the 3D model of the patient's bone. The interface can include controls which allow the user to position fasteners on the patient's bone and customize parameters of each fastener. For example, the user can select a desired fastener from a library including a plurality of fasteners of different types, shapes, lengths, diameters, etc., and select a desired position and orientation of said fastener. The user can continue to position any number of fasteners on the bone as desired. When the fasteners are positioned, the computer program can design a fixation plate which accommodates all the fasteners positioned by the user. For example, the computer program can determine an optimal shape which joins all the fasteners, while providing required structural integrity and support, and reducing weight.

In some embodiments, the program can provide controls which allow the user to further adjust the shape of the plate, while also allowing the user to select other plate parameters, such as wedge types and positions, spacing distance, spacer types and positions, etc. Once the shape and configuration of the plate have been finalized, the computer program can generate a 3D model of the plate. As can be appreciated, the contours of the plate, wedge and/or spacing elements (if applicable) in the generated 3D model can be configured to conform to the contours of the surfaces of the patient's bone (and internal surfaces of the open wedge formed therein, if applicable) as described in the 3D model of the patient's bone. For example, the computer program can determine an expected position of wedge and/or spacing element relative to the bone using the 3D model, determine the expected surface contours at that position, and configure the surface contours of the wedge and/or spacing element to conform to the bone contours at that position.

A fourth step 807 of the preoperative planning method can comprise designing a custom surgical guide for assisting in opening the patient's bone to the selected opening angle and installing the fixation plate. As described above, the 3D model of the patient's bone can be used to simulate different steps of the surgical procedure and determined the expected shape of the patient's bones at the different steps. Accordingly, the computer program can be configured to use the 3D model to design a surgical guide with modules configured to conform to the shape of the patient's bone at the different steps, and guide surgical tools as needed at each step.

For example, the computer program can determine a shape, position, orientation, depth, etc. of a single or biplanar cut to be formed in the patient's bone to attain the required opening angle. The program can then design a drilling module and/or a cutting module configured to conform to the patient's unaltered bone, and cooperate with standard surgical tools such as osteotomes and drill bits to form the cut as planned. Depending on specified surgical requirements, a plurality of drilling and/or cutting modules can be provided, for example to drill and/or cut the patient's bone in different steps, as described above. The guide can further be configured with a guide to position a security pin to protect the tibial plateau throughout the procedure.

The program can further determine the shape, position, orientation, depth, etc. of fasteners for the fixation plate, and design a corresponding predrilling module configured to cooperate with drill bits to predrill holes in the patient's bone for receiving the fasteners in the planned configuration. As described above, in some embodiments, the predrilling module can be configured to drill holes after the opening has been formed in the patient's bone. Accordingly, the predrilling module can be designed to conform to the patient's bone after the opening has been formed in the bone, and can be configured with a positioning element, such as a wedge, for engaging in the opening. In other embodiments, the pre-drilling module can be configured to drill holes for the plate fasteners before the patient's bone is opened. Accordingly, the program can use the 3D model of the patient's bone with the opening and fastener positions defined therein, and virtually close the patient's bone using the model to determine the corresponding position of fasteners on the unopened bone. The program and subsequently design a predrilling module configured to drill holes at positions and orientations in the patient's unopened bone that will correspond with the selected final positions and orientations of the fasteners after the bone is opened at the selected opening angle.

As can be appreciated, the computer program can design further modules to assist in the surgical procedure, including anchor modules, opening validators, etc. as described above. Each of the modules can be configured to conform to the patient's bone based on the 3D model. As can be further appreciated, the modules can be based off premade templates, and customized to conform to patient-specific geometry and to guide surgical tools based on the preoperative plan. Once the guide and its modules have been designed, the computer program can generate 3D models of the same.

Once the custom fixation plate, surgical guide and modules have been designed using the computer program, a fifth step 809 of the preoperative planning method can comprise manufacturing the plate, surgical guide and modules. The plate, guide and modules can be manufactured using the 3D models generated in the previous steps. For example, the 3D models can be used to direct additive manufacturing techniques, such as 3D printing, to physically create the plate, guide and modules as designed. In some embodiments, the pieces can be printed, and subsequently refined using machining techniques and tools. In some embodiments, the plate and spacers (if applicable) can be manufactured using metal, whereas the guide and modules can be manufactured using plastic.

Figure 31A:
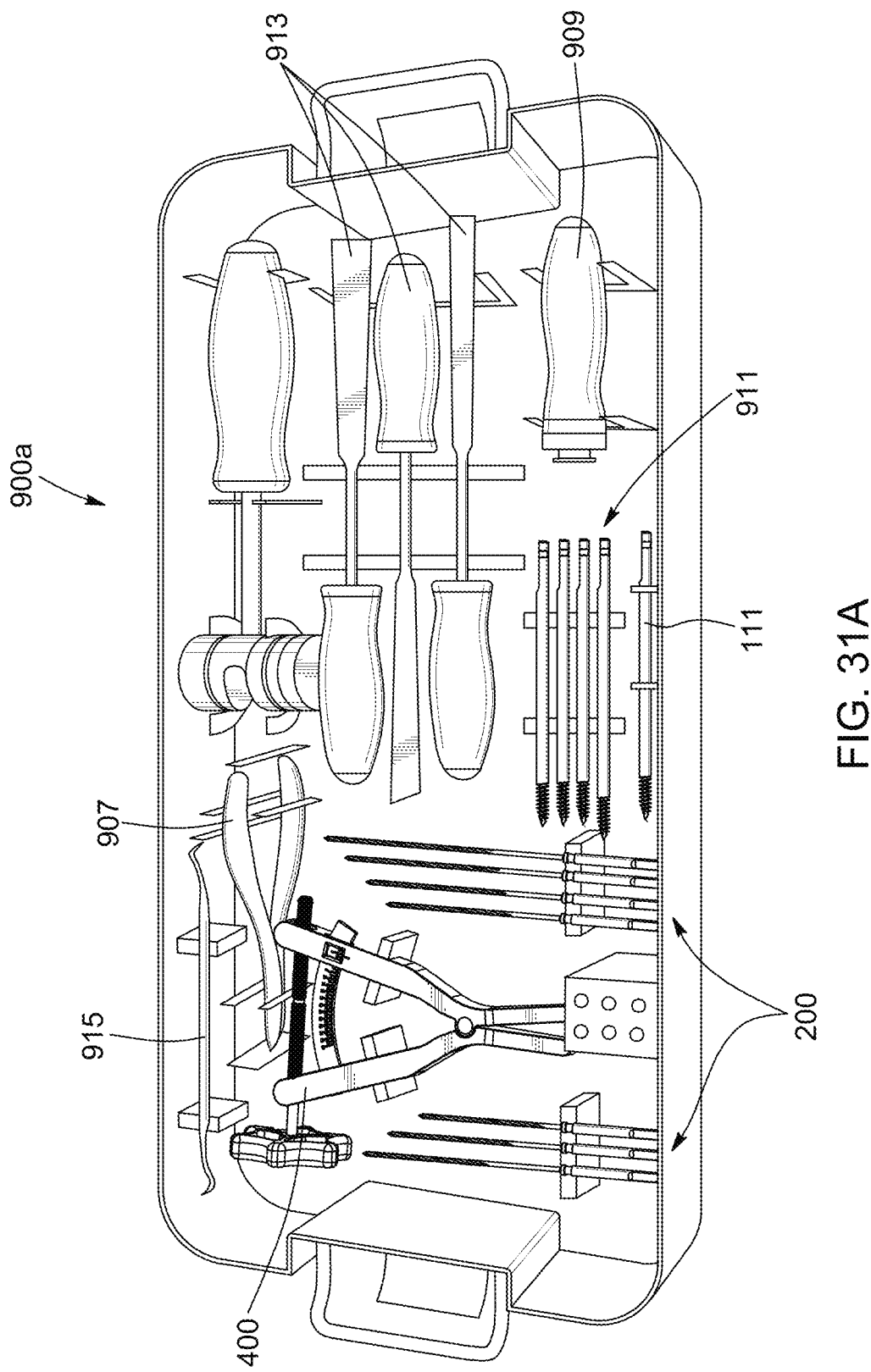
FIGS. 31A and 31B illustrate generic and patient-specific components in a surgical kit, according to an embodiment.
Figure 31B:
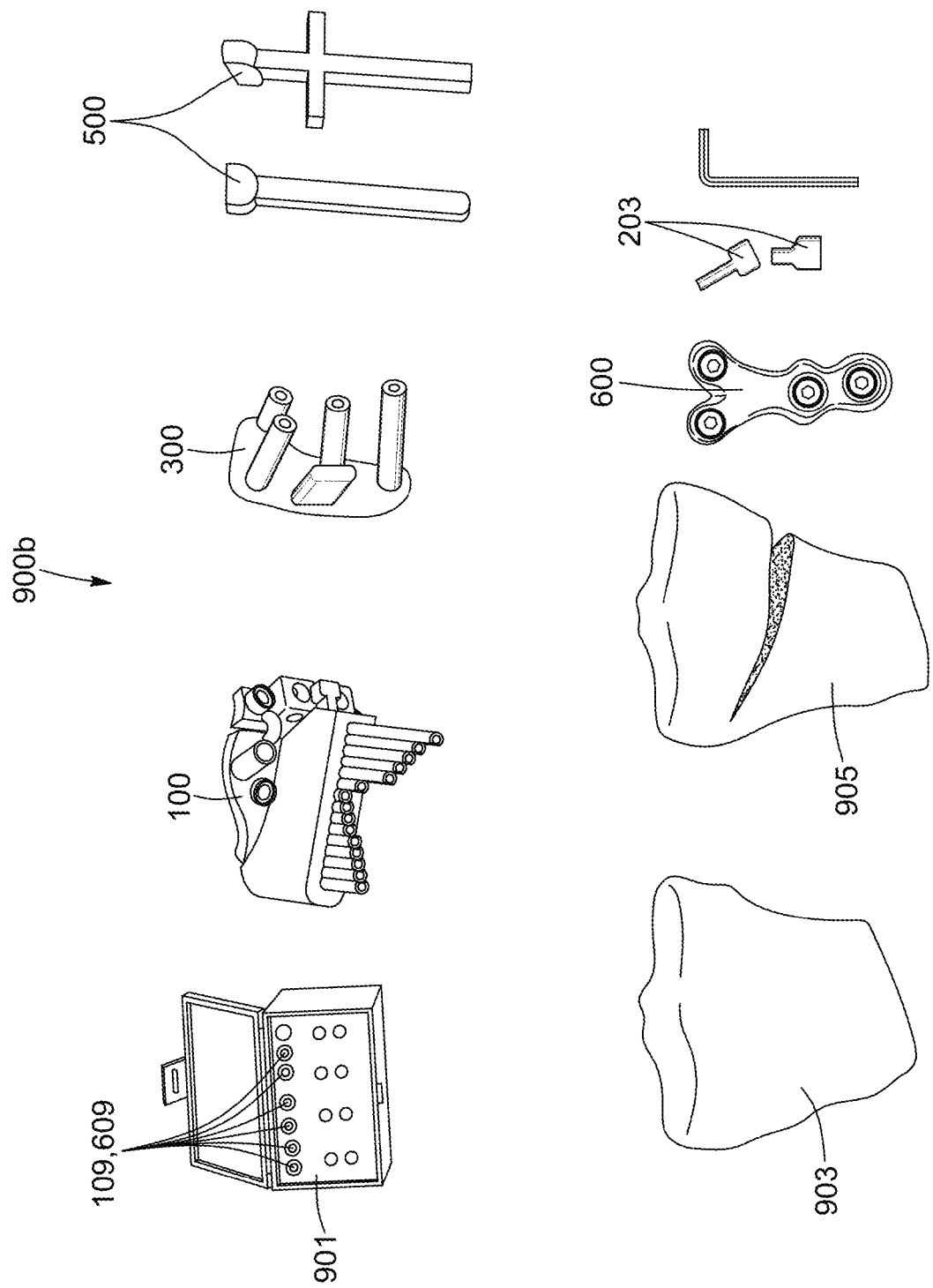

After the various components have been manufactured, a final step 811 of the preoperative planning method can comprise providing the components as part of a surgical kit. As shown in FIGS. 31A and 31B, the surgical kit can include a combination of patient-specific components 900b and generic surgical tools 900a for use therewith. For example, the surgical kit can include patient-specific components 900b such as the fixation plate 600 and the surgical guide 100, including the drilling module, cutting module, anchor module, predrilling module 300, opening validator 500, drill depth guided 203, etc., as described above. The surgical kit can further include a collection or container 901 of the plurality of fasteners 609 chosen to secure the fixation plate in addition to fasteners 109 for securing the surgical guide 100 and modules. In some embodiments, physical models 903, 905 of the patient's bone can be provided, representing the shape of the patient's bone before and/or after the opening is formed therein. Finally, the generic components 900a in the surgical kit can include surgical tools for cooperating with the patient-specific components, such as cutting pliers 907, a spreader module 400, a screwdriver and/or screw bit 909, 911, a security pin 111, calibrated drill bits 200, osteotomes 913, an explorer tool 915, etc., as described above. As can be appreciated, the generic components and/or the patient-specific components can be appropriately labelled to assure the correct tools are used in cooperation with the correct patient-specific components. Although a particular set of components has been described, it is appreciated that the kit can include fewer or more components, depending on the requirements of the surgical procedure.

Surgical Procedure

As can be appreciated, the surgical kit described above can be used to assist in a high-tibial osteotomy procedure to correct the alignment of a patient's knee in accordance with the preoperative plan.

As shown in FIGS. 1A and 1B, a first step of the surgical procedure can comprise positioning the surgical guide 100 on the patient's tibia bone 3. As can be appreciated, the bone interface side 101 of guide is configured to conform to the surface of the patient's bone 3 at a predetermined position. Therefore, an explorer tool can be used to help position the surgical guide 100 correctly, for example by verifying that there are no gaps between the bone interface side 101 and the surface of the patient's bone 3.

Once the guide 100 has been positioned, fasteners 109 can be screwed into the anterior section 107, and then into the lateral section 105 to secure the guide 100 to the patient's bone 3. As can be appreciated, drill bits can be used to predrill holes to prepare for receiving the fasteners 109, if necessary.

After the guide 100 has been secured, security pin 111 can be inserted into the patient's bone 3 through security pin guide 112. The patient's bone 3 can then be weakened in preparation for forming planar cut 5. In this step, calibrated drill bits 200 (as shown in FIGS. 2 and 2A) are inserted through guide cylinders 120 in drilling module 113. The drilling module 113 is then removed by severing connecting members 121a, 121b and 121c, thereby exposing cutting module 117.

An osteotome is inserted through osteotome guide 127 of cutting module 117, and the patient's bone 3 can be cut along the area weekend by drill holes to define planar cut 5 with a hinge axis 9. The cutting module 117 can subsequently be removed by severing connecting members 123a and 123b, and removing fasteners 109 in anterior section 107, leaving only lateral section 105 attached to the bone, along with anchor module 119.

With reference now to FIGS. 3A and 3B, after the cutting module 117 has been removed, pre-drilling module 300 can be positioned relative to the patient's bone 3 by engaging with anchor module 119. Drill bits 200 can subsequently be inserted into drill guides 307 to create the drill holes 308 for eventually receiving fasteners for securing the fixation plate.

As shown in FIGS. 4, 4A and 4B, after drill holes 308 have been formed, spreader module 400 can engage with anchor module 119, and connecting member 126 can be severed, allowing proximal 125a and distal 125b sections of anchor module 119 to be spread apart from one another. The spreader module 400 can be operated towards its open configuration 400b until the desired opening angle in indicated through window 415 of the spreader module's 400 angle scale. As shown in FIGS. 5 and 5a, the opening validator 500 can be inserted into the opening 7 formed in the patient's bone to confirm that it has been opened to the exact desired opening angle. If opening validator 500 does not fit snugly, spreader module 400 can be adjusted to increase or decrease the angle of opening 7, until opening validator 500 fits properly.

As shown in FIG. 6A, once the bone 3 has been opened to the desired angle, fixation plate 600 can secure the bone 3 to retain the opening at the desired angle. In the present embodiment, the drill holes 308 have already been created for receiving plate-securing fasteners 609. Accordingly, plate 600 can be positioned on the patient's bone 3 such that drill holes 308 line up with fastener apertures 610 of plate 600. Positioning of the plate 600 can be further confirmed, if necessary, using an explorer tool to confirm that there is no spacing between cone interface side 603 of plate 600 and the surface of the patient's bone 3. Once the position of plate 600 is confirmed, it can be secured by inserting fasteners 609 into the corresponding fastener apertures 610. After the plate is secured, the surgical procedure is complete, and spreader module 400 can be removed from anchor module 119, anchor module 119 can be removed from the patient's bone 3 by removing its fasteners 109, and security pin 111 can be removed, leaving only plate 600 attached to patient's bone 3.

Although the exemplary procedure described above was in connection with a high-tibial open-wedge osteotomy, it is appreciated that similar steps can apply in connection with a closed-wedge osteotomy. Moreover, although the surgical procedure was described with a particular set and configuration of tools, it is appreciated that a similar procedure can be applied using a different set and configuration of tools. For example, similar steps can apply mutatis mutandis when a plurality of drilling modules are provided (ex: when connected to cutting module via a clip mechanism), when predrilling module is configured to drill holes for plate-securing apertures after the bone is opened, when plate is provided with a wedge, etc.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A surgical kit for performing a bone surgery, the surgical kit comprising:
    a surgical module having a bone interface side with a bone-contacting surface configured to be superposable against a patient's bone, the surgical module comprises a cutting module having an operative side and a slot extending therethrough along a plane, the slot opening on the bone interface side of the surgical module and the operative side of the cutting module;
    an anchor module having a first section and a second section spaced-apart from the first section, each one of the first section and the second section of the anchor module comprising at least one fastener aperture extending therethrough for securing independently each one of the first section and the second section to the patient's bone, each one of the first section and the second section of the anchor module having an anchor module bone interface side with an anchor module bone-contacting surface configured to be superposable against the patient's bone and an anchor module operative side opposite the anchor module bone-contacting surface, wherein the anchor module bone-contacting surfaces of the first section and the second section are configured to conform to a surface of the patient's bone in a predetermined bone-contacting configuration;
    a first connecting member having a first end secured to the surgical module, a second end secured to the first section of the anchor module, and a severable portion extending in between the first end and the second end of the first connecting member;

a second connecting member having a first end secured to the surgical module, a second end secured to the second section of the anchor module, and a severable portion extending in between the first end and the second end of the second connecting member; and a third connecting member having first and second ends secured respectively to the first section and the second section of the anchor module and a severable portion extending in between the first and second ends of the third connecting member, the surgical module being spaced from each one of the first and the second sections of the anchor module and connected thereto via the first and the second connecting members, wherein each one of the severable portions of the first, second, and third connecting members is spaced from the bone interface side of the surgical module and the anchor module bone interface side to facilitate severing thereof, and wherein severing the first and second connecting members enable disconnection of the surgical module from the anchor module and severing the third connecting member enables disconnection of the first and second sections of the anchor module.

2. The surgical kit according to claim 1, wherein the first section of the anchor module comprises a first module interface on the anchor module operative side, and the second section of the anchor module comprises a second module interface on the anchor module operative side, and wherein each one of the first and second module interfaces includes at least one of a male connector protruding therefrom and a female connector defined therein and wherein the at least one of the male connector and the female connector extends substantially normal to the at least one fastener aperture extending through each of the first section and the second section of the anchor module.

3. The surgical kit according to claim 2, wherein the at least one of the male connector and the female connector comprises at least one female connector and the at least one female connector of the first module interface extends substantially parallel to the at least one female connector of the second module interface.

4. The surgical kit according to claim 2, wherein the first and second ends of the third connecting member are respectively secured to the first and the second module interfaces and the third connecting member protrudes outwardly, away from the anchor module operative side of the first section and the second section of the anchor module.

5. The surgical kit according to claim 2, wherein the second end of the first connecting member is secured to the first section of the anchor module adjacent the first module interface, and wherein the second end of the second connecting member is secured to the second section of the anchor module adjacent the second module interface, with the first connecting member and the second connecting member protruding outwardly, away from the anchor module operative side of the first section and the second section and from the surgical module.

6. The surgical kit according to claim 1, wherein each one of the first section and the second section of the anchor module is provided solely on a first side and a second side of the plane, respectively.

7. The surgical kit according to claim 1, wherein the first section of the anchor module comprises a first module interface on the anchor module operative side, and the second section of the anchor module comprises a second module interface on the anchor module operative side, and wherein each one of the first and second module interfaces includes a female connector defined therein and extending substantially parallel to the plane, each one of the female connectors being located on respective sides of the plane.

8. The surgical kit according to claim 7, further comprising a spreader module removably engageable with the female connectors of the first section and the second section of the anchor module, the spreader module comprising two arms pivotally connected to one another, each one of the two arms having a male connector engageable with a corresponding one of the female connectors, the spreader module being operable to further space apart the first section and the second section of the anchor module when they are independently secured to the patient's bone.

9. The surgical kit according to claim 1, wherein the surgical module is spaced-apart from the first section and the second section of the anchor module to define an open space therebetween, and wherein the first connecting member and the second connecting member extend across the open space.

10. The surgical kit according to claim 1, wherein the surgical module further comprises a drill module removably engageable with the cutting module in a predetermined configuration, the drill module comprising a plurality of drill guides adapted to be aligned along the plane and with the slot extending through the cutting module when the drill module is engaged with the cutting module.

11. The surgical kit according to claim 10, wherein the cutting module comprises an osteotome guide protruding outwardly and including sidewalls defining the slot, the osteotome guide further defining a connecting interface for the drill module and the drill module is engageable with the cutting module over the osteotome guide.

12. The surgical kit according to claim 11, further comprising at least one calibrated drill bit including an abutment member, wherein the plurality of drill guides extend parallel to one another with each one of the plurality of drill guides including a guide tunnel defining a guide barrel having a free end, and wherein the at least one calibrated drill bit is removably insertable in at least one of the guide barrels with the abutment member adapted to abut against the free end of the at least one of the guide barrels when at least one of a predetermined depth, position and orientation is reached.

13. The surgical kit according to claim 1, further comprising bone fasteners insertable in each of the at least one fastener aperture and configured to affix the first section and the second section of the anchor module directly to the patient's bone in the predetermined bone-contacting configuration.

14. The surgical kit according to claim 1, wherein the first and second ends of the first connecting member and the second connecting member are connected to the anchor module operative side and to an operative side of the surgical module, respectively, with the first connecting member and the second connecting member protruding outwardly, away from the anchor module operative side of the first section and the second section and from the surgical module.

15. The surgical kit according to claim 1, wherein the third connecting member comprises a third end connected to the surgical module.

16. The surgical kit according to claim 1, wherein the patient's bone is a tibia.

17. The surgical kit according to claim 1, wherein each one of the first connecting member, the second connecting member, and the third connecting member is a stem looping away from respective ones of the surgical module and the first and the second sections of the anchor module.

18. A surgical guide for performing a bone surgery, the surgical guide comprising:
- a surgical module having a bone interface side with a bone-contacting surface configured to be superposable against a patient's bone, the surgical module comprises a cutting module having an operative side and a slot extending therethrough along a plane, the slot opening on the bone interface side of the surgical module and the operative side of the cutting module;
- an anchor module having a first section provided solely on a first side of the plane defined by the slot of the cutting module and a second section spaced-apart from the first section and provided solely on a second side of the plane defined by the slot of the cutting module, each one of the first section and the second section of the anchor module being spaced-apart from the surgical module, each one of the first section and the second section of the anchor module comprising at least one fastener aperture extending therethrough for securing each one of the first section and the second section to the patient's bone, each one of the first section and the second section of the anchor module having an anchor module bone interface side with an anchor module bone-contacting surface configured to be superposable against the patient's bone and an anchor module operative side opposite the anchor module bone-contacting surface;
- a first connecting member having a first end secured to the surgical module, a second end secured to the first section of the anchor module, and a severable portion extending in between the first end and the second end of the first connecting member;
- a second connecting member having a first end secured to the surgical module, a second end secured to the second section of the anchor module, and a severable portion extending in between the first end and the second end of the second connecting member; and
- a third connecting member having first and second ends secured respectively to the first section and the second section of the anchor module and a severable portion extending in between the first and second ends of the third connecting member.

19. A surgical guide for performing a bone surgery, the surgical guide comprising:
- a surgical module having a bone interface side with a bone-contacting surface configured to be superposable against a patient's bone;
- an anchor module having a first section and a second section spaced-apart from the first section, each one of the first section and the second section of the anchor module being spaced-apart from the surgical module, each one of the first section and the second section of the anchor module comprising at least one fastener aperture extending therethrough for securing each one of the first section and the second section to the patient's bone, each one of the first section and the second section of the anchor module having an anchor module bone interface side with an anchor module bone-contacting surface configured to be superposable against the patient's bone and an anchor module operative side opposite the anchor module bone-contacting surface;
- a first connecting member having a first end secured to the surgical module, a second end secured to the first section of the anchor module, and a severable portion extending in between the first end and the second end of the first connecting member;
- a second connecting member having a first end secured to the surgical module, a second end secured to the second section of the anchor module, and a severable portion extending in between the first end and the second end of the second connecting member; and
- a third connecting member having first and second ends secured respectively to the first section and the second section of the anchor module and a severable portion extending in between the first and second ends of the third connecting member;
- wherein each one of the first connecting member, the second connecting member, and the third connecting member is a stem looping away from respective ones of the surgical module and the first and the second sections of the anchor module.

* * * * *